US006479538B1

(12) United States Patent
Reddy

(10) Patent No.: US 6,479,538 B1
(45) Date of Patent: Nov. 12, 2002

(54) CYCLIC ETHER VITAMIN D3 COMPOUNDS, 1α(OH)3-EPI-VITAMIN D3 COMPOUNDS AND USES THEREOF

(75) Inventor: Satayanarayana G. Reddy, Barrington, RI (US)

(73) Assignee: Women and Infants Hospital, Providence, RI (US)

( * ) Notice: Subject to any disclaimer, the term of this patent is extended or adjusted under 35 U.S.C. 154(b) by 0 days.

(21) Appl. No.: 09/617,881

(22) Filed: Jul. 17, 2000

Related U.S. Application Data

(62) Division of application No. 09/079,942, filed on May 15, 1998, now Pat. No. 6,100,294.
(60) Provisional application No. 60/046,690, filed on May 16, 1997.

(51) Int. Cl.[7] ..................... A61K 31/351; C07D 309/04
(52) U.S. Cl. ................ 514/451; 514/460; 549/423; 424/562; 424/573; 424/577
(58) Field of Search .................. 514/451, 460; 549/423; 424/562, 573, 577

(56) References Cited

U.S. PATENT DOCUMENTS

| | | | |
|---|---|---|---|
| 4,021,423 A | 5/1977 | Baggiolini et al. | 260/239.55 |
| 4,038,272 A | 7/1977 | Partridge, Jr. et al. | 260/239.55 |
| 4,188,345 A | 2/1980 | DeLuca et al. | |
| 4,206,131 A | 6/1980 | Salmond | 260/397.2 |
| 4,595,776 A | 6/1986 | Baggiolini et al. | 556/436 |
| 4,711,881 A | 12/1987 | Ikekawa | 514/167 |
| 4,804,502 A | 2/1989 | Baggiolini et al. | 260/397.2 |
| 5,145,846 A | 9/1992 | Baggiolini et al. | 514/167 |
| 5,206,229 A | 4/1993 | Calverley et al. | 514/167 |
| 5,206,230 A | 4/1993 | Ikekawa et al. | 514/167 |
| 5,389,622 A | 2/1995 | Posner et al. | 514/167 |
| 5,401,733 A | 3/1995 | McLane et al. | 514/167 |
| 5,428,029 A | 6/1995 | Doran et al. | 514/167 |
| 5,547,947 A | 8/1996 | Dore et al. | 514/167 |
| 5,789,607 A | 8/1998 | Okabe | 552/505 |
| 5,824,811 A | 10/1998 | Kubodera et al. | 552/653 |
| 5,830,885 A | 11/1998 | Posner | 514/167 |
| 6,121,312 A | 9/2000 | Reddy | 514/451 |

FOREIGN PATENT DOCUMENTS

| | | |
|---|---|---|
| EP | 0 808 831 | 11/1997 |
| EP | 0 808 833 | 11/1997 |
| FR | 2545824 A | 11/1984 |

OTHER PUBLICATIONS

Cota, J.G. et al. "Hydrotitanation–Protonation of Vitamin $D_2$ and Its Analogues: An Efficient Method for the Preparation of 10,19–Dihydrovitamins $D_2$ Including Dihydrotachysterol$_2$," *Journal of Organic Chemistry* 53(26):6094– (1988).

Baggiolini, E. et al., "Stereocontrolled Total Synthesis of 1α25–Dihydroxycholecalciferol and 1α,25–Dihydroxyergocalciferol," *J. Org. Chem.*, vol. 51, 3098–3108 (1986).

Bishop, J. et al., "Profile of Ligand Specificity of the Vitamin D Binding Protein for 1α,25–Dihydroxyvitamin $D_3$ and its Analogs," *Journal of Bone and Mineral Research*, vol. 9, No. 8, 1277–88 (1994).

Bouillon, R. et al., "Biologic Activity of Dihydroxylated 19–Nor–(Pre) Vitamin $D_3$," *Journal of Bone and Mineral Research*, vol. 8, No. 8, 1009–15 (1993).

Bouillon, R. et al., "Structure–Function Relationships in the Vitamin D Endocrine System," *Encocrine Reviews*, vol. 16, No. 2, 200–57 (1995).

Campbell, M. et al., "Vitamin $D_3$ Analogs and Their 24–Oxo Metabolites Equally Inhibit Clonal Proliferation of a Variety of Cancer Cells but Have Differing Molecular Effects," *Journal of Cellular Biochemistry*, vol. 66, 413–25 (1997).

Cross, H. et al., "Vitamin D Metabolism in Human Colon Adenocarcinoma–derived Caco–2 Cells: Expression of 25–Hydroxyvitamin $D_3$ –1α–hydroxylase Activity and Regulation of Side–chain Metabolism," *J. Steroid Biochem. Molec. Biol.*, vol. 62, No. 1, 21–8 (1997).

de Vos, S. et al., "Effects of Potent Vitamin $D_3$ Analogs on Clonal Proliferation of Human Prostate Cancer Cell Lines," *The Prostate*, vol. 31, No. 2, 77–83 (1997).

Dusso, A.S. et al., "On the Mechanisms for the Selective Action of Vitamin D Analogs," *Endocrinology*, vol. 128, No. 4, 1687–92 (1991).

Fioravanti, L. et al., "Synthetic Analogs of Vitamin $D_3$ Have Inhibitory Effects on Breast Cancer Cell Lines," *Anticancer Research*, vol. 18, 1703–8 (1998).

Fleet, J. et al., "1α,25–$(OH)_2$–Vitamin $D_3$ Analogs with Minimal in Vivo Calcemic Activity Can Stimulate Significant Transepithelial Calcium Transport and mRNA Expression in Vitro," *Archives of Biochemistry and Biophysics*, vol. 329, No. 2, 228–34 (1996).

Fleet, J.C. et al., "Effect of A–Ring Diastereomers of 1α,25–Dihydroxy Vitamin $D_3$ on Calcium Transport in Caco–2 Cells," *FASEB J.*, vol. 9, No. 3, 168 (1995) (Abstract).

Gardner, J. et al., "Vitamin D Analog 25–(OH)–16,23E–Diene–26,27–Hexafluoro–Vitamin $D_3$ Induces Differentiation of HL60 Cells with Minimal Effects on Cellular Calcium Homeostasis," *Journal of Cellular Biochemistry*, vol. 63, 500–12 (1996).

(List continued on next page.)

*Primary Examiner*—T. A. Solola
(74) *Attorney, Agent, or Firm*—Lahive & Cockfield, LLP; Peter C. Lauro, Esq.; Elizabeth A. Hanley, Esq.

(57) ABSTRACT

Novel cyclic ether vitamin D3 compounds having a cyclic ether side chain are disclosed. These compounds were first identified as metabolites of 3-epi vitamin D3 produced via a tissue-specific metabolic pathway which catalyzes the formation of a cyclic ether structure. Also disclosed are 1α(OH) 3-epi vitamin D3 compounds, which are produced via the epimerization of a 3-β-hydroxyl group of 1α(OH) vitamin D3 precursor in vivo. The vitamin D3 compounds of the present invention can be used as substitutes for natural and synthetic vitamin D3 compounds.

9 Claims, 36 Drawing Sheets

OTHER PUBLICATIONS

Jung, S. et al., "1,25(OH)$_2$–16ENE–Vitamin D$_3$ is a Potent Antileukemic Agent with Low Potential to Cause Hypercalcemia," *Leukemia Research*, vol. 18, No. 6, 453–63 (1994).

Kim, H. et al., "1,25–Dihydroxy–Vitamin–D$_3$ Enhances Antiproliferative Effect and Transcription of TGF–β1 on Human Keratinocytes in Culture," *Journal of Cellular Physiology*, vol. 151, 579–87 (1992).

Lemire, J. et al., "1,25–Dihydroxy–24–OXO–163n3–Vitamin D3, a Renal Metabolite of the Vitamin D Analog 1,25–Dihydroxy–16ene–vitamin D3, Exerts Immunosuppressive Activity Equal to its Parent Without Causing Hypercalcemia in vivo," *Endocrinology*, vol. 135, No. 6, 2818–21 (1994).

Mayer, E. et al., "23,25–Dihydroxy–24–oxovitamin D$_3$: A Metabolite of Vitamin D$_3$ Made in the Kidney," *Biochemistry*, vol. 22, No. 8, 1798–1805 (1983).

Norman, A. et al., "Demonstration That 1β,25–Dihydroxyvitamin D$_3$ is an Antagonist of the Nongenomic but not Genomic Biological Responses and Biological Profile of the Three A–ring Diasteromers of 1α,25–Dihydroxyvitamin D$_3$," *The Journal of Biological Chemistry*, vol. 268, No. 27, 20022–30 (1993).

Reddy, G.S. and Tserng, KY, "Calcitronic Acid, End Product of Renal Metabolism of 1,25–Dihydroxyvitamin D$_3$ Through C–24 Oxidation Pathway," *Biochemistry*, vol. 28, 1763–9 (1989).

Reddy, G.S. et al., "Metabolism of 1α,25–Dihydroxyvitamin D$_3$ and One of its A–Ring Diastereomer 1α,25–Dihydroxy–3–Epivitamin D$_3$ in Neonatal Human Keratinocytes," *Vitamin D: A Pluripotent Steroid Hormone: Structural Studies, Molecular Endocrinology and Clinical Applications, Prodeedings of the Ninth Workshop on Vitamin D*, Orlando, Fl., 172–3 (May 28–Jun. 2, 1994).

Reddy, G.S. et al., "Stimulation of 24R,25–dihydroxyvitamin D$_3$ Synthesis by Metabolites of Vitamin D$_3$," *Am. J. Physiol.*, vol. 245, No. 4, E359–64 (1983).

Reddy, G.S. et al., "Study of 1,25–Dihydroxyvitamin D$_3$ Induced Alterations in the Metabolism of [$^3$H]25–Hydroxyvitamin D$_3$ Using Isolated Perfused Kidneys From D–Sufficient Rats," *Biochemical and Biophysical Research Communications*, vol. 107, No. 3, 922–8 (1982).

Reichel, H. and Norman, A., "Systemic Effects of Vitamin D," *Ann. Rev. Med.*, vol. 40, 71–8 (1989).

Schwartz, G. et al., "1,25–Dihydroxy–16–ENE–23–YNE–Vitamin D$_3$ and Prostate Cancer Cell Proliferation in Vivo," *Urology*, vol. 46, No. 3, 365–9 (1995).

Siu–Caldera, ML et al., "The Enhanced Biological Activities Ascribed to its Parent Analog, 1α,25(OH)$_2$–16–ene–D$_3$," *J. Steroid Biochem. Molec. Biol.*, vol. 59, No. 5/6, 405–12 (1996).

Veyron, P. et al., "New 20–Epi–Vitamin D3 Analogs: Immunosuppressive Effects on Skin Allograft Survival," *Transplantation Proceedings*, vol. 27, No. 1, 450 (1995).

M/Z

CYCLIC ETHER VITAMIN D3 COMPOUNDS, 1α(OH)3-EPI-VITAMIN D3 COMPOUNDS AND USES THEREOF

RELATED APPLICATIONS

This application is a division of 09/079,942 filed May 15, 1998 now U.S. Pat. No. 6,100,294, and claims priority to U.S. provisional application Application No. 60/046, 690 filed on May 16, 1997, the contents of which are incorporated herein by reference.

BACKGROUND OF THE INVENTION

The importance of the vitamin D in the biological systems of higher animals has been recognized since its discovery by Mellanby in 1920 (Mellanby, E. (1921) *Spec. Rep. Ser. Med Res. Council* (GB) SRS 61:4). It was in the interval of 1920–1930 that vitamin D officially became classified as a "vitamin" that was essential for the normal development of the skeleton and maintenance of calcium and phosphorous homeostasis.

Studies involving the metabolism of vitamin $D_3$ (cholecalciferol) were initiated with the discovery and chemical characterization of the plasma metabolite, 25-hydroxyvitamin $D_3$ [25(OH)$D_3$] (Blunt, J. W. et al. (1968) *Biochemistry* 6:3317–3322) and the hormonally active form, 1α,25(OH)$_2$$D_3$ (Myrtle, J. F. et al. (1970) *J. Biol. Chem.* 245:1190–1196; Norman, A. W. et al. (1971) *Science* 173:51–54; Lawson, D. E. M. et al (1971) *Nature* 230:228–230; Holick, M. F. (1971) *Proc. Natl. Acad. Sci. USA* 68:803–804). The formulation of the concept of a vitamin D endocrine system was dependent both upon appreciation of the key role of the kidney in producing 1α, 25(OH)$_2$$D_3$ in a carefully regulated fashion (Fraser, D. R. and Kodicek, E (1970) *Nature* 288:764–766; Wong, R. G. et al. (1972) *J. Clin. Invest.* 51:1287–1291), and the discovery of a nuclear receptor for 1α,25(OH)$_2$$D_3$ (VD$_3$R) in the intestine (Haussler, M. R. et al. (1969) *Exp. Cell Res.* 58:234–242; Tsai, H. C. and Norman, A. W. (1972) *J. Biol. Chem.* 248:5967–5975). The operation of the vitamin D endocrine system depends on the following: first, on the presence of cytochrome P450 enzymes in the liver (Bergman, T. and Postlind, H. (1991) *Biochem. J.* 276:427–432; Ohyama, Y and Okuda, K. (1991) *J. Biol. Chem.* 266:8690–8695) and kidney (Henry, H. L. and Norman, A. W. (1974) *J. Biol. Chem.* 249:7529–7535; Gray, R. W. and Ghazarian, J. G. (1989) *Biochem. J.* 259:561–568), and in a variety of other tissues to effect the conversion of vitamin $D_3$ into biologically active metabolites such as 1α,25(OH)$_2$$D_3$ and 24R,25(OH)$_2$$D_3$; second, on the existence of the plasma vitamin D binding protein (DBP) to effect the selective transport and delivery of these hydrophobic molecules to the various tissue components of the vitamin D endocrine system (Van Baelen, H. et al. (1988) *Ann NY Acad. Sci.* 538:60–68; Cooke, N. E. and Haddad, J. G. (1989) *Endocr. Rev.* 10:294–307; Bikle, D. D. et al. (1986) *J. Clin. Endocrinol. Metab.* 63:954–959); and third, upon the existence of stereoselective receptors in a wide variety of target tissues that interact with the agonist 1α,25 (OH)$_2$$D_3$ to generate the requisite specific biological responses for this secosteroid hormone (Pike, J. W. (1991) *Annu. Rev. Nutr.* 11:189–216). To date, there is evidence that nuclear receptors for 1α,25(OH)$_2$$D_3$ (VD$_3$R) exist in more than 30 tissues and cancer cell lines (Reichel, H. and Norman, A. W. (1989) *Annu. Rev. Med.* 40:71–78).

Vitamin $D_3$ and its hormonally active forms are well-known regulators of calcium and phosphorous homeostasis. These compounds are known to stimulate, at least one of, intestinal absorption of calcium and phosphate, mobilization of bone mineral, and retention of calcium in the kidneys. Furthermore, the discovery of the presence of specific vitamin D receptors in more than 30 tissues has led to the identification of vitamin $D_3$ as a pluripotent regulator outside its classical role in calcium/bone homeostasis. A paracrine role for 1α,25(OH)$_2$$D_3$ has been suggested by the combined presence of enzymes capable of oxidizing vitamin $D_3$ into its active forms, e.g., 25-OHD-1α-hydroxylase, and specific receptors in several tissues such as bone, keratinocytes, placenta, and immune cells. Moreover, vitamin $D_3$ hormone and active metabolites have been found to be capable of regulating cell proliferation and differentiation of both normal and malignant cells (Reichel, H. et al. (1989) *Ann. Rev. Med.* 40: 71–78).

Given the pluripotent activities of vitamin $D_3$ and its metabolites, much attention has focused on the development of synthetic analogs of these compounds. However, clinical applications of vitamin $D_3$ and its structural analogs have been limited by the undesired side effects elicited by these compounds after administration to a subject, such as the deregulation of calcium and phosphorous homeostasis in vivo that results in hypercalcemia.

SUMMARY OF THE INVENTION

The present invention is based, at least in part, on the discovery of vitamin D3 compounds having a cyclic ether side chain, referred to hereinafter as "cyclic ether vitamin D3 compounds", and which are represented by the formula I. This invention also describes 3-epi forms of 1α-hydroxy-vitamin D3 compounds, which are represented by the formula II. The cyclic ether and 1α-hydroxy-vitamin D3 compounds of formulas I and II, respectively, referred to hereinafter as "vitamin D3 compounds of formulas I and II" can be produced in vivo via a pathway which catalyzes the epimerization 3-β-hydroxy-vitamin D3 in certain tissues, e.g., keratinocytes, bone cells. The vitamin D3 compounds of the present invention can be used as substitutes for natural and synthetic forms of vitamin D3.

Accordingly, the present invention pertains to cyclic ether vitamin D3 compounds having the formula (I) as follows:

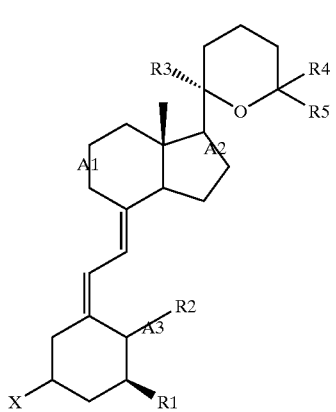

wherein $A_1$, $A_2$ and $A_3$ represent a single or a double bond; X, $R_1$, $R_2$, $R_3$, $R_4$ and $R_5$ can, e.g., be chosen individually from the group of: a hydrogen, a halogen, a haloalkyl, a hydroxy, a hydroxy-protecting group, an alkyl, e.g., a lower alky, an alkenyl, an alkynyl, an alkoxy, an aryl group and a heterocyclic group. The orientation of the X group can be in either an α- or a β-configuration.

In a preferred embodiment, the cyclic ether vitamin D3 compound is in its 3-epi configuration, wherein the orientation of the X group on the A-ring is in an α-configuration.

The present invention also pertains to 3-epi forms of 1α-hydroxy-vitamin D3 compounds having the formula II as follows:

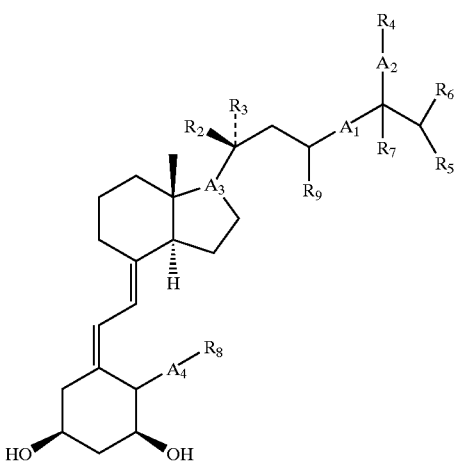

wherein $A_1$ represents a single, a double, e.g., a trans-double, a cis-double, or a triple bond; $A_2$, $A_3$ and $A_4$ represent a single or a double bond; $R_2$, $R_3$, $R_4$, $R_7$, $R_8$ and $R_9$ can, e.g., be chosen individually from the group of: a hydrogen, a deuterium, a deuteroalkyl, a hydroxy, an alkyl, e.g., a lower alkyl, e.g., a $C_1$–$C_4$ alkyl, an alkoxide, an O-acyl, a halogen, e.g., a fluoride, a haloalkyl (e.g., a fluoroalkyl, —$CF_3$), a hydroxyalkyl, e.g., a hydroxyalkyl wherein the alkyl group is a $C_4$–$C_{10}$ alkyl, an amine or a thiol group, and wherein the pairs of $R_2$ and $R_3$, or $R_4$ and $R_7$ taken together can be an oxygen atom, e.g., as in a carbonyl moiety

and $R_5$ and $R_6$ can, e.g., each be chosen individually from the group of: a hydrogen, a deuterium, a halogen, e.g., a fluoride, an alkyl, e.g., a lower alkyl, e.g., a $C_1$–$C_4$ alkyl, a hydroxyalkyl, a haloalkyl, e.g., a fluoroalkyl, and a deuteroalkyl. The amine or thiol group of $R_2$, $R_3$, $R_4$, $R_7$, $R_8$ and $R_9$ can be substituted to form, e.g., a primary or a secondary amine, or a primary or secondary thiol, wherein the substituents can be an alkyl or an aryl group, e.g., a substituent having 2- to 10-carbon atoms.

In another aspect, the present invention further pertains to a pharmaceutical composition comprising, a therapeutically effective amount of a vitamin D3 compound having the formulas I or II, and a pharmaceutically acceptable carrier.

In yet another aspect, this invention provides a method of modulating a biological activity of a vitamin D3-responsive cell. This method comprising contacting the cell with an effective amount of an isolated vitamin D3 compound of formulas I and II such that modulation of the activity of the cell occurs.

Another aspect of the invention provides a method of treating in a subject, a disorder characterized by aberrant growth or activity of a cell, comprising administering to the subject an effective amount of a pharmaceutical composition of a vitamin D3 compound of formulas I and II such that the growth or activity of the cell is reduced.

In a preferred embodiment, the vitamin D3 compound of formulas I and II used in the treatment has improved biological properties compared to vitamin D3, such as enhanced stability and/or reduced toxicity.

In one aspect, a method for inhibiting the proliferation and/or an inducing the differentiation of a hyperproliferative skin cell is provided, wherein the hyperproliferative skin cell can be an epidermal cell or an epithelial cell. Accordingly, therapeutic methods for treating hyperproliferative skin disorders, e.g., psoriasis, are provided.

In certain embodiments, the instant method can be used for the treatment of, or prophylactic prevention of a disorder characterized by aberrant cell growth of vitamin D3-responsive neoplastic cell, e.g., by administering a pharmaceutical preparation of a vitamin D3 compound having the formula as shown in I or II in an amount effective to inhibit growth of the neoplastic cells.

In another aspect, the subject method can be used to modulate an immune response, comprising administering to a subject a pharmaceutical preparation of a vitamin D compound so as to alter immune function in the subject. In one embodiment, the method can be used in the treatment of lymphoid cells, e.g., T cells, natural killer cells, so as to suppress immune reactions, e.g., to decrease T cell activity, e.g., to decrease production of lymphokines such as IL-2 and IFN-γ, to decrease T cell proliferation. In preferred embodients, the method can be used in treating graft rejection, autoimmunity and inflammation.

In yet another aspect, the vitamin D3 compound of the present invention are useful in the treatment of disorder characterized by a deregulation of calcium and phosphate metabolism, comprising administering to a subject a pharmaceutical preparation of a vitamin D3 compounds of formulas I and II so as to ameliorate the deregulation in calcium and phosphate metabolism.

In a preferred embodiment, the disorder is osteoporosis. In other embodiments, the vitamin D3 compounds of formulas I and II can be used to treat diseases characterized by other deregulations in the metabolism of calcium and phosphate.

In another aspect, a method for inhibiting PTH secretion in parathyroid cell using the vitamin D3 compound of formulas I and II is provided. Furthermore, therapeutic methods for treating secondary hyperparathyroidism are also provided.

In yet another aspect, the present invention provides a method of preventing or protecting against neuronal loss by contacting a vitamin D3-responsive cell, e.g., a neuronal cell, with a vitamin D3 compound of formulas I and II to prevent or retard neuron loss.

In yet another aspect, the present invention provides a method of modulating the activity of a vascular smooth muscle cell by contacting a vitamin D3-responsive smooth muscle cell with a vitamin D3 compound of formulas I and II to activate or, preferably, inhibit the activity of the cell.

DETAILED DESCRIPTION OF THE INVENTION

Figure 1:
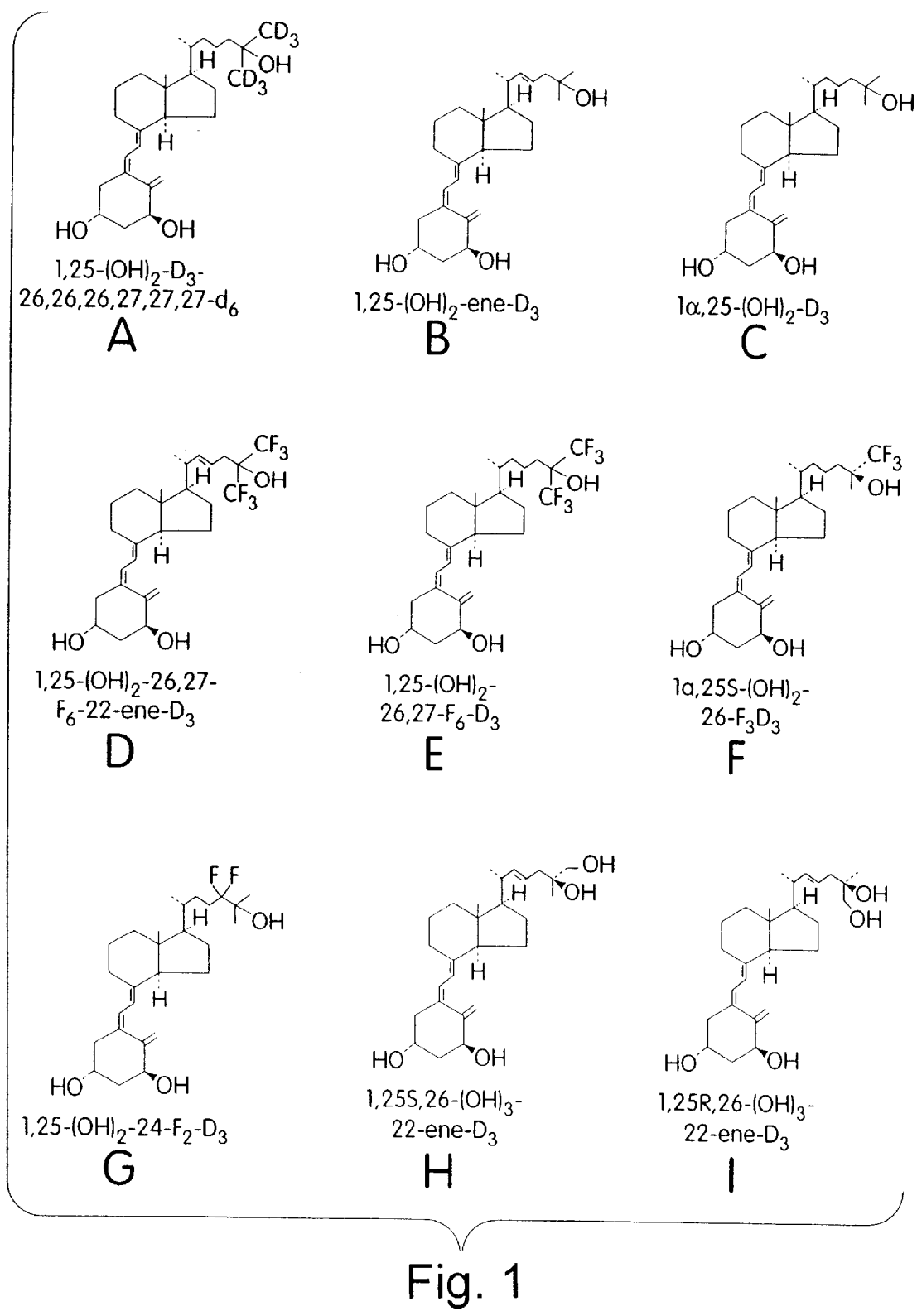
FIGS. 1A, 1A1 to 1A28 are compilations of the chemical structures of 266 vitamin $D_3$ compounds (Boullion, R. et al. (1995) *Endocrinology Reviews* 16(2): 200–257, the contents of which including the figures depicted therein are incorporated by reference). Each analog is identified by its chemical name and a one, two, or three-letter identification code.
Figure 1A:
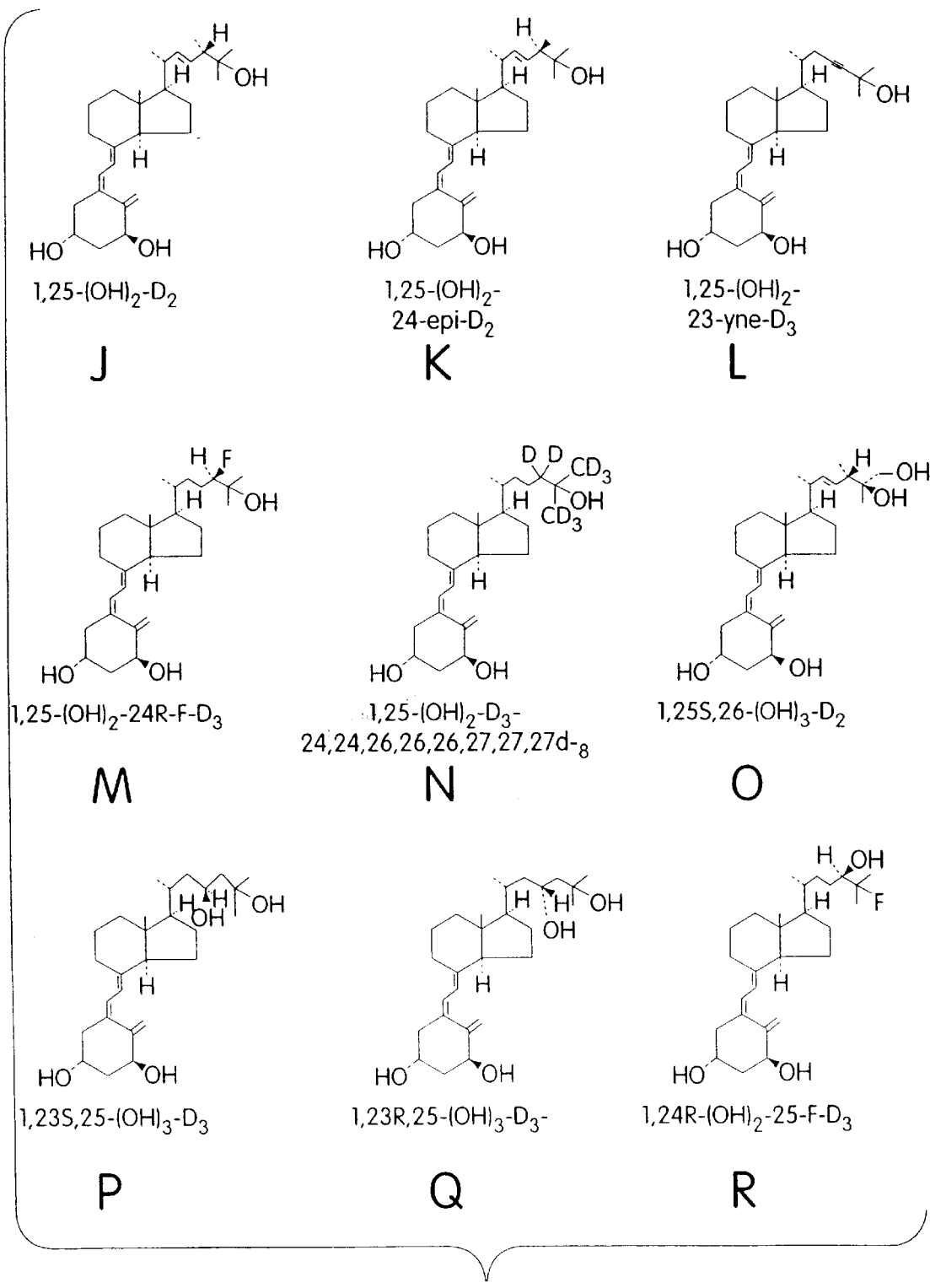
Figures 1, 1A:
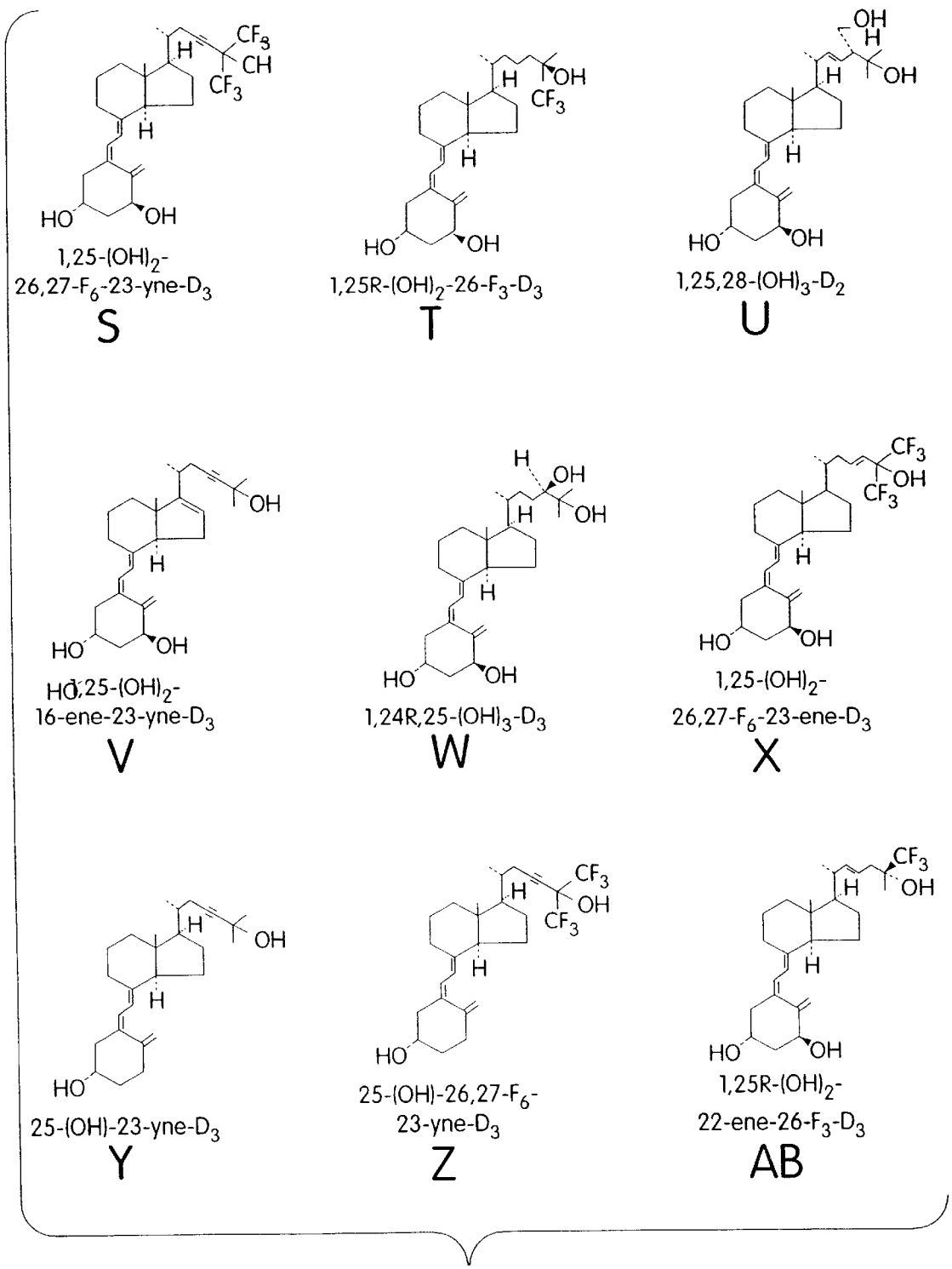

The language "cyclic ether vitamin D3 compound" is intended to include all vitamin D3 compounds having a cyclic ether side chain, including 3-epimeric and non-3-epimeric of vitamin D3 as represented by the general formula I.

As used herein, the terms "3-epi vitamin D3" or "3-epi D3" compounds are intended to include vitamin D3 compounds having a substituent, e.g., a functional group, e.g., a hydroxyl group, attached to the carbon at position 3 of the A-ring in an α-configuration rather than a β-configuration. The language "3-epi forms of 1α-hydroxy-vitamin D3 compounds" or "1α-hydroxy-3-epi-vitamin D3 compounds" is intended to include 1α-hydroxy-vitamin D3 compounds having the hydroxyl group, attached to the carbon at position 3 of the A-ring in an α-configuration rather than a β-configuration, and which are represented by the general formula II as described in detail below.

The cyclic ether and 1α-hydroxy-vitamin D3 compounds of formulae I and II, respectively, referred to hereinafter as "vitamin D3 compounds of formulas I and II" can be produced in vivo via a pathway which catalyzes the epimerization 3-β-hydroxy-vitamin D3 in certain tissues, e.g., keratinocytes or bone cells.

The language "vitamin D3 compounds" or "cholecalciferols" (also referred to herein as "D3 compounds") is intended to include compounds which are structurally similar to vitamin D$_3$. Many of these compounds are art-recognized and comprise a large number of natural precursors, metabolites, as well as synthetic analogs of the hormonally active 1α,25-dihydroxyvitamin D$_3$ (1α,25(OH)$_2$D$_3$). This language is intended to include vitamin D$_3$, or an analog thereof, at any stage of its metabolism, as well as mixtures of different metabolic forms of vitamin D$_3$ or analogs thereof. Furthermore, the term "vitamin D$_3$ compound" also includes synthetic analogs of vitamin D$_3$ illustrated in FIG. 1.

In the formulas presented herein, the various substituents are illustrated as joined to the steroid nucleus by one of these notations: a dotted line (----) indicating a substituent which is in the β-orientation (i.e., above the plane of the ring), a wedged solid line (▼) indicating a substituent which is in the α-orientation (i.e., below the plane of the molecule), or a solid line (—) indicating a substituent in the plane of the ring. It should be understood that the stereochemical convention in the steroid field is opposite from the general chemical field, wherein a dotted line indicates a substituent which is in an α-orientation (i.e., below the plane of the molecule), and a wedged solid line indicates a substituent which is in the β-orientation (i.e., above the plane of the ring). As shown, the A ring of the hormone 1α,25(OH)$_2$D$_3$ contains two asymmetric centers at chiral carbons-1 and -3, each one containing a hydroxyl group in well-characterized configurations, namely the 1α- and 3β- hydroxyl groups.

Accordingly, the present invention pertains to cyclic ether vitamin D3 compounds having the formula (I) as follows:

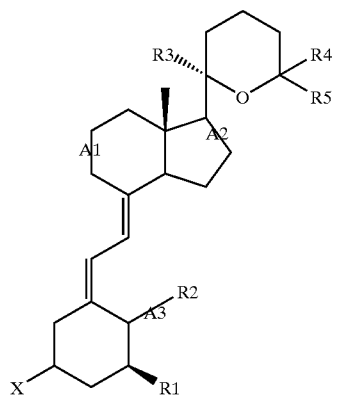

I wherein A$_1$, A$_2$ and A$_3$ represent a single or a double bond; X, R$_1$, R$_2$, R$_3$, R$_4$ and R$_5$ can, e.g., be chosen individually from the group of: a hydrogen, a halogen, a haloalkyl, a hydroxy, a hydroxy-protecting group, an alkyl, e.g., a lower alkyl, an alkenyl, an alkynyl, an alkoxy, an aryl group and a heterocyclic group. The orientation of the X group can be in either an α- or a β-configuration.

In a preferred embodiment, the cyclic ether vitamin D3 compound is represented by the general formula I, wherein the orientation of the X group on the A-ring is in an α-configuration; A$_1$ is a single bond; A$_2$ and A$_3$ are each a double bond; -X and R$_1$ are hydroxyl groups; R$_2$, R$_3$, R$_4$ and R$_5$ are a hydrogen.

The present invention also pertains to 3-epi forms of 1α-hydroxy-vitamin D3 compounds having the formula II:

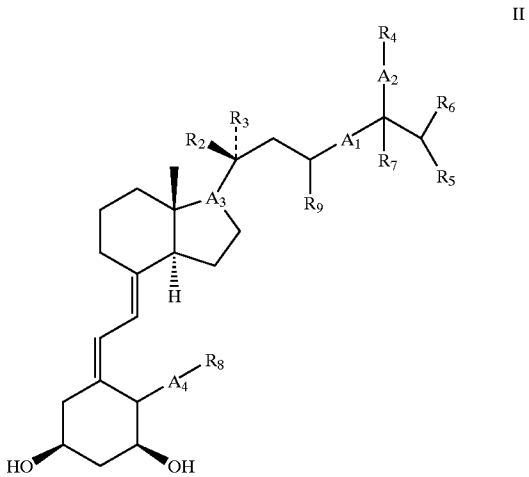

II wherein A$_1$ represents a single, a double, e.g., a trans-double, a cis-double, or a triple bond; A$_2$, A$_3$ and A4 represent a single or a double bond; R$_2$, R$_3$, R$_4$, R$_7$, R$_8$ and R$_9$ can, e.g., be chosen individually from the group of: a hydrogen, a deuterium, a deuteroalkyl, a hydroxy, an alkyl, e.g., a lower alkyl, e.g., a C$_1$–C$_4$ alkyl, an alkoxide, an O-acyl, a halogen, e.g., a fluoride, a haloalkyl (e.g., a fluoroalkyl, —CF$_3$), a hydroxyalkyl, e.g., a hydroxyalkyl wherein the alkyl group is a C$_4$–C$_{10}$ alkyl, an amine or a thiol group, and wherein the pairs of $R_2$ and $R_3$, or $R_4$ and $R_7$ taken together can be an oxygen atom, e.g., as in a carbonyl moiety

and $R_5$ and $R_6$ can, e.g., each be chosen individually from the group of: a hydrogen, a deuterium, a halogen, e.g., a fluoride, an alkyl, e.g., a lower alkyl, e.g., a $C_1$–$C_4$ alkyl, a hydroxyalkyl, a haloalkyl, e.g., a fluoroalkyl, and a deuteroalkyl. The amine or thiol group of $R_2$, $R_3$, $R_4$, $R_7$, $R_8$ and $R_9$ can be substituted to form, e.g., a primary or a secondary amine, or a primary or a secondary thiol, wherein the substituents can be an alkyl or an aryl group, e.g., a substituent having 2- to 10-carbon atoms.

In a preferred embodiment, $A_1$, $A_2$ and $A_3$ are each a single bond; $A_4$ is a double bond; $R_2$, $R_3$, $R_5$, $R_6$, $R_8$ and $R_9$ are each a hydrogen or an alkyl, e.g., a methyl; and $R_4$ and $R_7$ are each a hydrogen, a hydroxy or an alkyl, e.g., a lower alkyl, e.g., a methyl or an ethyl group. The chirality of the positions substituted by $R_4$ and $R_7$ can be in either an R- or an S-configuration.

Exemplary preferred 1α-hydroxy vitamin $D_3$ compounds encompassed by formula II include: 1α hydroxy 3-epi vitamin $D_3$, 1α,24 dihydroxy 3-epi vitamin $D_3$ (both 1α, 24R-dihydroxy 3-epi vitamin $D_3$ and 1α, 24S-dihydroxy 3-epi vitamin $D_3$), 1α hydroxy 24-ethyl 3-epi vitamin $D_3$, 1α hydroxy 24-methyl 3-epi vitamin $D_3$ and α, 24-dihydroxy 24-methyl 3-epi vitamin $D_3$ having the following chemical formulae:

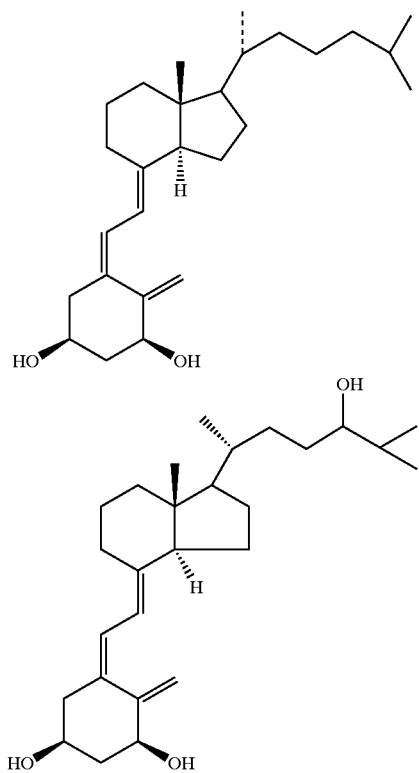

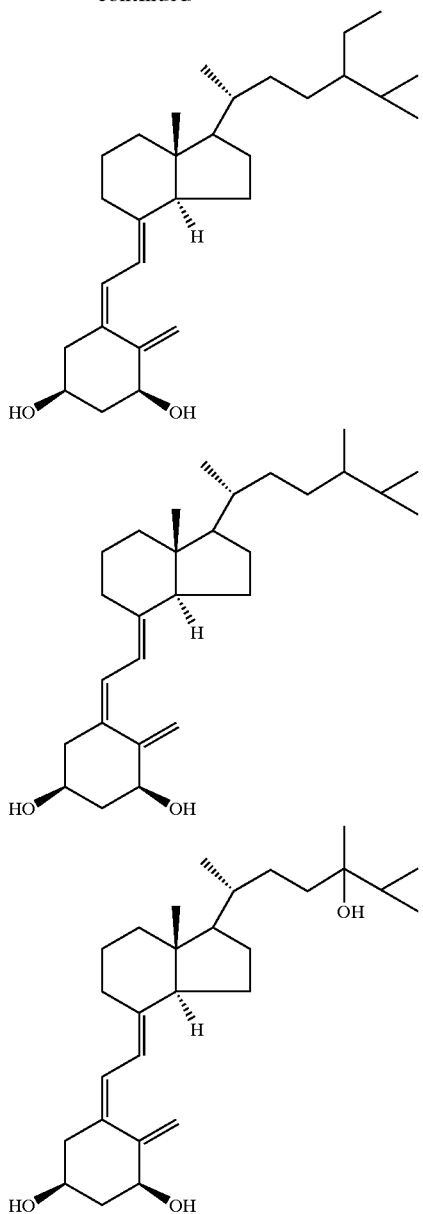

A representation of I α-hydroxy-vitamin D3 prior to 3-epi conversion is also depicted as analog BP in FIG. 1.

In yet another embodiment, the present invention provides isolated vitamin D3 compounds of formulae I and II, having at least one biological activity of vitamin D3, and having improved biological properties compared to vitamin D3, such as enhanced stability in vivo and/or reduced toxicity.

The term "epimer" or "epi" compounds is intended to include compounds having a chiral carbon that varies in the orientation of a single bond to a substituent on that carbon compared to the naturally-occurring (or reference) compound, for example, a carbon where the orientation of the bond to the substituent is in an α-configuration, instead of a β-configuration. The 3-epimer forms of vitamin D3 compounds having the general formulas I and II have a substituent, e.g., a hydroxyl group, attached to the carbon at position 3 of the A-ring in an α-configuration rather than a β-configuration, whereas all other substituents can be in either an α- or a β-configuration.

As used herein, the term "substituent" refers to a moiety, for example a functional group, attached to the carbon position 3 of the A ring of the vitamin $D_3$ compound that allows the compound to perform its intended function. Accordingly, the term "substituent" is intended to include hydrogen, halogen, haloalkyl, hydroxy, hydroxy-protecting group, alkyl, e.g. lower alkyl, alkenyl, e.g.,lower alkenyl, alkynyl, e.g., lower alkynyl, alkoxy, aryl group and heterocyclic group.

The term "chiral" refers to molecules which have the property of non-superimposability of the mirror image partner, while the term "achiral" refers to molecules which are superimposable on their mirror image partner. The term "stereoisomers" or "isomers" refer to compounds which have identical chemical constitution, but differ with regard to the arrangement of the atoms or groups in space. In particular, "enantiomers" refer to two stereoisomers of a compound which are non-superimposable mirror images of one another. An equimolar mixture of two enantiomers is called a "racemic mixture" or a "racemate". "Diastereomers" refer to stereoisomers with two or more centers of dissymmetry and whose molecules are not mirror images of one another. With respect to the nomenclature of a chiral center, terms "d" and "l" configuration are as defined by the IUPAC Recommendations. As to the use of the terms, diastereomer, racemate, epimer and enantiomer will be used in their normal context to describe the stereochemistry of preparations.

As used herein, the language "isomeric counterparts of vitamin D3" or "non-epimeric forms" refers to stereoisomers of the 3-epi vitamin D3 compounds. For example, vitamin D3 compounds which have the orientation of the 3-hydroxy group in a β-configuration.

The terms "isolated" or "substantially purified" as used interchangeably herein refer to vitamin $D_3$ compounds in a non-naturally occurring state. The compounds can be substantially free of cellular material or culture medium when naturally produced, or chemical precursors or other chemicals when chemically synthesized. In other preferred embodiments, the terms "isolated" or "substantially purified" also refer to preparations of a chiral compound which substantially lack one of the enantiomers, i.e., enantiomerically enriched or non-racemic preparations of a molecule. Similarly, isolated epimers or diasteromers refers to preparations of chiral compounds which are substantially free of other stereochemical forms. For instance, isolated or substantially purified vitamin $D_3$ compounds includes synthetic or natural preparations of a vitamin $D_3$ enriched for the stereoisomers having a substituent attached to the chiral carbon at position 3 of the A-ring in an α-configuration, and thus substantially lacking other isomers having a β-configuration. Unless otherwise specified, such terms refer to vitamin $D_3$ compositions in which the ratio of α to β forms is greater that 1:1 by weight. For instance, an isolated preparation of an α epimer means a preparation having greater than 50% by weight of the α-epimer relative to the β stereoisomer, more preferably at least 75% by weight, and even more preferably at least 85% by weight. Of course the enrichment can be much greater than 85%, providing a "substantially epimer enriched", which refers to preparations of a compound which have greater than 90% of the α-epimer relative to the β stereoisomer, and even more preferably greater than 95%. The term "substantially free of the β stereoisomer" will be understood to have similar purity ranges.

As used herein, the language "alkyl" is art-recognized and includes to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$–$C_{30}$ for straight chain, $C_3$–$C_{30}$ for branched chain), and more preferably 20 or fewer. Likewise, preferred cycloalkyls have from 4–10 carbon atoms in their ring structure, and more preferably have 5, 6 or 7 carbons in the ring structure.

Unless the number of carbons is otherwise specified, "lower alkyl" as used herein means an alkyl group, as defined above, but having from one to ten carbons, more preferably from one to six, and most preferably from one to four carbon atoms in its backbone structure, which may be straight or branched-chain, which may be straight or branched-chain. Examples of lower alkyl groups include methyl, ethyl, n-propyl, i-propyl, tert.-butyl, hexyl, heptyl, octyl and so forth. Likewise, "lower alkenyl" and "lower alkynyl" have similar chain lengths. Preferred alkyl groups include lower alkyls. Examples of alkylene groups are methylene, ethylene, propylene and so forth.

Moreover, the term alkyl as herein is intended to include both "unsubstituted alkyls" and "substituted alkyls", the latter of which refers to alkyl moieties having substituents replacing a hydrogen on one or more carbons of the hydrocarbon backbone. Such substituents can include, for example, halogen, hydroxyl, carbonyl (including aldehydes, ketones, carboxylates, and esters), alkoxyl, ether, phosphoryl, cyano, amino, acylamino, amido, amidino, imino, sulfhydryl, alkylthio, arylthio, thiolcarbonyl (including thiolformates, thiolcarboxylic acids, and thiolesters), sulfonyl, nitro, heterocyclyl, aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, acylaminos, iminos, amidos, phosphoryls (including phosphonates and phosphinates), sulfonyls (including sulfates, sulfonatos, sulfamoyls, and sulfonamidos), and silyl groups, as well as ethers, alkylthios, arylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, arylthios, aminoalkyls, carbonyl-substituted alkyls, —$CF_3$, cyano (—CN), and the like.

The term "aralkyl", as used herein, refers to an alkyl group substituted with an aryl group (e.g., an aromatic or heteroaromatic group).

The terms "alkenyl" and "alkynyl" are art-recognized and include to unsaturated aliphatic groups analogous in length and possible substitution to the alkyls described above, but that contain at least one double or triple bond respectively.

The terms "alkoxyl" is art-recognized and includes to an group represented by the formula —O-alkyl. Representative alkoxyl groups include methoxy, ethoxy, propoxy, tert-butoxy and the like. Unless otherwise specified, an "alkoxy" group can be replaced with a group represented by —O-alkenyl, —O-alkynyl, —O-aryl (i.e., an aryloxy group), or —O-heterocyclyl. An "ether" is two substituted or unsubstituted hydrocarbons covalently linked by an oxygen. Accordingly, the substituent of, e.g., an alkyl that renders that alkyl an ether is or resembles an alkoxyl, such as can be represented by one of —O-alkyl, —O-alkenyl, —O-alkynyl, —O-aryl, or —O-heterocyclyl. The term "lower alkoxy" includes a lower alkyl group attached to the remainder of the molecule by oxygen.

Examples of alkoxy groups include methoxy, ethoxy, isopropoxy, tert.-butoxy and so forth. The term "phenyl alkoxy" refer to an alkoxy group which is substituted by a phenyl ring. Examples of phenyl alkoxy groups are benzyloxy, 2-phenylethoxy, 4-phenylbutoxy and so forth. The term "alkanoyloxy group" refers to the residue of an alkylcarboxylic acid formed by removal of the hydrogen from the hydroxyl portion of the carboxyl group. Examples of alkanoyloxy groups include formyloxy, acetoxy, butyryloxy, hexanolyoxy and so forth. The term "substituted" as applied to "phenyl" refers to phenyl which is substituted with one or more of the following groups: alkyl, halogen (i.e., fluorine, chlorine, bromine or iodine), nitro, cyano, trifluoromethly and so forth. The "alkanol" or a "hydroxyalkyl" refer to a compound derived by protonation of the oxygen atom of an alkoxy group. Examples of alkanols include methanol, ethanol, 2-propanol, 2-methyl-2-propanol and the like.

As used herein the term "hydroxy-protecting group" includes any group commonly used for the protection of hydroxy functions during subsequent reactions, including, for example, acyl or alkylsilyl groups such as trimethylsilyl, triethylsilyl, t-butyldimethylsilyl and analogous alkylated silyl radicals, or alkoxyalkyl groups such as methoxymethyl, ethoxymethyl, methoxyethoxymethyl, tetrahydrofuranyl or tetrahydropyranyl. A "protected-hydroxy" is a hydroxy function derivatized by one of the above hydroxy-protecting groupings.

As used herein, the term "halogen" designates —F, —Cl, —Br or —I; the term "sulfhydryl" or "thiol" means —SH; the term "hydroxyl" means —OH.

The term "aryl" is art-recognized and includes 5- and 6-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Aryl groups also include polycyclic fused aromatic groups such as naphthyl, quinolyl, indolyl, and the like. Those aryl groups having heteroatoms in the ring structure may also be referred to as "aryl heterocycles", "heteroaryls" or "heteroaromatics". The aromatic ring can be substituted at one or more ring positions with such substituents as described above, as for example, halogen, alkyl, aralkyl, alkenyl, alkynyl, cycloalkyl, hydroxyl, amino, acylamino, azido, nitro, sulfhydryl, imino, amido, amidino, phosphonate, phosphinate, carbonyl, carboxyl, silyl, ether, alkylthio, arylthio, sulfonyl, sulfonamido, sulfamoyl, ketone, aldehyde, ester, a heterocyclyl, an aromatic or heteroaromatic moiety, —$CF_3$, —CN, or the like. Aryl groups can also be fused or bridged with alicyclic or heterocyclic rings which are not aromatic so as to form a polycycle (e.g., tetralin).

The terms "heterocyclyl" or "heterocyclic group" are art-recognized and include 3- to 10-membered ring structures, more preferably 4- to 7-membered rings, which ring structures include one to four heteroatoms. Heterocyclyl groups include pyrrolidine, oxolane, thiolane, imidazole, oxazole, piperidine, piperazine, morpholine, lactones, lactams such as azetidinones and pyrrolidinones, lactones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, acylamino, nitro, sulfhydryl, imino, amido, phosphonate, phosphinate, carbonyl, carboxyl, silyl, ether, alkylthio, arylthio, sulfonyl, ketone, aldehyde, ester, a heterocyclyl, an aromatic or heteroaromatic moiety, —$CF_3$, —CN, or the like.

The terms "polycyclyl" or "polycyclic group" are art-recognized and include two or more cyclic rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, acylamino, nitro, sulfhydryl, imino, amido, phosphonate, phosphinate, carbonyl, carboxyl, silyl, ether, alkylthio, arylthio, sulfonyl, ketone, aldehyde, ester, a heterocyclyl, an aromatic or heteroaromatic moiety, —$CF_3$, —CN, or the like.

Vitamin D Synthesis The vitamin D3 compounds of the present invention can be prepared using a variety of synthetic methods, as are known in the art. For example, many of the above-described compounds can be prepared by chemical synthesis, or alternatively by enzymatic conversion of a 3β-vitamin D3 precursor, e.g., by perfusing a 3β-vitamin D3 precursor, a vitamin D3 compound having the orientation of the hydroxy group at position 3 of the A-ring in a β-configuration, in a tissue-containing an enzyme which catalyzes the epimerization of the 3-β-hydroxyl group to the 3α form vitamin D3 compounds, e.g., keratinocytes or bone cells as described in Examples I, II and IV.

For example, methods for synthesizing vitamin D3 compounds of formulas I and II are well known in the art (see e.g., Bouillon, R. et al., *Endocrine Reviews* 16(2):201–204; Ikekawa N. (1987) *Med. Res. Rev.* 7:333–366; DeLuca H. F. and Ostrem V. K. (1988) *Prog. Clin. Biol. Res.* 259:41–55; Ikekawa N. and Ishizuka S. (1992) CRC Press 8:293–316; Calverley M. J. and Jones G. (1992) Academic Press 193–270; Pardo R. and Santelli M. (1985) *Bull. Soc. Chim. Fr*:98–114; Bythgoe B. (1980) *Chem. Soc. Rev.* 449–475; Quinkert G. (1985) *Synform* 3:41–122; Quinkert G. (1986) *Synform* 4:131–256; Quinkert G. (1987) *Synform* 5:1–85; Mathieu C. et al. (1994) *Diabetologia* 37:552–558; Dai H. and Posner G. H. (1994) *Synthesis* 1383–1398). Exemplary methods of synthesis include the photochemical ring opening of a 1-hydroxylated side chain-modified derivative of 7-dehydrocholesterol which initially produces a previtamin that is easily thermolyzed to vitamin D3 in a well known fashion (Barton D. H. R. et al. (1973) *J. Am. Chem. Soc.* 95:2748–2749; Barton D. H. R. (1974) *JCS Chem. Comm.* 203–204); phosphine oxide coupling method developed by (Lythgoe et al (1978) *JCS Perkin Trans.* 1:590–595) which comprises coupling a phosphine oxide to a Grundmann's ketone derivative to directly produce a 1α,25(OH)$_2$D3 skeleton as described in Baggiolini E. G. et al. (1986) *J. Org. Chem.* 51:3098–3108; DeSchrijver J. and DeClercq P. J. (1993) *Tetrahed Lett* 34:4369–4372; Posner G. H and Kinter C. M. (1990) *J. Org. Chem.* 55:3967–3969; semihydrogenation of dienynes to a previtamin structure that undergoes rearrangement to the corresponding vitamin D3 analog as described by Harrison R. G. et al. (1974) *JCS Perkin Trans.* 1:2654–2657; Castedo L. et al. (1988) *Tetrahed Lett* 29:1203–1206; Mascarenas J. S. (1991) *Tetrahedron* 47:3485–3498; Barrack S. A. et al. (1988) *J. Org. Chem.* 53:1790–1796) and Okamura W. H. et al. (1989) *J. Org Chem.* 54:4072–4083; the vinylallene approach involving intermediates that are subsequently arranged using heat or a combination of metal catalyzed isomerization followed by sensitized photoisomerization (Okamura W. H. et al. (1989) *J. Org. Chem.* 54:4072–4083; Van Alstyne E. M. et al. (1994) *J. Am. Chem. Soc.* 116:6207–6210); the method described by Trost et al. B. M. et al. *J. Am. Chem. Soc.* 114:9836–9845; Nagasawa K. et al. (1991) *Tetrahed Lett* 32:4937–4940 involves an acyclic A-ring precursor which is intramolecular cross-coupled to the bromoenyne leading directly to the formation of 1,25(OH)$_2$D3 skeleton; a tosylated derivative which is isomerized to the i-steroid that can be modified at carbon-1 and then subsequently back-isomerized under sovolytic conditions to form 1α,25(OH)$_2$D2 or analogs thereof (Sheves M. and Mazur Y. (1974) *J. Am. Chem. Soc.* 97:6249–6250; Paaren H. E. et al. (1980) *J. Org. Chem.* 45:3253–3258; Kabat M. et al. (1991) *Tetrahed Lett* 32:2343–2346; Wilson S. R. et al. (1991) *Tetrahed Lett* 32:2339–2342); the direct modification of vitamin D derivatives to 1-oxygenated 5, 6-trans vitamin D as described in (Andrews D. R. et al. (1986) *J. Org. Chem.* 51:1635–1637); the Diels-Alders cycloadduct method of previtamin D3 can be used to cyclorevert to 1α,25(OH)$_2$D2 through the intermediary of a previtamin form via thermal isomerization (Vanmaele L. et al. (1985) *Tetrahedron* 41:141–144); and, a final method entails the direct modification of 1α,25(OH)$_2$D2 or an analog through use of suitable protecting groups such as transition metal derivatives or by other chemical transformations (Okarmura W. H. et al. (1992) *J. Cell Biochem.* 49:10–18). Additional methods for synthesizing vitamins D2 compounds are described in, for example, Japanese Patent Disclosures Nos. 62750/73, 26858/76, 26859/76, and 71456/77; U.S. Pat. Nos. 3,639,596; 3,715,374; 3,847,955 and 3,739,001.

Examples of the compounds of this invention having a saturated side chain can be prepared according to the general process illustrated and described in U.S. Pat. No. 4,927,815, the description of which is incorporated herein by reference. Examples of the compounds of this invention having an unsaturated side chain is can be prepared according to the general process illustrated and described in U.S. Pat. No. 4,847,012, the description of which is incorporated herein by reference. Examples of the compounds of this invention wherein R groups together represent a cyclopentano group can be prepared according to the general process illustrated and described in U.S. Pat. No. 4,851,401, the description of which incorporated herein by reference.

Another synthetic strategy for the preparation of side-chain-modified analogues of 1α,25-dihydroxyergocalciferol is disclosed in Kutner et al., *The Journal of Organic Chemistry*, 1988, 53:3450–3457. In addition, the preparation of 24-homo and 26-homo vitamin D analogs are disclosed in U.S. Pat. No. 4,717,721, the description of which is incorporated herein by reference.

The enantioselective synthesis of chiral molecules is now state of the art. Through combinations of enantioselective synthesis and purification techniques, many chiral molecules can be synthesized as an enantiomerically enriched preparation. For example, methods have been reported for the enantioselective synthesis of A-ring diastereomers of 1α,25 (OH)$_2$D3 as described in Muralidharan et al. (1993) *J. Organic Chem.* 58(7): 1895–1899 and Norman et al. (1993) *J. Biol. Chem.* 268(27): 20022–30. Other methods for the enantiomeric synthesis of various compounds known in the art include, inter alia, epoxides (see, e.g., Johnson, R. A.; Sharpless, K. B. In *Catalytic Asymmetric Synthesis*; Ojima, I., Ed.: VCH: New York, 1993; Chapter 4.1. Jacobsen, E. N. Ibid. Chapter 4.2), diols (e.g., by the method of Sharpless, *J. Org. Chem.* (1992) 57:2768), and alcohols (e.g., by reduction of ketones, E. J. Corey et al., *J. Am. Chem. Soc.* (1987) 109:5551). Other reactions useful for generating optically enriched products include hydrogenation of olefins (e.g., M. Kitamura et al., *J. Org. Chem.* (1988) 53:708); Diels-Alder reactions (e.g., K. Narasaka et al., *J. Am. Chem. Soc.* (1989) 111:5340); aldol reactions and alkylation of enolates (see, e.g., D. A. Evans et al., *J. Am. Chem. Soc.* (1981) 103:2127; D. A. Evans et al., *J. Am. Chem. Soc.* (1982) 104:1737); carbonyl additions (e.g., R. Noyori, *Angew. Chem. Int. Ed. Eng.* (1991) 30:49); and ring-opening of meso-epoxides (e.g., Martinez, L. E.; Leighton J. L., Carsten, D. H.; Jacobsen, E. N. *J. Am. Chem. Soc.* (1995) 117:5897–5898). The use of enymes to produce optically enriched products is also well known in the art (e.g., M. P. Scheider, ed. "Enzymes as Catalysts in Organic Synthesis", D. Reidel, Dordrecht (1986).

Chiral synthesis can result in products of high stereoisomer purity. However, in some cases, the stereoisomer purity of the product is not sufficiently high. The skilled artisan will appreciate that the separation methods described herein can be used to further enhance the stereoisomer purity of the vitamin D3-epimer obtained by chiral synthesis.

Separation of isomers can be accomplished in several ways known in the art. An exemplary straight phase and reverse phase HPLC system used to separate natural or synthetic diastereomers of 1α,25(OH)$_2$D3 is detailed in the appended example and illustrated in FIG. 2. Further methods for separating a racemic mixture of two enantiomers include chromatography using a chiral stationary phase (see, e.g., "Chiral Liquid Chromatography", W. J. Lough, Ed. Chapman and Hall, New York (1989)). Enantiomers can also be separated by classical resolution techniques. For example, formation of diastereomeric salts and fractional crystallization can be used to separate enantiomers. For the separation of enantiomers of carboxylic acids, the diastereomeric salts can be formed by addition of enantiomerically pure chiral bases such as brucine, quinine, ephedrine, strychnine, and the like. Alternatively, diastereomeric esters can be formed with enantiomerically pure chiral alcohols such as menthol, followed by separation of the diastereomeric esters and hydrolysis to yield the free, enantiomerically enriched carboxylic acid. For separation of the optical isomers of amino compounds, addition of chiral carboxylic or sulfonic acids, such as camphorsulfonic acid, tartaric acid, mandelic acid, or lactic acid can result in formation of the diastereomeric salts.

Pharmaceutical Compositions

In another aspect, the present invention provides pharmaceutically acceptable compositions which comprise a therapeutically-effective amount of one or more of the isolated vitamin D$_3$ compounds of formulas I and II, formulated together with one or more pharmaceutically acceptable carrier(s).

In a preferred embodiment, these pharmaceutical compositions are suitable for topical or oral administration to a subject. In other embodiments, as described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes; (2) parenteral administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream or foam; or (5) aerosol, for example, as an aqueous aerosol, liposomal preparation or solid particles containing the compound.

In certain embodiments, the subject is a mammal, e.g., a primate, e.g., a human. As used herein, the language "subject" is intended to include human and non-human animals. Preferred human animals include a human patient having a disorder characterized by the aberrant activity of a vitamin $D_3$-responsive cell. The term "non-human animals" of the invention includes all vertebrates, e.g., mammals and non-mammals, such as non-human primates, sheep, dog, cow, chickens, amphibians, reptiles, etc.

The phrase "therapeutically-effective amount" as used herein means that amount of a vitamin $D_3$ compound(s) of formulas I and II, or composition comprising such a compound which is effective for the compound to produce its intended function, e.g., the modulation of activity of a vitamin $D_3$-response cell. The effective amount can vary depending on such factors as the type of cell growth being treated or inhibited, the particular type of vitamin $D_3$ compound, the size of the subject, or the severity of the undesirable cell growth or activity. One of ordinary skill in the art would be able to study the aforementioned factors and make the determination regarding the effective amount of the vitamin $D_3$ compound of formulas I and II without undue experimentation.

In certain embodiments, one or more vitamin $D_3$ compounds as represented by formulas I and II may be administered alone, or as part of combinatorial therapy. For example, the vitamin $D_3$ compounds can be conjointly administered with one or more agents such as mitotic inhibitors, alkylating agents, antimetabolites, nucleic acid, intercalating agents, topoisomerase inhibitors, agents which promote apoptosis, and/or agents which modulate immune responses. The effective amount of vitamin $D_3$ compound used can be modified according to the concentrations of the other agents used.

In vitro assay using keratinocytes or parathyroid cells, or an assay similar thereto (e.g., differing in choice of cells, e.g., bone cells, intestinal cells, neoplastic cells) can be used to determine an "effective amount" of the vitamin $D_3$ compounds of formulas I and II, or combinations thereof. The ordinarily skilled artisan would select an appropriate amount of each individual compound in the combination for use in the aforementioned in vitro assay or similar assays. Changes in cell activity or cell proliferation can be used to determine whether the selected amounts are "effective amount" for the particular combination of compounds. The regimen of administration also can affect what constitutes an effective amount. As described in detail below, vitamin $D_3$ compounds of formulas I and II can be administered to the subject prior to, simultaneously with, or after the administration of the other agent(s). Further, several divided dosages, as well as staggered dosages, can be administered daily or sequentially, or the dose can be proportionally increased or decreased as indicated by the exigencies of the therapeutic situation.

The phrase "pharmaceutically acceptable" is employed herein to refer to those vitamin $D_3$ compounds of formulas I and II, compositions containing such compounds, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the subject chemical from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Compositions containing the vitamin $D_3$ compounds of the present invention include those suitable for oral, nasal, topical (including buccal and sublingual), rectal, vaginal, aerosol and/or parenteral administration. The compositions may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred per cent, this amount will range from about 1 per cent to about ninety-nine percent of active ingredient, preferably from about 5 per cent to about 70 per cent, most preferably from about 10 per cent to about 30 per cent.

Methods of preparing these compositions include the step of bringing into association a vitamin $D_3$ compound(s) of formulas I and II with the carrier and, optionally, one or more accessory ingredients. In general, the formulations are prepared by uniformly and intimately bringing into association a vitamin $D_3$ compound with liquid carriers, or finely divided solid carriers, or both, and then, if necessary, shaping the product.

Compositions of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a vitamin $D_3$ compound(s) of formulas I and II as an active ingredient. A compound may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered peptide or peptidomimetic moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the vitamin $D_3$ compound(s) of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active vitamin $D_3$ compound(s) may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Pharmaceutical compositions of the invention for rectal or vaginal administration may be presented as a suppository, which may be prepared by mixing one or more vitamin $D_3$ compound(s) of formulas I and II with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent.

Compositions of the present invention which are suitable for vaginal administration also include pessaries, tampons, creams, gels, pastes, foams or spray formulations containing such carriers as are known in the art to be appropriate.

Dosage forms for the topical or transdermal administration of a vitamin $D_3$ compound(s) of formulas I and II include powders, sprays, ointments, pastes, creams, lotions, gels, solutions, patches and inhalants. The active vitamin $D_3$ compound may be mixed under sterile conditions with a pharmaceutically-acceptable carrier, and with any preservatives, buffers, or propellants which may be required.

The ointments, pastes, creams and gels may contain, in addition to vitamin $D_3$ compound(s) of formulas I and II, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a vitamin $D_3$ compound(s) of formulas I and II, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The vitamin $D_3$ compound(s) of formulas I and II can be alternatively administered by aerosol. This is accomplished by preparing an aqueous aerosol, liposomal preparation or solid particles containing the compound. A nonaqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Transdermal patches have the added advantage of providing controlled delivery of a vitamin $D_3$ compound(s) of formulas I and II to the body. Such dosage forms can be made by dissolving or dispersing the agent in the proper medium. Absorption enhancers can also be used to increase the flux of the peptidomimetic across the skin. The rate of such flux can be controlled by either providing a rate controlling membrane or dispersing the peptidomimetic in a polymer matrix or gel.

Ophthalmic formulations, eye ointments, powders, solutions and the like, are also contemplated as being within the scope of this invention.

Pharmaceutical compositions of this invention suitable for parenteral administration comprise one or more vitamin $D_3$ compound(s) of formulas I and II in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of vitamin $D_3$ compound(s) of formulas I and II in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly (anhydrides). Depot injectable formulations are also prepared by entrapping the drug in liposomes or microemulsions which are compatible with body tissue.

When the vitamin $D_3$ compound(s) of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

The term "administration," is intended to include routes of introducing a subject the 3-epimer vitamin $D_3$ compound of formula I to perform their intended function. Examples of routes of administration which can be used include injection (subcutaneous, intravenous, parenterally, intraperitoneally, intrathecal, etc.), oral, inhalation, rectal and transdermal. The pharmaceutical preparations are of course given by forms suitable for each administration route. For example, these preparations are administered in tablets or capsule form, by injection, inhalation, eye lotion, ointment, suppository, etc. administration by injection, infusion or inhalation; topical by lotion or ointment; and rectal by suppositories. Oral administration is preferred. The injection can be bolus or can be continuous infusion. Depending on the route of administration, the vitamin $D_3$ compound of formulas I and II can be coated with or disposed in a selected material to protect it from natural conditions which may detrimentally effect its ability to perform its intended function. The vitamin $D_3$ compound of formulas I and II can be administered alone, or in conjunction with either another agent as described above or with a pharmaceutically acceptable carrier, or both. The vitamin $D_3$ compound can be administered prior to the administration of the other agent, simultaneously with the agent, or after the administration of the agent. Furthermore, the vitamin $D_3$ compound of formulas I and II can also be administered in a proform which is converted into its active metabolite, or more active metabolite in vivo.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrastemal injection and infusion.

The phrases "systemic administration," "administered systemically", "peripheral administration" and "administered peripherally" as used herein mean the administration of a vitamin $D_3$ compound(s) of formulas I and II, such that it enters the patient's system and, thus, is subject to metabolism and other like processes, for example, subcutaneous administration.

These vitamin $D_3$ compound(s) of formulas I and II may be administered to a "subject", e.g., mammals, e.g., humans and other animals. Administration can be carried out by any suitable route of administration, including orally, nasally, as by, for example, a spray, rectally, intravaginally, parenterally, intracisternally and topically, as by powders, ointments or drops, including buccally and sublingually.

Regardless of the route of administration selected, the vitamin $D_3$ compound(s) of formulas I and II, which may be used in a suitable hydrated form, and/or the pharmaceutical compositions of the present invention, are formulated into pharmaceutically-acceptable dosage forms by conventional methods known to those of skill in the art.

Actual dosage levels and time course of administration of the active ingredients in the pharmaceutical compositions of this invention may be varied so as to obtain an amount of the active ingredient which is effective to achieve the desired therapeutic response for a particular patient, composition, and mode of administration, without being toxic to the patient. Exemplary dose range is from 0.1 to 10 μg per day.

Uses of the Vitamin D Compounds of the Invention

Another aspect of the invention pertains to isolated vitamin $D_3$ compounds of formulas I and II having at least one biological activity of vitamin $D_3$, and having improved biological properties when administered into a subject than vitamin $D_3$ under the same conditions, as well as, methods of testing and using these compounds to treat disorders involving an aberrant activity of a vitamin D3-responsive cell, e.g., neoplastic cells, hyperproliferative skin cells, parathyroid cells, immune cells and bone cells, among others.

The language "biological activities" of vitamin $D_3$ is intended to include all activities elicited by vitamin $D_3$ compounds of formulas I and II in a responsive cell. This term includes genomic and non-genomic activities elicited by these compounds (Bouillon, R. et al. (1995) *Endocrinology Reviews* 16(2):206–207; Norman A. W. et al. (1992) *J. Steroid Biochem Mol. Biol* 41:231–240; Baran D. T. et al. (1991) *J. Bone Miner Res.* 6:1269–1275; Caffrey J. M. and Farach-Carson M. C. (1989) *J. Biol. Chem.* 264:20265–20274; Nemere I. et al. (1984) *Endocrinology* 115:1476–1483).

As used herein, the term "vitamin $D_3$-responsive cell" includes any cell which is is capable of responding to a vitamin $D_3$ compound having the formula I or II, and is associated with disorders involving an aberrant activity of hyperproliferative skin cells, parathyroid cells, neoplastic cells, immune cells, and bone cells. These cells can respond to vitamin $D_3$ activation by triggering genomic and/or non-genomic responses that ultimately result in the modulation of cell proliferation, differentiation survival, and/or other cellular activities such as hormone secretion. In a preferred embodiment, the ultimate responses of a cell are inhibition of cell proliferation and/or induction of differentiation-specific genes. Exemplary vitamin $D_3$ responsive cells include immune cells, bone cells, neuronal cells, endocrine cells, neoplastic cells, epidermal cells, endodermal cells, smooth muscle cells, among others.

As used herein, the language "vitamin $D_3$ agonist" refers to a compound which potentiates, induces or otherwise enhances a biological activity of vitamin $D_3$ in a responsive cell. In certain embodiments, an agonist may induce a genomic activity, e.g., activation of transcription by a vitamin $D_3$ nuclear receptor, or a non-genomic vitamin $D_3$ activity, e.g., potentiation of calcium channel activity. In other embodiments, the agonist potentiates the sensitivity of the receptor to another vitamin $D_3$ compound, e.g., treatment with the agonist lowers the concentration of vitamin $D_3$ compound required to induce a particular biological response. The language "vitamin $D_3$ antagonist" is intended to include those compounds that oppose any biological activity of a vitamin $D_3$ compound.

The language "non-genomic" vitamin $D_3$ activities include cellular (e.g., calcium transport across a tissue) and subcellular activities (e.g., membrane calcium transport opening of voltage-gated calcium channels, changes in intracellular second messengers) elicited by vitamin $D_3$ compounds in a responsive cell. Electrophysiological and biochemical techniques for detecting these activities are known in the art. An example of a particular well-studied non-genomic activity is the rapid hormonal stimulation of intestinal calcium mobilization, termed "transcaltachia" (Nemere I. et al. (1984) *Endocrinology* 115:1476–1483; Lieberherr M. et al. (1989) *J. Biol. Chem.* 264:20403–20406; Wali R. K. et al. (1992) *Endocrinology* 131:1125–1133; Wali R. K. et al. (1992) *Am. J. Physiol.* 262:G945–G953; Wali R. K. et al. (1990) *J. Clin. Invest.* 85:1296–1303; Bolt M. J. G. et al. (1993) *Biochem. J.* 292:271–276). Detailed descriptions of experimental transcaltachia are provided in Norman, A. W. (1993) *Endocrinology* 268(27):20022–20030; Yoshimoto, Y. and Norman, A. W. (1986) *Endocrinologyl* 18:2300–2304. Changes in calcium activity and second messenger systems are well known in the art and are extensively reviewed in Bouillion, R. et al. (1995) *Endocrinology Review* 16(2): 200–257; the description of which is incorporated herein by reference.

Exemplary systems and assays for testing non-genomic activity are extensively described in the following references, liver (Baran D. T. et al. (1989) *FEBS Lett* 259:205–208; Baran D. T. et al. (1990) *J. Bone Miner Res.* 5:517–524; rat osteoblasts, e.g., ROS 17/2.8 cells (Baran D. T. et al. (1991) *J. Bone Miner Res.* 6:1269–1275; Caffrey J. M. (1989) *J. Biol. Chem.* 264:20265–20274; Civitelli R. et al. (1990) *Endocrinology* 127:2253–2262), muscle (DeBoland A. R. and Boland R. L. (1993) *Biochem. Biophys Acta Mol. Cell Res.* 1179:93–104; Morelli S. et al. (1993) *Biochem J.* 289:675–679; Selles J. and Boland R. L. (1991) *Mol. Cell Endocrinol.* 82:229–235), and in parathyroid cells (Bourdeau A. et al. (1990) *Endocrinology* 127:2738–2743).

The language "genomic" activities or effects of vitamin $D_3$ is intended to include those activities mediated by the nuclear/cytosol receptor for $1\alpha,25(OH)_2$ $D_3$ (VD3R), e.g., transcriptional activation of target genes. The term "VD3Rs" is intended to include members of the type II class of steroid/thyroid superfamily of receptors (Stunnenberg, H. G. (1993) *Bio Essays* 15(5):309–15), which are able to bind transactivate through the vitamin D response element (VDRE) in the absence of a ligand (Damm et al. (1989) *Nature* 339:593–97; Sap et al. *Nature* 343:177–180). As used herein "VDREs" refer to a DNA sequences composed of half-sites arranged as direct repeats. It is known in the art that type II receptors do not bind to their respective binding site as homodimers but require an auxiliary factor, RXR (e.g. RXRα, RXRβ, RXRγ) for high affinity binding Yu et al. (1991) *Cell* 67:1251–1266; Bugge et al. (1992) *EMBO J.* 11:1409–1418; Kliewer et al. (1992) *Nature* 355:446–449; Leid et al. (1992) *EMBO J.* 11:1419–1435; Zhang et al. (1992) *Nature* 355:441–446).

Following binding, the transcriptional activity of a target gene (i.e., a gene associated with the specific DNA sequence) is enhanced as a function of the ligand bound to the receptor heterodimer. Exemplary vitamin $D_3$-responsive genes include osteocalcin, osteopontin, calbindins, parathyroid hormone (PTH), 24-hydroxylase, and $α_v, β_3$-integrin. Genomic activities elicited by vitamin D3 compounds can be tested by detecting the transcriptional upregulation of a vitamin $D_3$ responsive gene in a cell containing $VD3R_S$. For example, the steady state levels of responsive gene mRNA or protein, e.g. calbindin gene, osteocalcin gene, can be detected in vivo or in vitro. Suitable cells that can be used include any vitamin D3-responsive cell, e.g., keratinocytes, parathyroid cells, MG-63 cell line, among others.

In accordance with a still further embodiment of the present invention, convenient screening methods can be established in cell lines containing $VD_3R_S$, comprising (i) establishing a culture of these cells which include a reporter gene construct having a reporter gene which is expressed in an $VD_3R$-dependent fashion; (ii) contacting these cells with vitamin D3 compounds of formulas I and II; and (iii) monitoring the amount of expression of the reporter gene. Expression of the reporter gene reflects transcriptional activity of the VD$_3$R$_S$ protein. Typically, the reporter gene construct will include a reporter gene in operative linkage with one or more transcriptional regulatory elements responsive to VD$_3$R$_S$, e.g., the VD$_3$R$_S$ response element (VDRE) known in the art. The amount of transcription from the reporter gene may be measured using any method known to those of skill in the art to be suitable. For example, specific mRNA expression may be detected using Northern blots or specific protein product may be identified by a characteristic stain, immunoassay or an intrinsic activity. In preferred embodiments, the gene product of the reporter is detected by an intrinsic activity associated with that product. For instance, the reporter gene may encode a gene product that, by enzymatic activity, gives rise to a detection signal based on color, fluorescence, or luminescence. The amount of expression from the reporter gene is then compared to the amount of expression in either the same cell in the absence of the test compound or it may be compared with the amount of transcription in a substantially identical cell that lacks the specific receptors. Agonistic vitamin D$_3$ compounds can then be readily detected by the increased activity or concentration of these reporter genes relative to untransfected controls.

After identifying certain test compounds as potential agonists or antagonists of vitamin D$_3$ compounds, the practioner of the subject assay will continue to test the efficacy and specificity of the selected compounds both in vitro and in vivo. Whether for subsequent in vivo testing, or for administration to an animal as an approved drug, agents identified in the subject assay can be formulated in pharmaceutical preparations, such as described above, for in vivo administration to an animal, preferably a human.

As described herein, the vitamin D3 compounds of the present invention show improved biological properties than vitamin D3. As used herein, the language "improved biological properties" refers to any activity inherent in a vitamin D3 compound of formula I or II that enhances its effectiveness in vivo. In a preferred embodiment, this term refers to any qualitative or quantitative improved therapeutic property of a vitamin D$_3$ compound, such as enhanced stability in vivo and/or reduced toxicity, e.g., reduced hypercalcemic activity. The improved biological property may occur in both a tissue-specific and non-specific manner. For example, certain tissues may be capable of metabolizing vitamin D$_3$ into unique metabolites that enhance in a tissue-specific manner the biological activities of this compound.

The increased stability of the vitamin D3 compounds of formulas I and II can be demonstated in incubation studies, wherein a significantly higher concentration of the such vitamin D3 after prolonged incubations in vivo or in vitro, or an increase in the binding to plasma vitamin D binding protein (DBP) compared to vitamin D3 indicates a compound having enhanced stability (See A. W. Norman et al. *J. Biol. Chem.* 268 (27): 20022–20030).

The language "reduced toxicity" is intended to include a reduction in any undesired side effect elicited by a vitamin D3 compound of formula I or II when administered in vivo, e.g., a reduction in the hypercalcemic activity. The language "hypercalcemia" or "hypercalcemic activity" is intended to have its accepted clinical meaning, namely, increases in calcium serum levels that are manifested in a subject by the following side effects, depression of central and peripheral nervous system, muscular weakness, constipation, abdominal pain, lack of appetite and, depressed relaxation of the heart during diastole. Symptomatic manifestations of hypercalcemia are triggered by a stimulation of at least one of the following activities, intestinal calcium transport, bone calcium metabolism and osteocalcin synthesis (reviewed in Boullion, R. et al. (1995) *Endocrinology Reviews* 16(2): 200–257).

Compounds exhibiting reduced hypercalcemic activity can be tested in vivo or in vitro using methods known in the art and reviewed by Boullion, R. et al. (1995) *Endocrinology Reviews* 16(2): 200–257. For example, the serum calcium levels following administration of a vitamin D3 compounds of formula I or II can be tested by routine experimentation (Lemire, J. M. (1994) *Endocrinology* 135(6):2818–2821). Briefly, vitamin D3 compounds of formulas I and II can be administered intramuscularly to vitamin D$_3$-deficient subjects, e.g., rodents, e.g. mouse, or avian species, e.g. chick. At appropriate time intervals, serum calcium levels and extent of calcium uptake can be used to determine the level of bone calcium mobilization (BCM) and intestinal calcium absorption (ICA) induced by the tested vitamin D$_3$ compound as described in Norman, A. W. et al. (1993) *J. Biol. Chem.* 268(27):20022–20029. Compounds which upon addition fail to increase the concentration of calcium in the blood serum, thus showing decreased BCM and ICA responses compared to their isomeric counterparts, are considered to have reduced hypercalcemic activity. Compounds which have reduced toxicity compared to their isomeric counterparts are considered to have reduced toxicity. Additional calcium homeostasis-related assays are described below in the Calcium and Phosphate Homeostasis section.

Hyperproliferative Conditions

In another aspect the present invention provides a method of treating in a subject, a disorder characterized by aberrant activity of a vitamin D3-responsive cell. The method involves administering to the subject an effective amount of a pharmaceutical composition of a vitamin D3 compound of formula I or II such that the activity of the cell is modulated. As used herein, the language "modulate" refers to increases or decreases in the activity of a cell in response to exposure to a compound of the invention, e.g., the inhibition of proliferation and/or induction of differentiation of at least a sub-population of cells in an animal such that a desired end result is achieved, e.g. a therapeutic result. In preferred embodiments, this phrase is intended to include hyperactive conditions that result in pathological disorders.

In certain embodiments, the cells to be treated are hyperproliferative cells. As described in greater detail below, the vitamin D3 compounds of formulas I and II can be used to inhibit the proliferation of a variety of hyperplastic and neoplastic tissues. In accordance with the present invention, vitamin D3 compounds of formulas I and II can be used in the treatment of both pathologic and non-pathologic proliferative conditions characterized by unwanted growth of vitamin D3-responsive cells, e.g., hyperproliferative skin cells, immune cells, and tissue having transformed cells, e.g., such as carcinomas, sarcomas and leukemias. In other embodiments, the cells to be treated are aberrant secretory cells, e.g., parathyroid cells, immune cells.

As used herein, the terms "hyperproliferative" and "neoplastic" are used interchangeably, and include those cells having the capacity for autonomous growth, i.e., an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness.

"Pathologic hyperproliferative" cells occur in disease states characterized by malignant tumor growth. Examples of non-pathologic hyperproliferative cells include proliferation of cells associated with wound repair.

The use of vitamin D3 compounds of formulas I and II in treating hyperproliferative conditions has been limited because of their hypercalcemic effects. Thus, vitamin D3 compounds of formula I and II can provide a less toxic alternative to current methods of treatment.

In one embodiment, this invention features a method for inhibiting the proliferation and/or inducing the differentiation of a hyperproliferative skin cell, e.g., an epidermal or an epithelial cell, e.g. a keratinocytes, by contacting the cells with a vitamin D3 compound of formula I or II. In general, the method includes a step of contacting a pathological or non-pathological hyperproliferative cell with an effective amount of such vitamin D3 compound to promote the differentiation of the hyperproliferative cells The present method can be performed on cells in culture, e.g. in vitro or ex vivo, or can be performed on cells present in an animal subject, e.g., as part of an in vivo therapeutic protocol. The therapeutic regimen can be carried out on a human or any other animal subject.

The vitamin D3 compounds of the present invention can be used to treat a hyperproliferative skin disorder. Exemplary disorders include, but are not limited to, psoriasis, basal cell carcinoma, keratinization disorders and keratosis. Additional examples of these disorders include eczema; lupus associated skin lesions; psoriatic arthritis; rheumatoid arthritis that involves hyperproliferation and inflammation of epithelial-related cells lining the joint capsule; dermatitides such as seborrheic dermatitis and solar dermatitis; keratoses such as seborrheic keratosis, senile keratosis, actinic keratosis. photo-induced keratosis, and keratosis follicularis; acne vulgaris; keloids and prophylaxis against keloid formation; nevi; warts including verruca, condyloma or condyloma acuminatum, and human papilloma viral (HPV) infections such as venereal warts; leukoplakia; lichen planus; and keratitis.

In an illustrative example, vitamin D3 compounds of formulas I and II can be used to inhibit the hyperproliferation of keratinocytes in treating diseases such as psoriasis by administering an effective amount of these compounds to a subject in need of treatment. The term "psoriasis" is intended to have its medical meaning, namely, a disease which afflicts primarily the skin and produces raised, thickened, scaling, nonscarring lesions. The lesions are usually sharply demarcated erythematous papules covered with overlapping shiny scales. The scales are typically silvery or slightly opalescent. Involvement of the nails frequently occurs resulting in pitting, separation of the nail, thickening and discoloration. Psoriasis is sometimes associated with arthritis, and it may be crippling. Hyperproliferation of keratinocytes is a key feature of psoriatic epidermal hyperplasia along with epidermal inflammation and reduced differentiation of keratinocytes. Multiple mechanisms have been invoked to explain the keratinocyte hyperproliferation that characterizes psoriasis. Disordered cellular immunity has also been implicated in the pathogenesis of psoriasis.

Pharmaceutical compositions of vitamin D3 compounds of formulas I and II can be delivered or administered topically or by transdermal patches for treating dermal psoriasis. Alternatively, oral administration is used. Additionally, the compositions can be delivered parenterally, especially for treatment of arthritis, such as psoriatic arthritis, and for direct injection of skin lesions. Parenteral therapy is typically intra-dermal, intra-articular, intramuscular or intravenous. A preferred way to practice the invention is to apply the vitamin D3 compounds of formulas I and II, in a cream or oil based carrier, directly to the psoriatic lesions. Typically, the concentration of the vitamin D3 compound in a cream or oil is 1–2%. Alternatively, an aerosol can be used topically. These compounds can also be orally administered.

In general, the route of administration is topical (including administration to the eye, scalp, and mucous membranes), oral, or parenteral. Topical administration is preferred in treatment of skin lesions, including lesions of the scalp, lesions of the cornea (keratitis), and lesions of mucous membranes where such direct application is practical. Shampoo formulations are sometimes advantageous for treating scalp lesions such as seborrheic dermatitis and psoriasis of the scalp. Mouthwash and oral paste formulations can be advantageous for mucous membrane lesions, such as oral lesions and leukoplakia. Oral administration is a preferred alternative for treatment of skin lesions and other lesions discussed above where direct topical application is not as practical, and it is a preferred route for other applications.

Intra-articular injection is a preferred alternative in the case of treating one or only a few (such as 2–6) joints. Additionally, the therapeutic compounds are injected directly into lesions (intra-lesion administration) in appropriate cases. Intra-dermal administration is an alternative for dermal lesions such as those of psoriasis.

The amount of the pharmaceutical composition to be administered varies depending upon the type of the disease of a patient, the severity of the disease, the type of the active vitamin $D_3$ compound of Formulas I or II, among others. For example, the vitamin D3 compound of formula I or II can be administered topically for treating hyperproliferative skin conditions at a dose in the range of 1 to 1000 $\mu$g per gram of topical formulation.

Neoplasia

Another embodiment features methods for inhibiting the proliferation and/or reversing the transformed phenotype of vitamin D3-responsive hyperproliferative cells by contacting the cells with a vitamin D3 compound of formula I or II. In general, the method includes a step of contacting pathological or non-pathological hyperproliferative cells with an effective amount of a vitamin D3 compound of formula I or II for promoting the differentiation of the hyperproliferative cells. The present method can be performed on cells in culture, e.g., in vitro or ex vivo, or can be performed on cells present in an animal subject, e.g., as part of an in vivo therapeutic protocol. The therapeutic regimen can be carried out on a human or other animal subject.

The terms "antineoplastic agent" and "antiproliferative agent" are used interchangeably herein and includes agents that have the functional property of inhibiting the proliferation of a vitamin D3-responsive cells, e.g., inhibit the development or progression of a neoplasm having such a characteristic, particularly a hematopoietic neoplasm.

As used herein, a "therapeutically effective antineoplastic amount" of a vitamin D3 compound of formula I or II refers to an amount of an agent which is effective, upon single or multiple dose administration to the patient, in inhibiting the growth of a neoplastic vitamin D3-responsive cells, or in prolonging the survivability of the-patient with such neoplastic cells beyond that expected in the absence of such treatment. As used herein, "inhibiting the growth" of the neoplasm includes the slowing, interrupting, arresting or stopping its growth and metastases and does not necessarily indicate a total elimination of the neoplastic growth.

As used herein, "a prophylactically effective antineoplastic amount" of a compound refers to an amount of a vitamin D3 compound of formula I or II which is effective, upon single or multiple dose administration to the patient, in preventing or delaying the occurrence of the onset of a neoplastic disease state.

The common medical meaning of the term "neoplasia" refers to "new cell growth" that results as a loss of responsiveness to normal growth controls, e.g. to neoplastic cell growth. A "hyperplasia" refers to cells undergoing an abnormally high rate of growth. However, as used herein, the terms neoplasia and hyperplasia can be used interchangably, as their context will reveal, referring to generally to cells experiencing abnormal cell growth rates. Neoplasias and hyperplasias include "tumors," which may be either benign, premalignant or malignant.

The vitamin D3 compounds of formulas I and II can be tested initially in vitro for their inhibitory effects in the proliferation of neoplastic cells. Examples of cell lines that can be used are transformed cells, e.g., the human promyeloid leukemia cell line HL-60, and the human myeloid leukemia U-937 cell line (Abe E. et al. (1981) *Proc. Natl. Acad. Sci. USA* 78:4990–4994; Song L. N. and Cheng T. (1992) *Biochem Pharmacol* 43:2292–2295; Zhou J. Y. et al. (1989) Blood 74:82–93; U.S. Pat. Nos. 5,401,733, U.S. 5,087,619). Alternatively, the antitumoral effects of vitamin D3 compounds of formulas I and II can be tested in vivo using various animal models known in the art and summarized in Bouillon, R. et al. (1995) *Endocrine Reviews* 16(2):233 (Table E), which is incorporated by reference herein. For example, SL mice are routinely used in the art to test vitamin D3 compounds of formulas I and II as models for MI myeloid leukemia (Honma et al. (1983) *Cell Biol.* 80:201–204; Kasukabe T. et al. (1987) *Cancer Res.* 47:567–572); breast cancer studies can be performed in, for example, nude mice models for human MX1 (ER) (Abe J. et al. (1991) *Endocrinology* 129:832–837; other cancers, e.g., colon cancer, melanoma osteosarcoma, can be characterized in, for example, nude mice models as describe in (Eisman J. A. et al. (1987) *Cancer Res.* 47:21–25; Kawaura A. et al. (1990) *Cancer Lett* 55:149–152; Belleli A. (1992) *Carcinogenesis* 13:2293–2298; Tsuchiya H. et al. (1993) *J. Orthopaed Res.* 11:122–130).

The subject method may also be used to inhibit the proliferation of hyperplastic/neoplastic cells of hematopoietic origin, e.g., arising from myeloid, lymphoid or erythroid lineages, or precursor cells thereof. For instance, the present invention contemplates the treatment of various myeloid disorders including, but not limited to, acute promyeloid leukemia (APML), acute myelogenous leukemia (AML) and chronic myelogenous leukemia (CML) (reviewed in Vaickus, L. (1991) *Crit Rev. in Oncol./Hemotol.* 11:267–97). Lymphoid malignancies which may be treated by the subject method include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas contemplated by the treatment method of the present invention include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF) and Hodgkin's disease.

The term "leukemia" is intended to have its clinical meaning, namely, a neoplastic disease in which white corpuscle maturation is arrested at a primitive stage of cell development. The disease is characterized by an increased number of leukemic blast cells in the bone marrow, and by varying degrees of failure to produce normal hematopoietic cells. The condition may be either acute or chronic. Leukemias are further typically categorized as being either lymphocytic i.e., being characterized by cells which have properties in common with normal lymphocytes, or myelocytic (or myelogenous), i.e., characterized by cells having some characteristics of normal granulocytic cells. Acute lymphocytic leukemia ("ALL") arises in lymphoid tissue, and ordinarily first manifests its presence in bone marrow. Acute myelocytic leukemia ("AML") arises from bone marrow hematopoietic stem cells or their progeny. The term acute myelocytic leukemia subsumes several subtypes of leukemia: myeloblastic leukemia, promyelocytic leukemia, and myelomonocytic leukemia. In addition, leukemias with erythroid or megakaryocytic properties are considered myelogenous leukemias as well.

As used herein the term "leukemic cancer" refers to all cancers or neoplasias of the hemopoietic and immune systems (blood and lymphatic system). The acute and chronic leukemias, together with the other types of tumors of the blood, bone marrow cells (myelomas), and lymph tissue (lymphomas), cause about 10% of all cancer deaths and about 50% of all cancer deaths in children and adults less than 30 years old. Chronic myelogenous leukemia (CML), also known as chronic granulocytic leukemia (CGL), is a neoplastic disorder of the hematopoietic stem cell. The term "leukemia" is art recognized and refers to a progressive, malignant disease of the blood-forming organs, marked by distorted proliferation and development of leukocytes and their precursors in the blood and bone marrow.

In certain embodiments, the vitamin D3 compounds of formulas I and II can be used in combinatorial therapy with conventional cancer chemotherapeutics. Conventional treatment regimens for leukemia and for other tumors include radiation, drugs, or a combination of both. In addition to radiation, the following drugs, usually in combinations with each other, are often used to treat acute leukemias: vincristine, prednisone, methotrexate, mercaptopurine, cyclophosphamide, and cytarabine. In chronic leukemia, for example, busulfan, melphalan, and chlorambucil can be used in combination. All of the conventional anti-cancer drugs are highly toxic and tend to make patients quite ill while undergoing treatment. Vigorous therapy is based on the premise that unless every leukemic cell is destroyed, the residual cells will multiply and cause a relapse.

The subject method can also be useful in treating malignancies of the various organ systems, such as affecting lung, breast, lymphoid, gastrointestinal, and genito-urinary tract as well as adenocarcinomas which include malignancies such as most colon cancers, renal-cell carcinoma, prostate cancer and/or testicular tumors, non-small cell carcinoma of the lung, cancer of the small intestine and cancer of the esophagus.

The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures.

The term "sarcoma" is art recognized and refers to malignant tumors of mesenchymal derivation.

According to the general paradigm of vitamin D3 involvement in differentiation of transformed cells, exemplary solid tumors that can be treated according to the method of the present invention include vitamin D3-responsive phenotypes of sarcomas and carcinomas such as, but not limited to: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma.

Determination of a therapeutically effective antineoplastic amount or a prophylactically effective antineoplastic amount of the vitamin D3 compound of formula I or II, can be readily made by the physician or veterinarian (the "attending clinician"), as one skilled in the art, by the use of known techniques and by observing results obtained under analogous circumstances. The dosages may be varied depending upon the requirements of the patient in the judgment of the attending clinician, the severity of the condition being treated and the particular compound being employed. In determining the therapeutically effective antineoplastic amount or dose, and the prophylactically effective antineoplastic amount or dose, a number of factors are considered by the attending clinician, including, but not limited to: the specific hyperplastic/neoplastic cell involved; pharmacodynamic characteristics of the particular agent and its mode and route of administration; the desirder time course of treatment; the species of mammal; its size, age, and general health; the specific disease involved; the degree of or involvement or the severity of the disease; the response of the individual patient; the particular compound administered; the mode of administration; the bioavailability characteristics of the preparation administered; the dose regimen selected; the kind of concurrent treatment (i.e., the interaction of the vitamin D3 compounds of formulas I and II with other coadministered therapeutics); and other relevant circumstances. U.S. Pat. No. 5,427,916, for example, describes method for predicting the effectiveness of antineoplastic therapy in individual patients, and illustrates certain methods which can be used in conjunction with the treatment protocols of the instant invention.

Treatment can be initiated with smaller dosages which are less than the optimum dose of the compound. Thereafter, the dosage should be increased by small increments until the optimum effect under the circumstances is reached. For convenience, the total daily dosage may be divided and administered in portions during the day if desired. A therapeutically effective antineoplastic amount and a prophylactically effective anti-neoplastic amount of a vitamin D3 compound of formula I or II is expected to vary from about 0.1 milligram per kilogram of body weight per day (mg/kg/day) to about 100 mg/kg/day.

Compounds which are determined to be effective for the prevention or treatment of tumors in animals, e.g., dogs, rodents, may also be useful in treatment of tumors in humans. Those skilled in the art of treating tumor in humans will know, based upon the data obtained in animal studies, the dosage and route of administration of the compound to humans. In general, the dosage and route of administration in humans is expected to be similar to that in animals.

The identification of those patients who-are in need of prophylactic treatment for hyperplastic/neoplastic disease states is well within the ability and knowledge of one skilled in the art. Certain of the methods for identification of patients which are at risk of developing neoplastic disease states which can be treated by the subject method are appreciated in the medical arts, such as family history of the development of a particular disease state and the presence of risk factors associated with the development of that disease state in the subject patient. The present application also describes other prognostic tests which can be used to make, or to augment a clinical predication about the use of the method of the present invention. A clinician skilled in the art can readily identify such candidate patients, by the use of, for example, clinical tests, physical examination and medical/family history.

Immunomodulatory Effects

In another aspect, this invention provides a method for modulating the activity of an immune cell by contacting the cell with a vitamin D3 compound of formulas I or II. Vitamin D3 compounds are known in the art for their inhibitory effects on the antigen-specific immune system. As used herein, the phrase "inhibition of an immune response" is intended to include decreases in T cell proliferation and activity, e.g., a decrease in $IL_2$, interferon-$\gamma$, GM-CSF synthesis and secretion (Lemire, J. M. (1992) *J. Cell Biochemistry* 49:26–31, Lemire, J. M. et al. (1994) *Endocrinology* 135 (6): 2813–2821; Bouillon, R. et al. (1995) *Endocine Review* 16 (2):231–32)

In one embodiment, the present invention provides a method for suppressing immune activity in an immune cell by contacting a pathological or non-pathological immune cell with an effective amount of a vitamin D3 compound of formulas I or II to thereby inhibit an immune response relative to the cell in the absence of the treatment. The present method can be performed on cells in culture, e.g., in vitro or ex vivo, or can be performed on cells present in an animal subject, e.g., as part of an in vivo therepeutic protocol. In vivo treatment can be carried out on a human or other animal subject.

The vitamin D3 compound of formula I or II can be tested initially in vitro for their inhibitory effects on T cell proliferation and secretory activity, as described in Reichel, H. et al., (1987) *Proc. Natl. Acad. Sci. USA* 84:3385–3389; Lemire, J. M. et al. (1985) *J. Immunol* 34:2032–2035. Alternatively, the immunosuppressive effects can be tested in vivo using the various animal models known in the art and summarized by Bouillon, R. et al. (1995) *Endocine Reviews* 16(2) 232 (Tables 6 and 7). For examples, animal models for autoimmune disorders, e.g., lupus, thyroiditis, encephalitis, diabetes and nephritis are described in (Lemire J. M. (1992) *J. Cell Biochem.* 49:26–31; Koizumi T. et al. (1985) *Int. Arch. Allergy Appl. Immunol.* 77:396–404; Abe J. et al. (1990) *Calcium Regulation and Bone Metabolism* 146–151; Fournier C. et al. (1990) *Clin. Immunol Immunopathol.* 54:53–63; Lemire J. M. and Archer D. C. (1991) *J. Clin. Invest.* 87:1103–1107); Lemire, J. M. et al., (1994) *Endocrinology* 135 (6):2818–2821; Inaba M. et al. (1992) *Metabolism* 41:631–635; Mathieu C. et al. (1992) *Diabetes*

41:1491–1495; Mathieu C. et al. (1994) *Diabetologia* 37:552–558; Lillevang S. T. et al. (1992) *Clin. Exp. Immunol.* 88:301–306, among others). Models for characterizing immunosuppressive activity during organ transplantation, e.g., skin graft, cardiac graft, islet graft, are described in Jordan S. C. et al. (1988) v Herrath D (eds) *Molecular, Cellular and Clinical Endocrinology* 346–347; Veyron P. et al. (1993) *Transplant Immunol.* 1:72–76; Jordan S. C. (1988) v Herrath D (eds) *Molecular, Cellular and Clinical Endocrinology* 334–335; Lemire J. M. et al. (1992) *Transplantation* 54:762–763; Mathieu C. et al. (1994) *Transplant Proc.* 26:3128–3129).

After identifying certain test compounds as effective suppresors of an immune response in vitro, these compounds can be used in vivo as part of a therapeutic protocol. Accordingly, another embodiment provides a method of suppressing an immune response, comprising administering to a subject a pharmaceutical preparation of a vitamin D3 compound of formula I or II, so as to inhibit immune reactions such as graft rejection, autoimmune disorders and inflammation.

For example, the subject vitamin D3 compounds of formulas I and II can be used to inhibit responses in clinical situations where it is desirable to downmodulate T cell responses. For example, in graft-versus-host disease, cases of transplantation, autoimmune diseases (including, for example, diabetes mellitus, arthritis (including rheumatoid arthritis, juvenile rheumatoid arthritis, osteoarthritis, psoriatic arthritis), multiple sclerosis, encephalomyelitis, diabetes, myasthenia gravis, systemic lupus erythematosis, autoimmune thyroiditis, dermatitis (including atopic dermatitis and eczematous dermatitis), psoriasis, Sjögren's Syndrome, including keratoconjunctivitis sicca secondary to Sjögren's Syndrome, alopecia areata, allergic responses due to arthropod bite reactions, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Crohn's disease, Graves ophthalmopathy, sarcoidosis, primary biliary cirrhosis, uveitis posterior, and interstitial lung fibrosis). Downmodulation of immune activity will also be desirable in cases of allergy such as, atopic allergy.

As described before, determination of a therapeutically effective immunosuppressive amount can be readily made by the attending clinician, as one skilled in the art, by the use of known techniques and by observing results obtained under analogous circumstances. Compounds which are determined to be effective in animals, e.g., dogs, rodents, may be extrapolated accordingly to humans by those skilled in the art. Starting dose/regimen used in animals can be estimated based on prior studies. For example, doses of vitamin D3 compounds of formulas I and II to treat autoimmune disorders in rodents can be initially estimated in the range of 0.1 g/kg/day to 1 g/kg/day, administered orally or by injection.

Those skilled in the art will know based upon the data obtained in animal studies, the dosage and route of administration in humans is expected to be similar to that in animals. Exemplary dose ranges to be used in humans are from 0.25 to 10 µg/day, preferably 0.5 to 5 µg/day per adult (U.S. Pat. No. 4,341,774).

Calcium and Phosphate Homeostasis

The present invention also relates to a method of treating in a subject a disorder characterized by deregulation of calcium metabolism. This method comprises contacting a pathological or non-pathological vitamin D3 responsive cell with an effective amount of a vitamin D3 compound of formula I or II to thereby directly or indirectly modulate calcium and phosphate homeostasis. The term "homeostasis" is art-recognized to mean maintenance of static, or constant, conditions in an internal environment. As used herein, the term "calcium and phospate homeostasis" refers to the careful balance of calcium and phosphate concentrations, intracellularly and extracellularly, triggered by fluctuations in the calcium and phosphate concentration in a cell, a tissue, an organ or a system. Fluctuations in calcium levels that result from direct or indirect responses to vitamin D3 compounds of formulas I and II are intended to be included by these terms. Techniques for detecting calcium fluctuation in vivo or in vitro are known in the art.

Exemplary $Ca^{++}$ homeostasis related assays include assays that focus on the intestine where intestinal $^{45}Ca^{2+}$ absorption is determined either 1) in vivo (Hibberd K. A. and Norman A. W. (1969) *Biochem. Pharmacol.* 18:2347–2355; Hurwitz S. et al. (1967) *J. Nutr.* 91:319–323; Bickle D. D. et al. (1984) *Endocrinology* 114:260–267), or 2) in vitro with everted duodenal sacs (Schachter D. et al. (1961) *Am. J. Physiol* 200:1263–1271), or 3) on the genomic induction of calbindin-$D_{28k}$ in the chick or of calbindin-$D_{9k}$ in the rat (Thomasset M. et al. (1981) *FEBS Lett.* 127:13–16; Brehier A. and Thomasset M. (1990) *Endocrinology* 127:580–587). The bone-oriented assays include: 1) assessment of bone resorption as determined via the release of $Ca^{2+}$ from bone in vivo (in animals fed a zero $Ca^{2+}$ diet) (Hibberd K. A. and Norman A. W. (1969) *Biochem. Pharmacol.* 18:2347–2355; Hurwitz S. et al. (1967) *J. Nutr.* 91:319–323), or from bone explants in vitro (Bouillon R. et al. (1992) *J. Biol. Chem.* 267:3044–3051), 2) measurement of serum osteocalcin levels [osteocalcin is an osteoblast-specific protein that after its synthesis is largely incorporated into the bone matrix, but partially released into the circulation (or tissue culture medium) and thus represents a good market of bone formation or turnover] (Bouillon R. et al. (1992) *Clin. Chem.* 38:2055–2060), or 3) bone ash content (Norman A. W. and Wong R. G. (1972) *J. Nutr.* 102:1709–1718). Only one kidney-oriented assay has been employed. In this assay, urinary $Ca^{2+}$ excretion is determined (Hartenbower D. L. et al. (1977) Walter de Gruyter, Berlin pp 587–589); this assay is dependent upon elevations in the serum $Ca^{2+}$ level and may reflect bone $Ca^{2+}$ mobilizing activity more than renal effects. Finally, there is a "soft tissue calcification" assay that has been employed to detect the consequences of 1α,25(OH)$_2$D3 or analog-induced severe hypercalcemia. In this assay a rat is administered an intraperitoneal dose of $^{45}Ca^{2+}$, followed by seven daily relative high doses of 1α,25(OH)$_2$D3 or the analog of interest; in the event of onset of a severe hypercalcemia, soft tissue calcification can be assessed by determination of the $^{45}Ca^{2+}$ level. In all these assays, vitamin D3 compounds or formulas I and II are administered to vitamin D-sufficient or -deficient animals, as a single dose or chronically (depending upon the assay protocol), at an appropriate time interval before the end point of the assay is quantified.

In certain embodiments, vitamin D3 compounds of formulas I and II can be used to modulate bone metabolism. The language "bone metabolism" is intended to include direct or indirect effects in the formation or degeneration of bone structures, e.g., bone formation, bone resorption, etc., which may ultimately affect the concentrations in serum of calcium and phosphate. This term is also intended to include effects of vitamin D3 compounds in bone cells, e.g. osteoclasts and osteoblasts, that may in turn result in bone formation and degeneration. For example, it is known in the art, that vitamin D3 compounds of formulas I and II exert effects on the bone forming cells, the osteoblasts through genomic and non-genomic pathways (Walters M. R. et al. (1982) *J. Biol. Chem.* 257:7481–7484; Jurutka P. W. et al. (1993) *Biochemistry* 32:8184–8192; Mellon W. S. and DeLuca H. F. (1980) *J. Biol. Chem.* 255:4081–4086). Similarly, vitamin D3 compounds of formulas I and II are known in the art to support different activities of bone resorbing osteoclasts such as the stimulation of differentiation of monocytes and mononuclear phagocytes into osteoclasts (Abe E. et al. (1988) *J. Bone Miner Res.* 3:635–645; Takahashi N. et al. (1988) *Endocrinology* 123:1504–1510; Udagawa N. et al. (1990) *Proc. Natl. Acad. Sci. USA* 87:7260–7264). Accordingly, vitamin D3 compounds of formulas I and II that modulate the production of bone cells can influence bone formation and degeneration.

The present invention provides a method for modulating bone cell metabolism by contacting a pathological or a non-pathological bone cell with an effective amount of a vitamin D3 compound of formula I or II to thereby modulate bone formation and degeneration. The present method can be performed on cells in culture, e.g., in vitro or ex vivo, or can be performed in cells present in an animal subject, e.g., cells in vivo. Exemplary culture systems that can be used include osteoblast cell lines, e.g., ROS 17/2.8 cell line, monocytes, bone marrow culture system (Suda T. et al. (1990) *Med. Res. Rev.* 7:333–366; Suda T. et al. (1992) *J. Cell Biochem.* 49:53–58) among others. Selected compounds can be further tested in vivo, for example, animal models of osteopetrosis and in human disease (Shapira F. (1993) *Clin. Orthop.* 294:34–44).

In a preferred embodiment, a method for treating osteoporosis is provided, comprising administering to a subject a pharmaceutical preparation of a vitamin D3 compound of formula I or II to thereby ameliorate the condition relative to an untreated subject. The rationale for utilizing vitamin D3 compounds in the treatment of osteoporosis is supported by studies indicating a decrease in serum concentration of $1\alpha,25(OH)_2D3$ in elderly subjects (Lidor C. et al. (1993) *Calcif. Tissue Int.* 52:146–148). In vivo studies using vitamin D3 compounds in animal models and humans are described in Bouillon, et al. (1995) *Endocrine Reviews* 16(2):229–231.

Vitamin D3 compounds of formulas I and II can be tested in ovarectomized animals, e.g., dogs, rodents, to assess the changes in bone mass and bone formation rates in both normal and estrogen-deficient animals. Clinical trials can be conducted in humans by attending clinicians to determine therapeutically effective amounts of the vitamin D3 compounds of formulas I and II in preventing and treating osteoporosis.

Preferred compounds to be tested include 3-epi forms of 3-epi forms of $1\alpha(OH)D_3$ as shown in Example II, which shows the production of $1\alpha(OH)$-3-epi-$D_3$ in the rat osteosarcoma cell line UMR-106. The 3 epi conversion of $1\alpha(OH)$-$D_3$ presents the possibility of a yet improved of this compound.

In other embodiments, therapeutic applications of the vitamin D3 compounds of formulas I and II include treatment of other diseases characterized by metabolic calcium and phosphate deficiencies. Exemplary of such diseases are the following: osteoporosis, osteodystrophy, osteomalacia, rickets, osteitis fibrosa cystica, renal osteodystrophy, osteosclerosis, anti-convulsant treatment, osteopenia, fibrogenesis-imperfecta ossium, secondary hyperparathyrodism, hypoparathyroidism, hyperparathyroidism, cirrhosis, obstructive jaundice, drug induced metabolism, medullary carcinoma, chronic renal disease, hypophosphatemic VDRR, vitamin D-dependent rickets, sarcoidosis, glucocorticoid antagonism, malabsorption syndrome, steatorrhea, tropical sprue, idiopathic hypercalcemia and milk fever.

Hormone Secretion

In yet another aspect, the present invention provides a method for modulating hormone secretion of a vitamin D3-responsive cell, e.g., an endocrine cell. The language "hormone secretion" is art-recognized and includes both genomic and non-genomic activities of vitamin D3 compounds of formulas I and II that control the transcription and processing responsible for secretion of a given hormone e.g., parathyroid hormone (PTH), calcitonin, insulin, prolactin (PRL) and TRH in a vitamin D3 responsive cell (Bouillon, R. et al. (1995) *Endocrine Reviews* 16(2):235–237). The language "vitamin D3 responsive cells" as used herein is intended to include endocrine cells which respond to vitamin D3 compounds of formulas I and II by altering gene expression and/or post-transcriptional processing secretion of a hormone. Exemplary endocrine cells include parathyroid cells, pancreatic cells, pituitary cells, among others.

The present method can be performed on cells in culture, e.g. in vitro or ex vivo, or on cells present in an animal subject, e.g., in vivo. Vitamin D3 compounds of formulas I and II can be initially tested in vitro using primary cultures of parathyroid cells. Other systems that can be used include the testing by prolactin secretion in rat pituitary tumor cells, e.g., GH4 C1 cell line (Wark J. D. and Tashjian Jr. A. H. (1982) *Endocrinology* 111:1755–1757; Wark J. D. and Tashjian Jr. A. H. (1983) *J. Biol. Chem.* 258:2118–2121; Wark J. D. and Gurtler V. (1986) *Biochem. J.* 233:513–518) and TRH secretion in GH4 C1 cells. Alternatively, the effects of vitamin D3 compounds of formulas I and II can be characterized in vivo using animals models as described in Nko M. et al. (1982) *Miner Electrolyte Metab.* 5:67–75; Oberg F. et al. (1993) *J. Immunol.* 150:3487–3495; Bar-Shavit Z. et al. (1986) *Endocrinology* 118:679–686; Testa U. et al. (1993) *J. Immunol.* 150:2418–2430; Nakamaki T. et at. (1992) *Anticancer Res.* 12:1331–1337; Weinberg J. B. and Larrick J. W. (1987) *Blood* 70:994–1002; Chambaut-Guerin A. M. and Thomopoulos P. (1991) *Eur. Cytokine New.* 2:355; Yoshida M. et al. (1992) *Anticancer Res.* 12:1947–1952; Momparler R. L. et al. (1993) *Leukemia* 7:17–20; Eisman J. A. (1994) Kanis JA (eds) *Bone and Mineral Research* 2:45–76; Veyron P. et al. (1993) *Transplant Immunol.* 1:72–76; Gross M. et al. (1986) *J. Bone Miner Res.* 1:457–467; Costa E. M. et al. (1985) *Endocrinology* 117:2203–2210; Koga M. et al. (1988) *Cancer Res.* 48:2734–2739; Franceschi R. T. et al. (1994) *J. Cell Physiol.* 123:401–409; Cross H. S. et al. (1993) *Naunyn Schmiedebergs Arch. Pharmacol.* 347:105–110; Zhao X. and Feldman D. (1993) *Endocrinology* 132:1808–1814; Skowronski R. J. et al. (1993) *Endocrinology* 132:1952–1960; Henry H. L. and Norman A. W. (1975) *Biochem. Biophys. Res. Commun.* 62:781–788; Wecksler W. R. et al. (1980) *Arch. Biochem. Biophys.* 201:95–103; Brumbaugh P. F. et al. (1975) *Am. J. Physiol.* 238:384–388; Oldham S. B. et al. (1979) *Endocrinology* 104:248–254; Chertow B. S. et al. (1975) *J. Clin Invest.* 56:668–678; Canterbury J. M. et al. (1978) *J. Clin. Invest.* 61:1375–1383; Quesad J. M. et al. (1992) *J. Clin. Endocrinol. Metab.* 75:494–501.

In certain embodiments, the vitamin D3 compounds of the present invention can be used to inhibit parathyroid hormone (PTH) processing, e.g., transcriptional, translational processing, and/or secretion of a parathyroid cell as part of a therapeutic protocol. Therapeutic methods using these compounds can be readily applied to all diseases, involving direct or indirect effects of PTH activity, e.g., primary or secondary responses. For example, it is known in the art that PTH induces the formation of 1,25-dihydroxy vitamin D3 in the kidneys, which in turn in increases calcium and phosphate absorption from the intestine that causes hypercalcemia. Thus inhibition of PTH processing and/or secretion would indirectly inhibit all of the responses mediated by PTH in vivo. Accordingly, therapeutic applications for these vitamin D3 compounds of formulas I and II include treating diseases such as secondary hyperparathyroidism of chronic renal failure (Slatopolsky E. et al. (1990) *Kidney Int.* 38:S41–S47; Brown A. J. et al. (1989) *J. Clin. Invest.* 84:728–732). Determination of therapeutically affective amounts and dose regimen can be performed by the skilled artisan using the data described in the art.

Protection Against Neuronal Loss

In yet another aspect, the present invention provides a method of protecting against neuronal loss by contacting a vitamin D3 responsive cell, e.g., a neuronal cell, with a vitamin D3 compound of formula I or II to prevent or retard neuron loss. The language "protecting against" is intended to include prevention, retardation, and/or termination of deterioration, impairment, or death of a neurons. The language "vitamin D3 responsive cells" as used herein is intended to include neuronal cells which respond to vitamin D3 compounds of formulas I and IT by altering gene expression and/or intracellular metabolism. Exemplary neuronal cells include hippocampal cells, dopaminergic cells, cholinergic cells, among others.

Neuron loss can be the result of any condition of a neuron in which its normal function is compromised. Neuron deterioration can be the result of any condition which compromises neuron function which is likely to lead to neuron loss. Neuron function can be compromised by, for example, altered biochemistry, physiology, or anatomy of a neuron. Deterioration of a neuron may include membrane, dendritic, or synaptic changes which are detrimental to normal neuronal functioning. The cause of the neuron deterioration, impairment, and/or death may be unknown. Alternatively, it may be the result of age- and/or disease-related changes which occur in the nervous system of a subject.

When neuron loss is described herein as "age-related", it is intended to include neuron loss resulting from known and unknown bodily changes of a subject which are associated with aging. When neuron loss is described herein as "disease-related", it is intended to include neuron loss resulting from known and unknown bodily changes of a subject which are associated with disease. It should be understood, however, that these terms are not mutually exclusive and that, in fact, many conditions that result in the loss of neurons are both age- and disease-related.

Exemplary age-related diseases associated with neuron loss and changes in neuronal morphology include, for example, Alzheimer's Disease, Pick's Disease, Parkinson's Disease, Vascular Disease, Huntington's Disease, and Age-Associated Memory Impairment. In Alzheimer's Disease patients, neuron loss is most notable in the hippocampus, frontal, parietal, and anterior temporal cortices, amygdala, and the olfactory system. The most prominently affected zones of the hippocampus include the CA1 region, the subiculum, and the entorhinal cortex. Memory loss is considered the earliest and most representative cognitive change because the hippocampus is well known to play a crucial role in memory. Pick's Disease is characterized by severe neuronal degeneration in the neocortex of the frontal and anterior temporal lobes which is sometimes accompanied by death of neurons in the striatum. Parkinson's Disease can be identified by the loss of neurons in the substantia nigra and the locus ceruleus. Huntington's Disease is characterized by degeneration of the intrastriatal and cortical cholinergic neurons and GABA-ergic neurons. Parkinson's and Huntington's Diseases are usually associated with movement disorders, but often show cognitive impairment (memory loss) as well.

Age-Associated Memory Impairment (AAMI) is another age-associated disorder that is characterized by memory loss in healthy, elderly individuals in the later decades of life. Crook, T. et al. (1986) *Devel. Neuropsych.* 2(4):261–276. Presently, the neural basis for AAMI has not been precisely defined. However, neuron death with aging has been reported to occur in many species in brain regions implicated in memory, including cortex, hippocampus, amygdala, basal ganglia, cholinergic basal forebrain, locus ceruleus, raphe nuclei, and cerebellum. Crook, T. et al. (1986) *Devel. Neuropsych.* 2(4):261–276.

Vitamin D3 compounds of formulas I and II can protect against neuron loss by genomic or non-genomic mechanisms. Nuclear vitamin D3 receptors are well known to exist in the periphery but have also been found in the brain, particularly in the hippocampus and neocortex. Non-genomic mechanisms may also prevent or retard neuron loss by regulating intraneuronal and/or peripheral calcium and phosphate levels. Furthermore, vitamin D3 compounds of formulas I and II may protect against neuronal loss by acting indirectly, e.g., by modulating serum PTH levels. For example, a positive correlation has been demonstrated between serum PTH levels and cognitive decline in Alzheimer's Disease.

The present method can be performed on cells in culture, e.g. in vitro or ex vivo, or on cells present in an animal subject, e.g., in vivo. Vitamin D3 compounds of formulas I and II can be initially tested in vitro using neurons from embryonic rodent pups (See e.g. U.S. Pat. No. 5,179,109-fetal rat tissue culture), or other mammalian (See e.g. U.S. Pat. No. 5,089,517-fetal mouse tissue culture) or non-mammalian animal models. These culture systems have been used to characterize the protection of peripheral, as well as, central nervous system neurons in animal or tissue culture models of ischemia, stroke, trauma, nerve crush, Alzheimer's Disease, Pick's Disease, and Parkinson's Disease, among others. Examples of in vitro systems to study the prevention of destruction of neocortical neurons include using in vitro cultures of fetal mouse neurons and glial cells previously exposed to various glutamate agonists, such as kainate, NMDA, and α-amino-3-hydroxy-5-methyl-4-isoxazolepronate (AMPA). U.S. Pat. No. 5,089,517. See also U.S. Pat. No. 5,170,109 (treatment of rat cortical/hippocampal neuron cultures with glutamate prior to treatment with neuroprotective compound); U.S. Pat. Nos. 5,163,196 and 5,196,421 (neuroprotective excitatory amino acid receptor antagonists inhibit glycine, kainate, AMPA receptor binding in rats).

Alternatively, the effects of vitamin D3 compounds of formulas I and II can be characterized in vivo using animals models. Neuron deterioration in these model systems is often induced by experimental trauma or intervention (e.g. application of toxins, nerve crush, interruption of oxygen supply). For example, in order to demonstrate that certain N-methyl-D-aspartate (NMDA), an excitatory amino acid neurotransmitter receptor, antagonists were useful as anticonvulsants and neuroprotectants, the inventors in U.S. Pat. No. 4,957,909 employed a model wherein Swiss-albino mice and rat hippocampal neurons were subjected to overstimulation of excitatory amino acid receptors subsequent to treatment with the NMDA antagonists. A similar study was performed wherein the utility of certain NMDA antagonists as agents that prevent neurodegeneration was demonstrated by treating mice with NMDA subsequent to treatment with the NMDA antagonists. U.S. Pat. No. 5,168,103.

Smooth Muscle Cells

In yet another aspect, the present invention provides a method of modulating the activity of a vascular smooth muscle cell by contacting a vitamin D3-responsive smooth muscle cell with a vitamin D3 compounds of formulas I or II to activate or, preferably, inhibit the activity of the cell. The language "activity of a smooth muscle cell" is intended to include any activity of a smooth muscle cell, such as proliferation, migration, adhesion and/or metabolism.

In certain embodiments, the vitamin D3 compounds of formulas I and II can be is used to treat diseases and conditions associated with aberrant activity of a vitamin D3-responsive smooth muscle cell. For example, the present invention can be used in the treatment of hyperproliferative vascular diseases, such as hypertension induced vascular remodeling, vascular restenosis and atherosclerosis. In other embodiments, the present invention can be used in treating disorders characterized by aberrant metabolism of a vitamin D3-responsive smooth muscle cell, e.g., arterial hypertension.

The present method can be performed on cells in culture, e.g. in vitro or ex vivo, or on cells present in an animal subject, e.g., in vivo. Vitamin D3 compounds of formulas I and II can be initially tested in vitro as described in Catellot et al. (1982), *J. Biol. Chem.* 257(19): 11256.

This invention is further illustrated by the following examples which in no way should be construed as being further limiting. It is understood by the ordinary skilled artisan that production of a vitamin D3 compound of formula I or II in a cell is indicative that such compound is biologically active in such cell, and thus that it can be used in treating conditions arising from aberrant activity of such cells. For example, production of vitamin D3 compounds of formulas I and II in keratinocytes is indicative that such vitamin D3 compounds are biologically active in those cells and can be used in treating conditions such as psoriasis. The contents of all cited references (including literature references, issued patents, published patent applications, and co-pending patent applications) cited throughout this application are hereby expressly incorporated by reference.

EXAMPLES

Example I

Figures 1, 1A, 2:
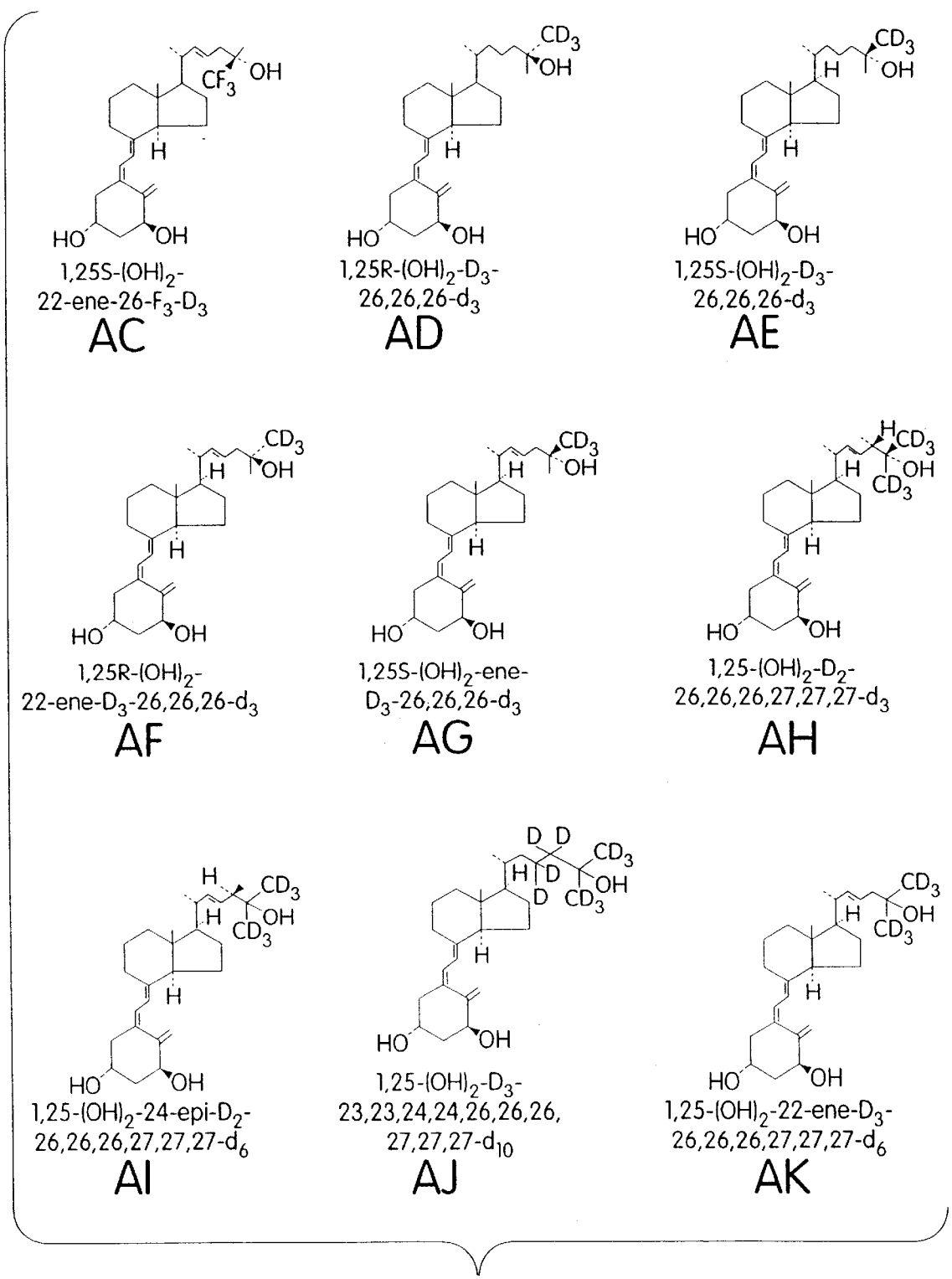
FIG. 2 shows the HPLC profile and UV spectra of the metabolites produced in human keratinocytes incubated with 1α, 25(OH)$_2$-3-epi vitamin $D_3$.
Figures 1, 1A, 2, 3:
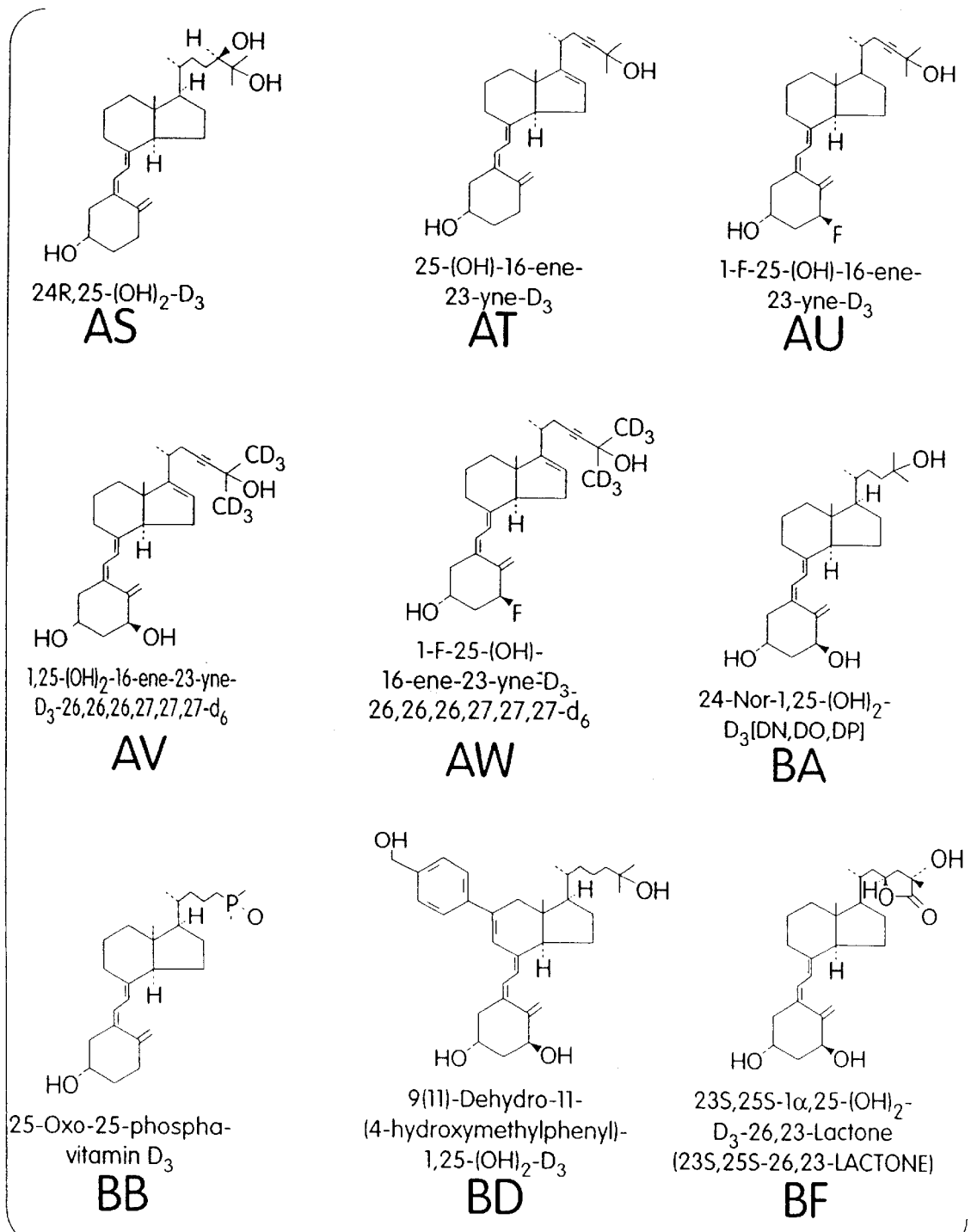
FIG. 3 shows the mass spectra of 1α, 25(OH)$_2$-3-epi vitamin D$_3$ and its cyclic ether metabolite.
Figures 1, 1A, 2, 3, 4:
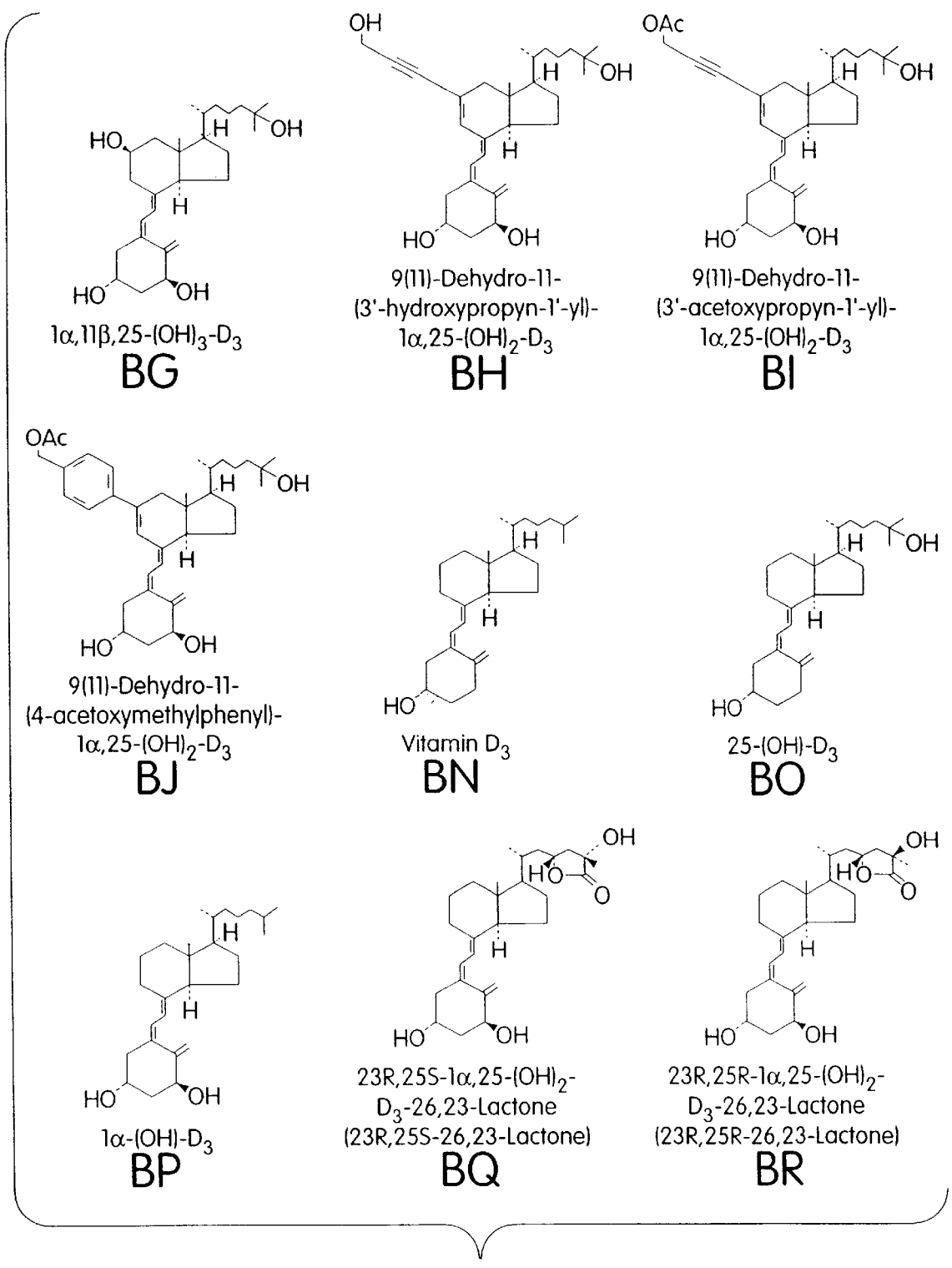
FIG. 4 shows the proposed metabolic pathway for the formation of the cyclic ether metabolite of 1α, 25(OH)$_2$-3-epi vitamin D$_3$.
Figures 1, 1A, 2, 3, 4, 5:
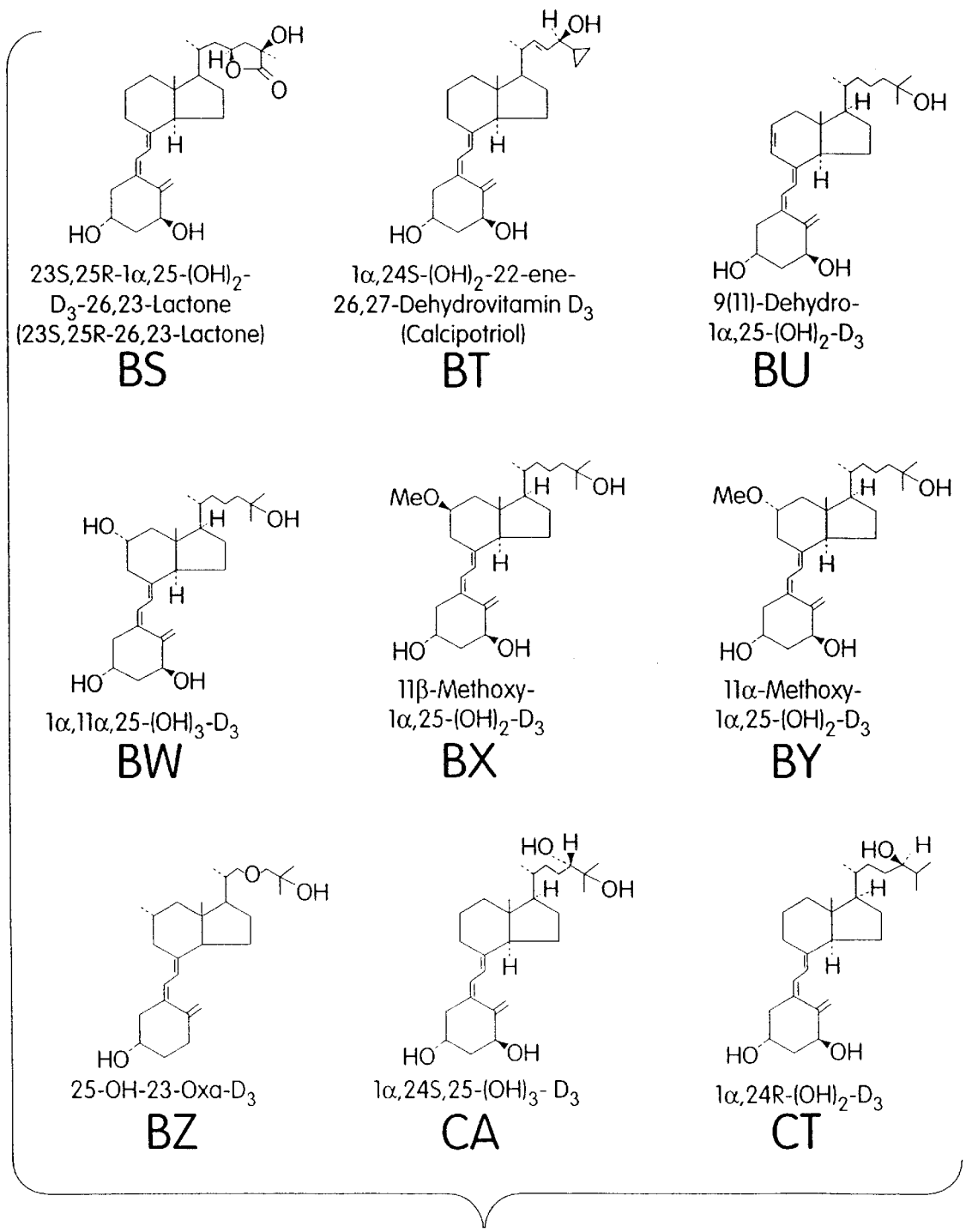

Isolation and Identification of a Cyclic Ether Metabolite of α, 25-Dihydroxy-vitamin $D_3$ in Human Keratinocytes As described herein, $1\alpha 25(OH)_2$-3-epi-$D_3$ is metabolized into a less polar metabolite than $1\alpha 25(OH)_2$-3-epi-$D_3$, peak M1, in human keratinocytes (FIG. 2). FIG. 2 shows the HPLC profile and UV spectra of the metabolites produced in human keratinocytes incubated with $1\alpha 25(OH)_2$-3-epi3$D_3$ (1uM) for 24H. On a straight phase HPLC system, this metabolite (M1) is more polar than 25(OH) $D_3$ but less polar than $1\alpha 25(OH)_2 D_3$ and similar to that of $1\alpha(OH)D_3$. Mass spectrometric analysis reveals a molecular ion of 414 m/z, which is 2 mass units less than the starting $1\alpha 25(OH)_2D_3$, shown in FIG. 3. FIG. 3 shows the mass spectra of $1\alpha(OH)$ 2-3-epi-$D_3$ (M) (upper panel) and its cyclic ether metabolite ($M_1$) (lower panel) isolated from human keratinocytes incubated with $1\alpha 25(OH)_2$-3-epi-$D_3$(1 uM) for 24 h. The typical fragments at m/z 134 and 152 m/z indicate an unmodified A-ring and cistriene structure. A double bond introduced at either C, D rings or the side chain would be consistent with the molecular weight. However, this type of unsaturated metabolite still possesses a free 25-hydroxyl group and is expected to have similar retention time as the starting compound; this is contradicting to what was observed. Furthermore, the absence of mass fragments at 59 m/z suggests the absence of a 25-hydroxyl group. The absence of the familiar side chain cleavage fragments at 251, 269 and 287 m/z also suggests a modified 25-hydroxyl group and a possible structural change at C-20 to retard the cleavage at carbons 17 and 20. A cyclic structure as shown in FIGS. 3 and 4 is supported by these mass spectrometric and chromatographic evidences. This proposed structure is consistent with the loss of m/z 58 (acetone) to form m/z 356 and the subsequent fragments at 338, 320 and 314.

It is probable that the 3-epi modification of the A-ring allows alternate side chain reactions to occur. FIG. 4 summarizes the proposed metabolic pathway for the formulation of the cyclic ether metabolite of $1\alpha 25(OH)2$-3-epi-$D_3$. The formation of a cyclic ether structure could result from a hydroxylation at either C-17 or C-20 and the subsequent reaction with the 25-hydroxyl group to form an ether linkage as shown in FIG. 4. This type of metabolic reactions are known to occur in hydroxylated fatty acids. Thus, it is probable that some of the unidentified metabolites can be C-17 or C-20-hydroxylated metabolites of $1\alpha 25(OH)2$-3-epi-$D_3$.

Example II

Figure 5A:
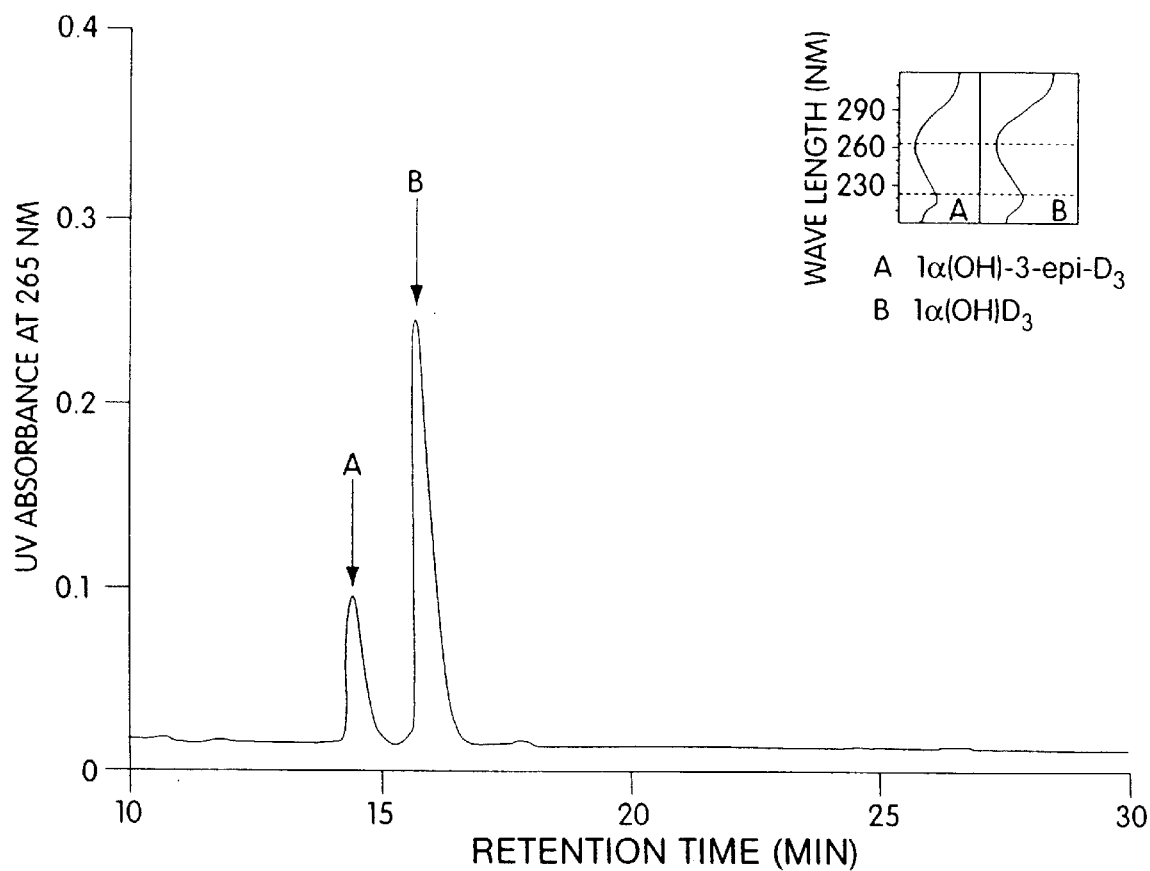
FIG. 5A shows the metabolism of 1α(OH)-vitamin D$_3$ into its 3 epi form in the rat osteosarcoma cell line (UMR-106).
Figure 5B:
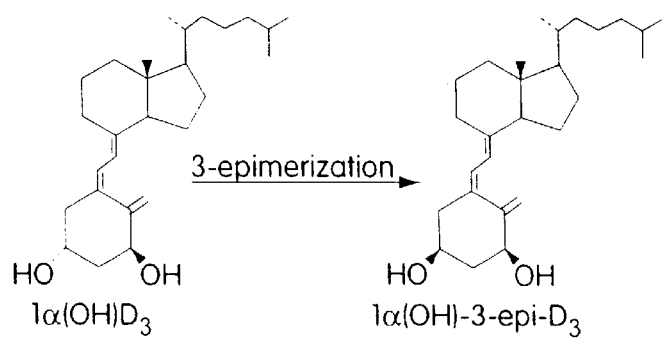
FIG. 5B is a schematic of the 3-epimerization of 1α(OH) D$_3$ into 1α(OH)-3-epi vitamin D$_3$.
Figure 6A:
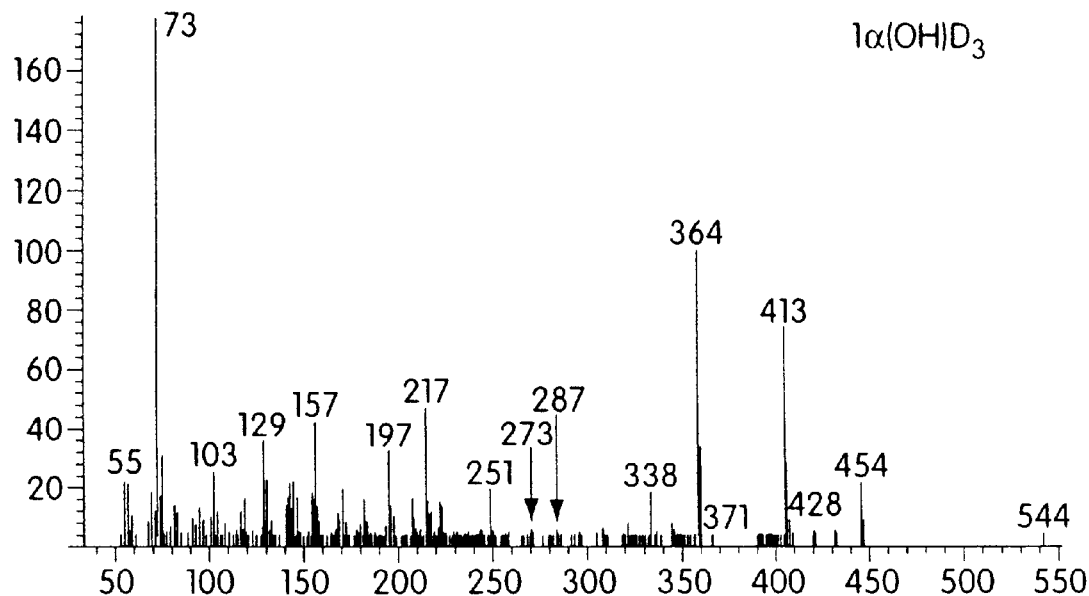
Figure 6B:
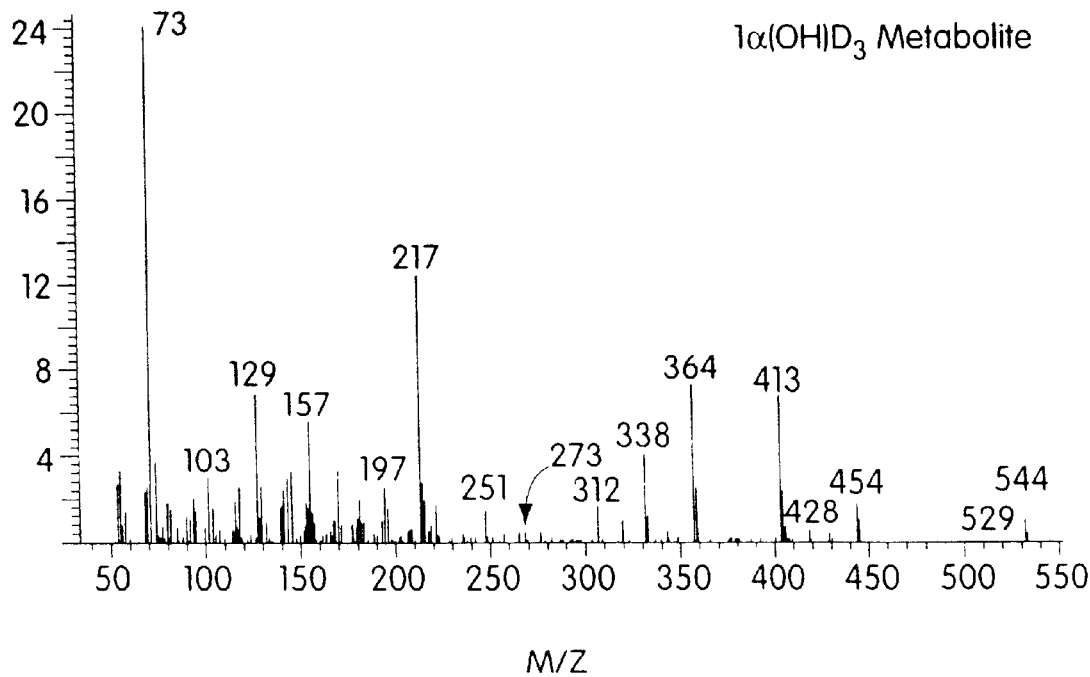
Figure 7A:
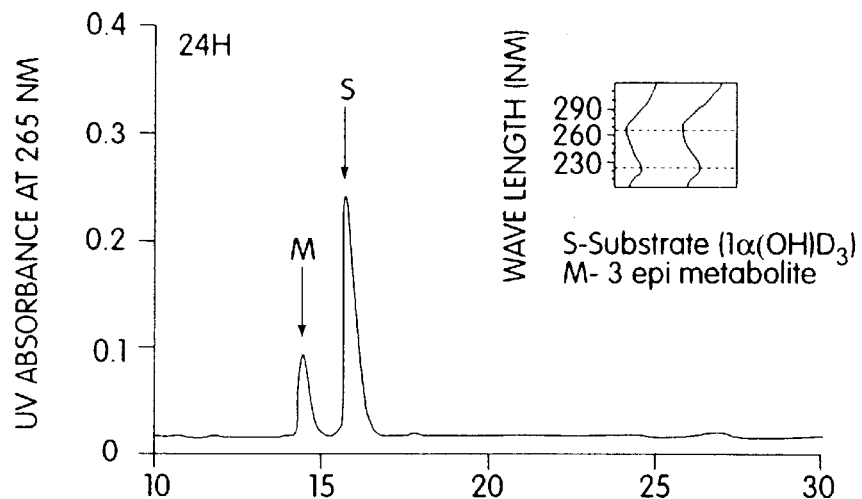
Figure 7B:
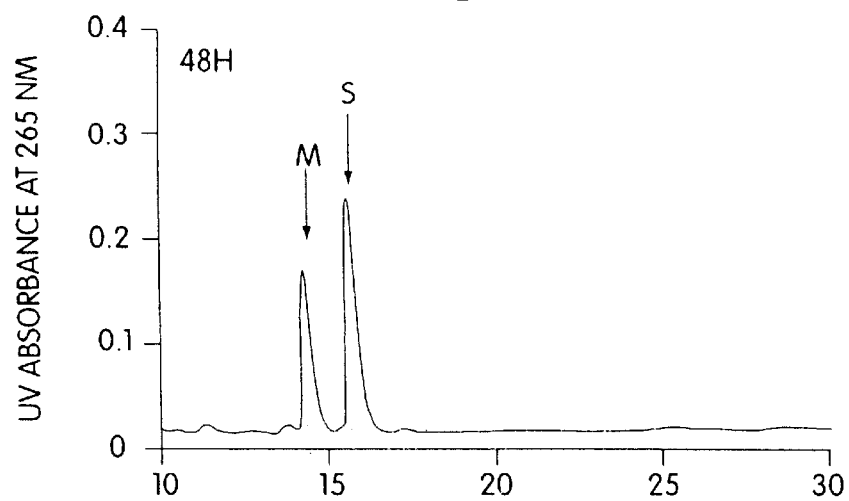
Figure 7C:
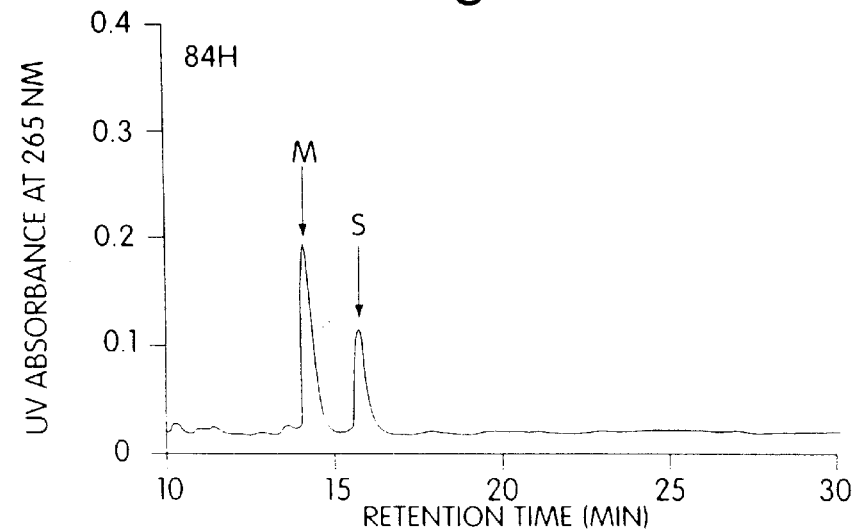

Isolation and Identification of a 3-Epi Metabolite of $1\alpha$ Hydroxy-vitamin $D_3$ in Human Keratinocytes FIG. 5A shows the metabolism of $1\alpha(OH)$-$D_3$ into its 3 epi form in the osteosarcoma cell line UMR-106. Peak A represents the 3-epi form of $1\alpha(OH)D_3$. Peak B corresponds to the substrate, $1\alpha(OH)D_3$. The insert panels show the UV spectra of the various metabolites as monitored by photodiode array detector. FIG. 5B shows a schematic representation of the 3-epimerization of $1\alpha(OH)D_3$ into $1\alpha(OH)$-3-epi vitamin $D_3$. Similar to $1\alpha(OH)D_3$, $1\alpha(OH)$-3-epi vitamin $D_3$ can be converted into the 25-hydroxylated form in vivo.

$1\alpha(OH)D_3$ compounds are currently used in the treatment of osteoporosis. Thus, 3-epi forms of these compounds may be used as substitutes for $1\alpha(OH)D_3$ compounds in treating osteoporosis.

Example III

Confirmation of 3-epi Configuration of $1\alpha(OH)$ 3-epi Vitamin $D_3$

Figures 1, 1A, 2, 3, 4, 5, 6:
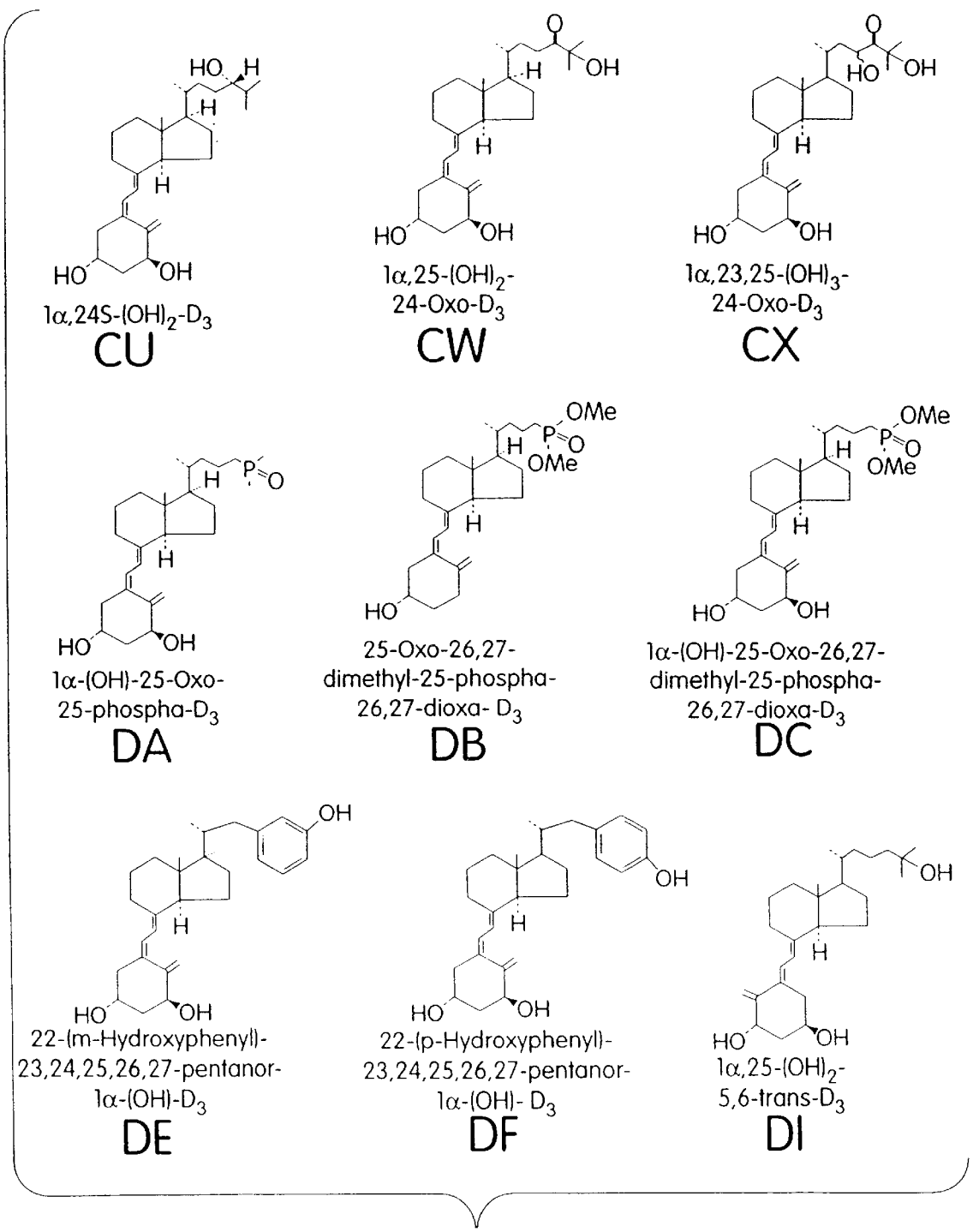
FIG. 6 shows the mass spectra of 1α(OH)D$_3$ and its 3-epi metabolite.

To confirm the production of $1\alpha(OH)$ 3-epi vitamin $D_3$ in bone cells. the metabolites of $1\alpha$-3-epi-$D_3$ produced by the osteosarcoma cell line (UMR-106) were analyzed by mass spectroscopy. FIG. 6 shows the mass spectra of $1\alpha(OH)D_3$ (upper panel) and its 3-epi metabolite (lower panel). A comparison of these two mass spectra revealed difference in peaks observed only in the 3-epi metabolite, for example, fragments having molecular weights of approximately m/z 57, 217, 312 and 529 (lower panel). The mass spectrum of the 3-epi metabolite was independently confirmed to be 1α(OH) 3-epi vitamin $D_3$.

Example IV

Figures 1, 1A, 2, 3, 4, 5, 6, 7:
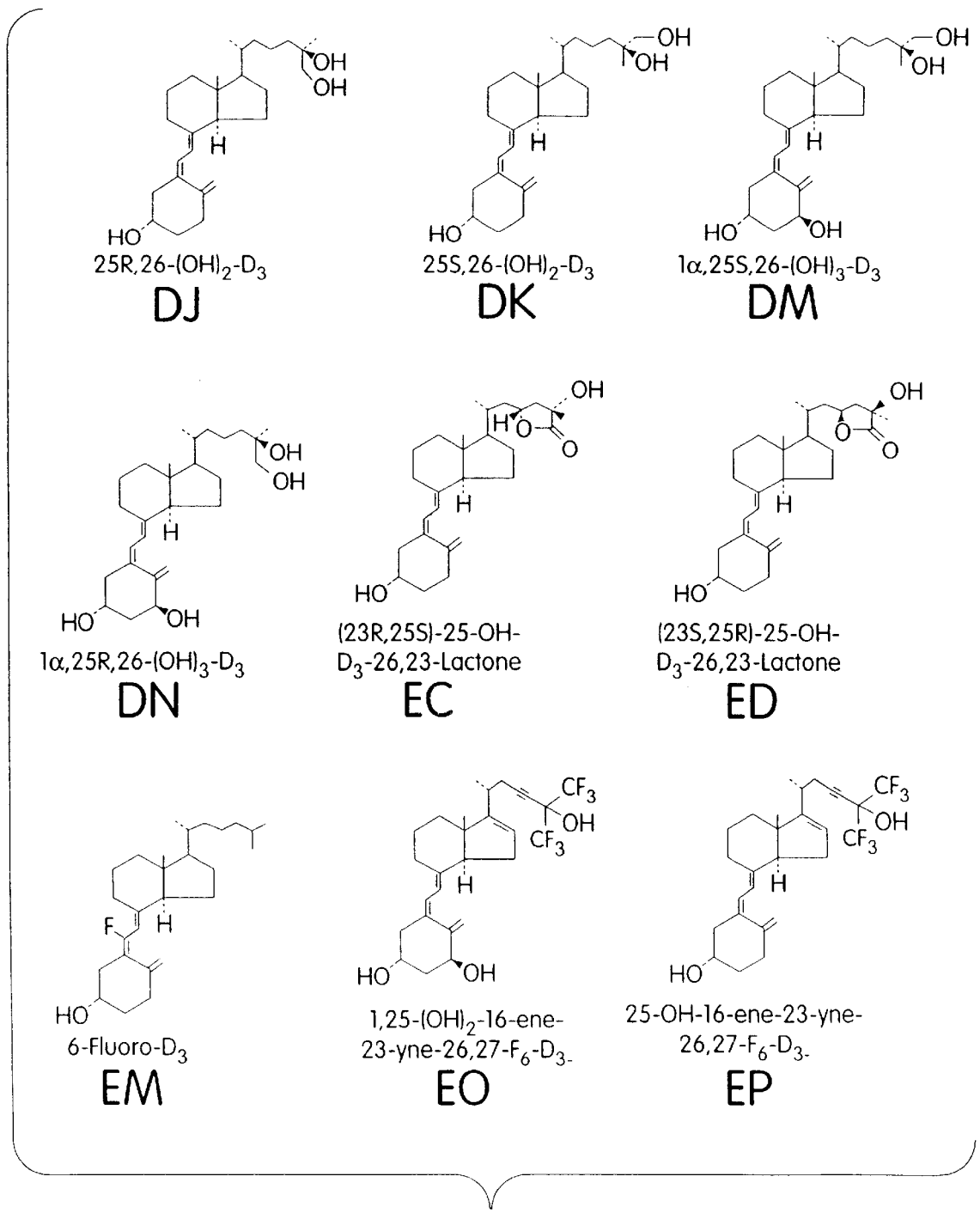
FIG. 7 shows the HPLC profile and UV spectra of the metabolites produced in rat osteosarcoma cell lines (UMR-106) which were incubated with 1α(OH)D$_3$ for 24, 48, or 84 hours.
Figures 1, 1A, 2, 3, 4, 5, 6, 7, 8:
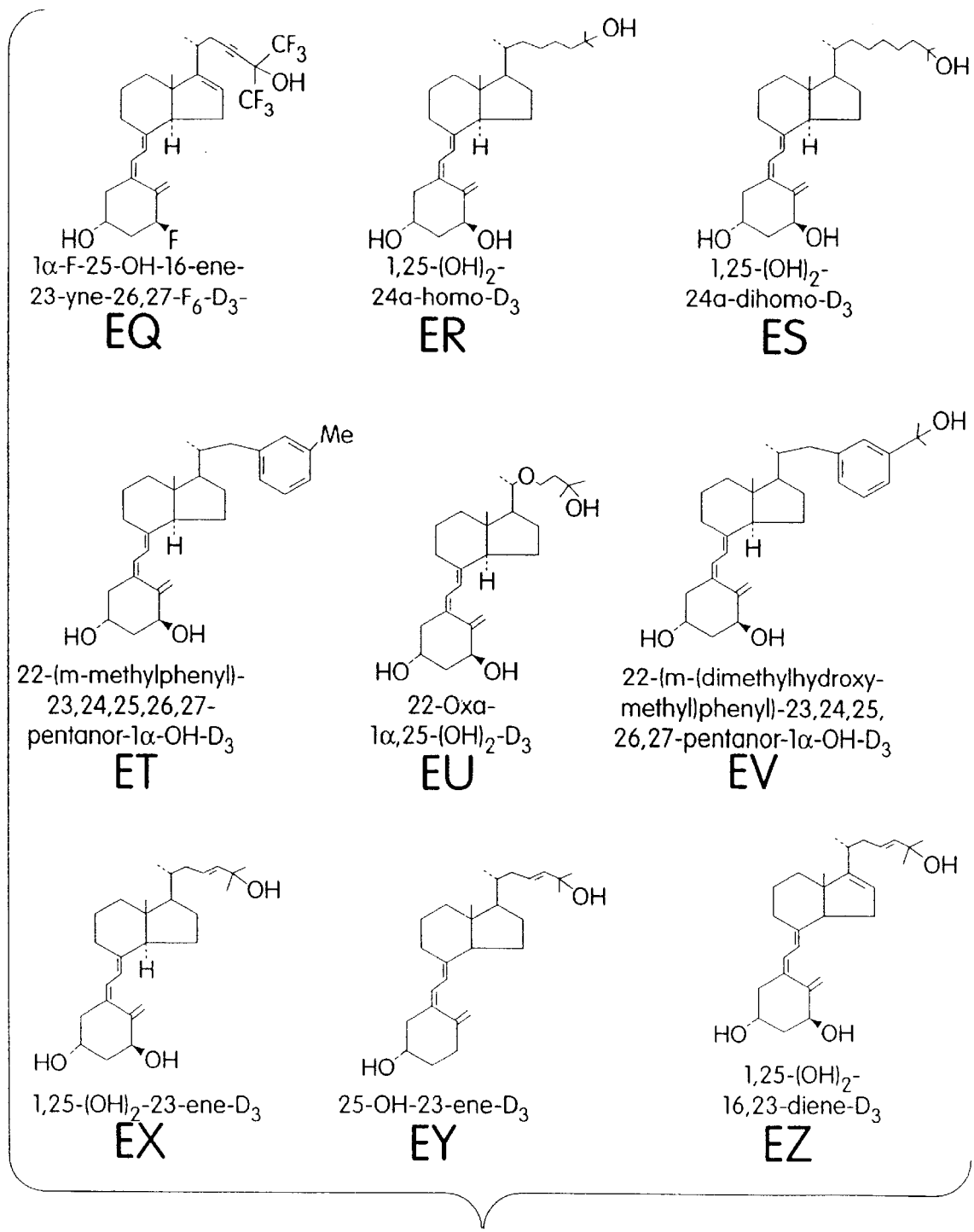
Figures 1, 1A, 2, 3, 4, 5, 6, 7, 8, 9:
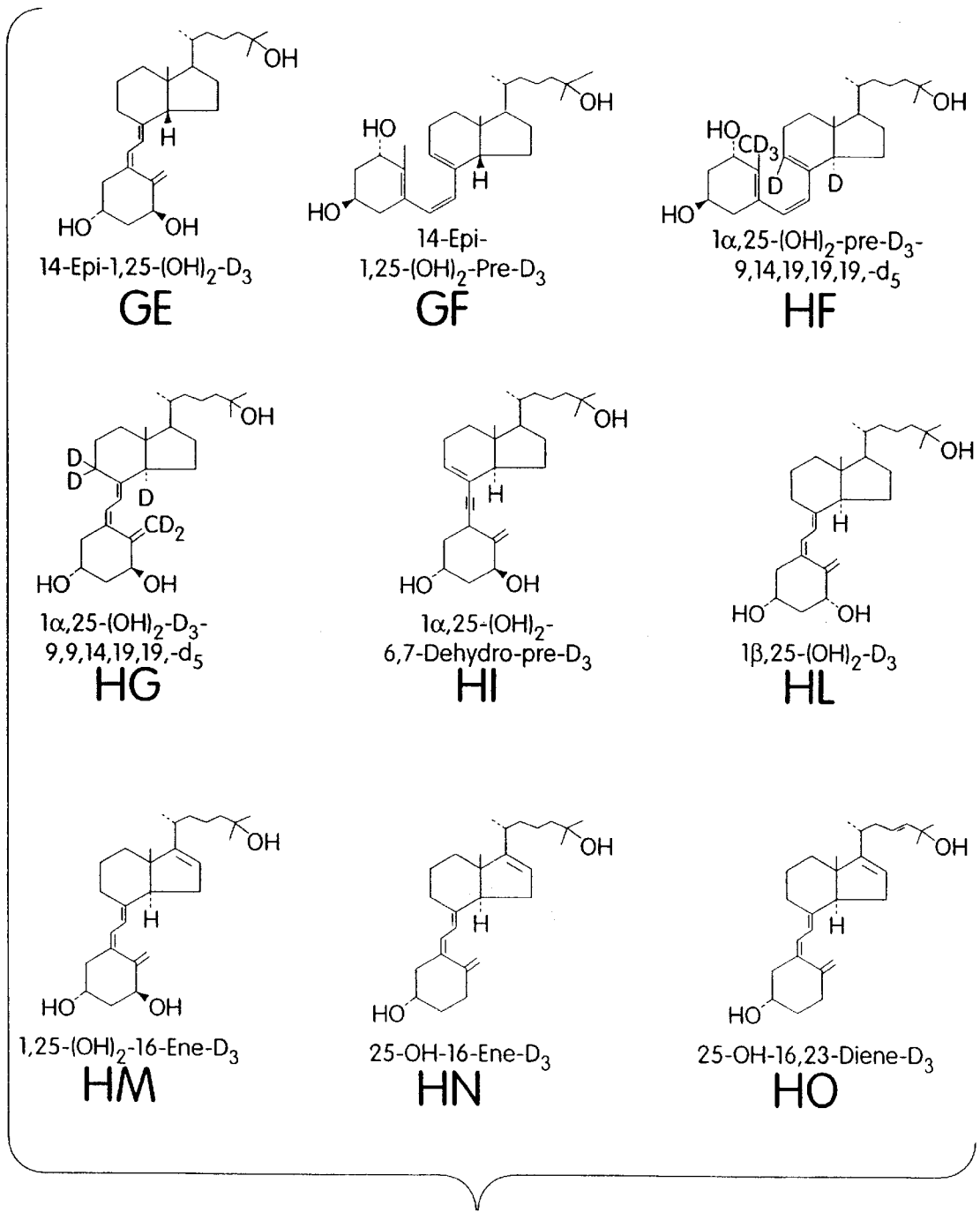
Figures 1, 1A, 2, 3, 4, 5, 6, 7, 8, 9, 10:
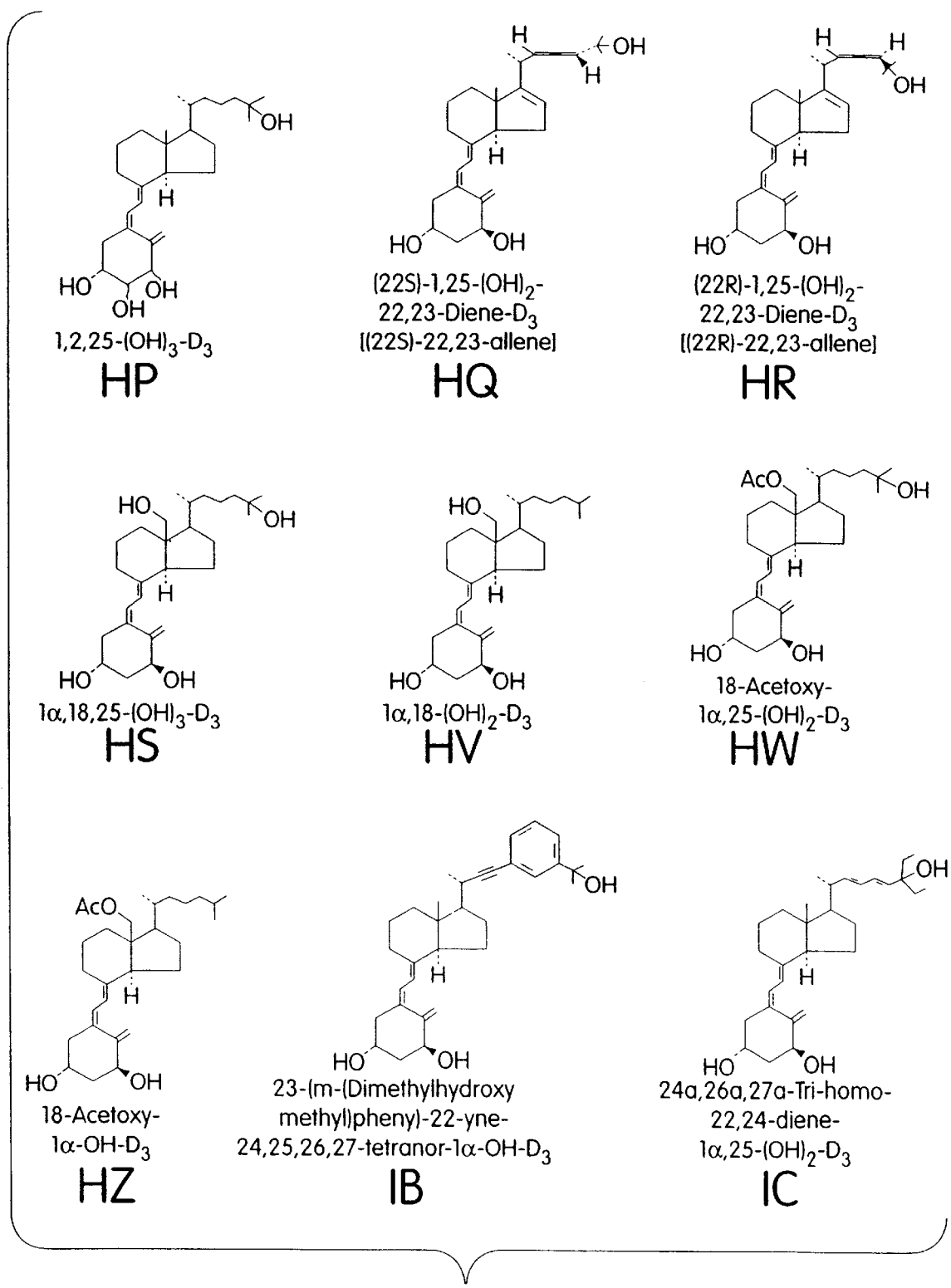
Figures 1, 1A, 2, 3, 4, 5, 6, 7, 8, 9, 10, 11:
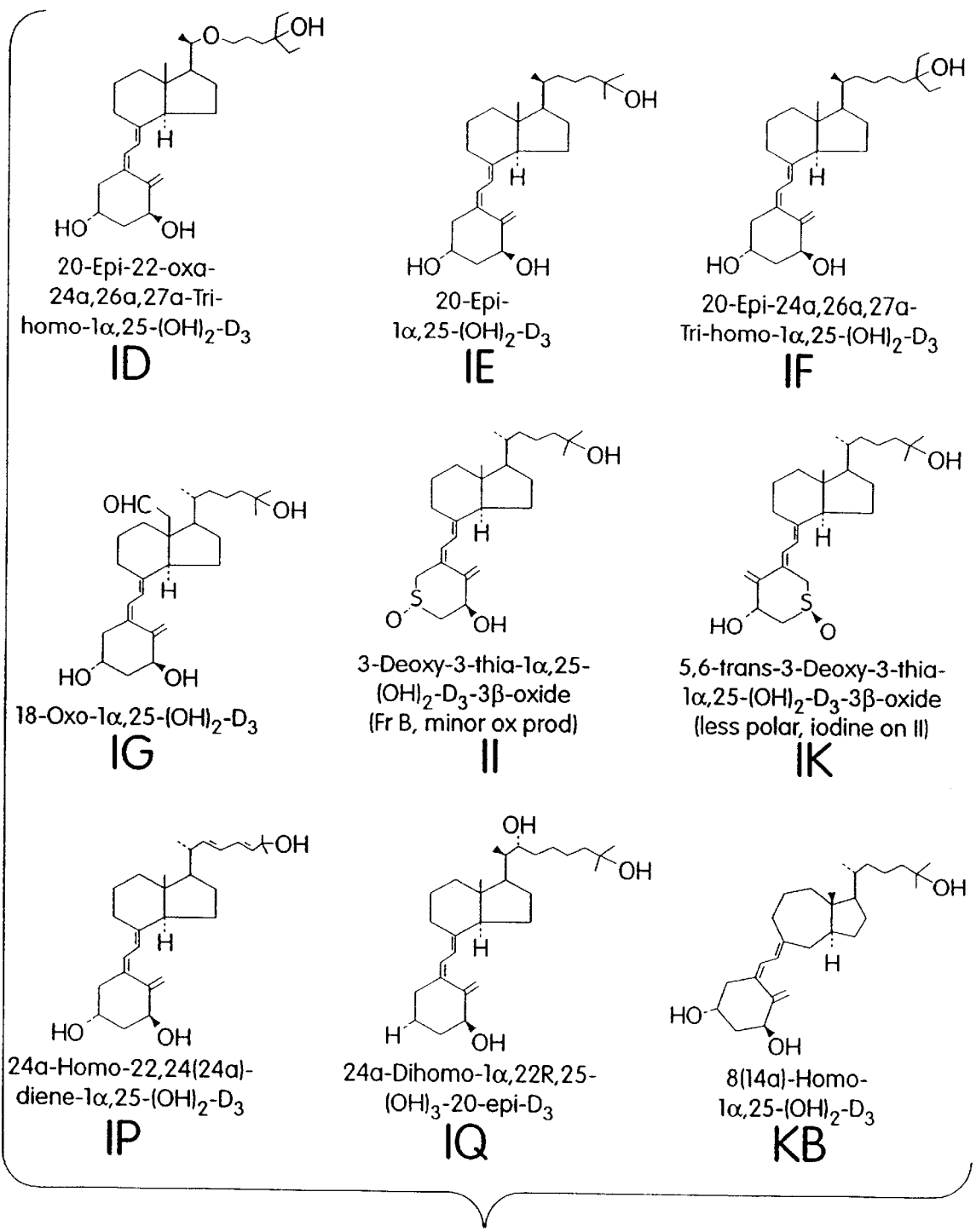
Figures 1, 1A, 2, 3, 4, 5, 6, 7, 8, 9, 10, 11, 12:
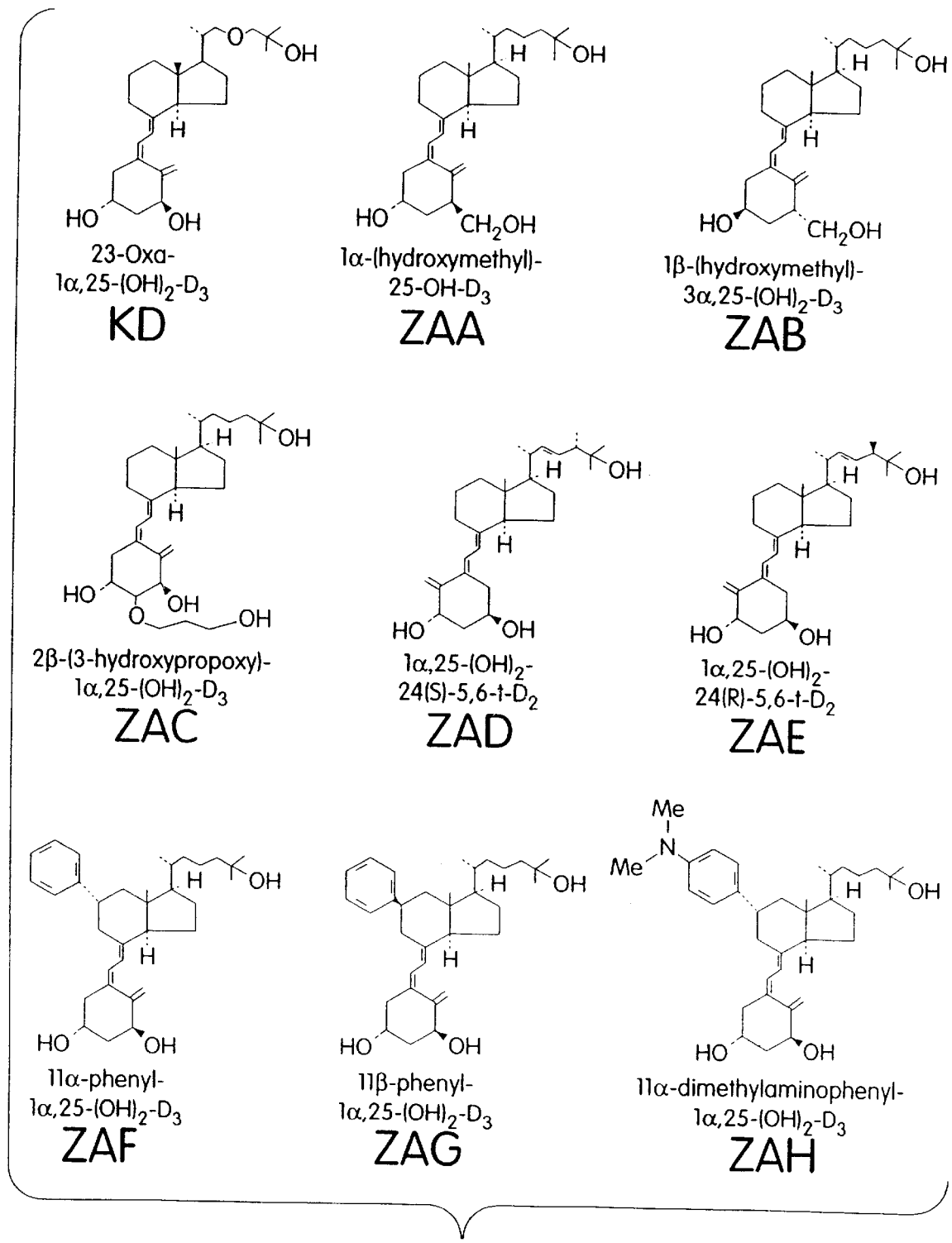
Figures 1, 1A, 2, 3, 4, 5, 6, 7, 8, 9, 10, 11, 12, 13:
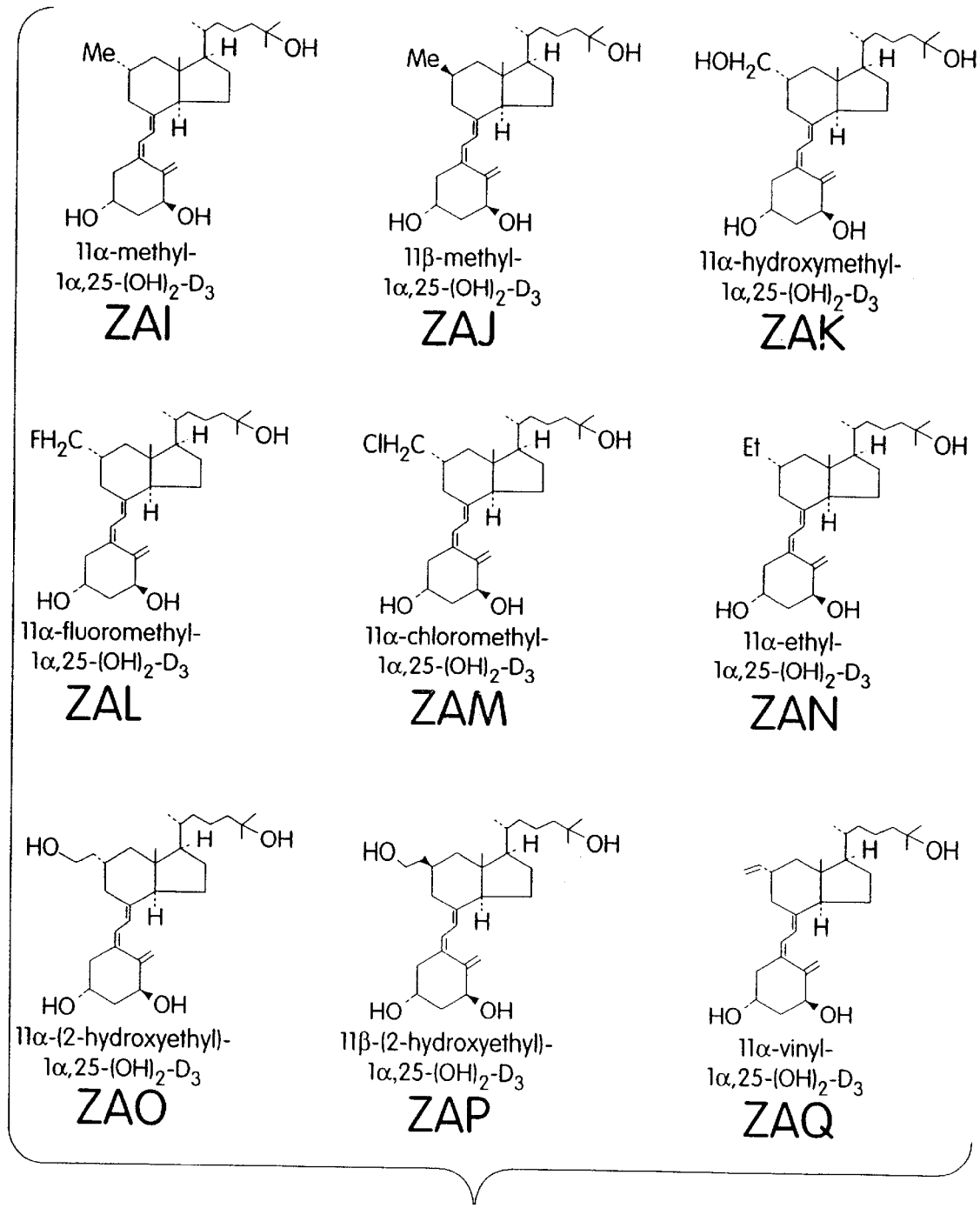
Figures 1, 1A, 2, 3, 4, 5, 6, 7, 8, 9, 10, 11, 12, 13, 14:
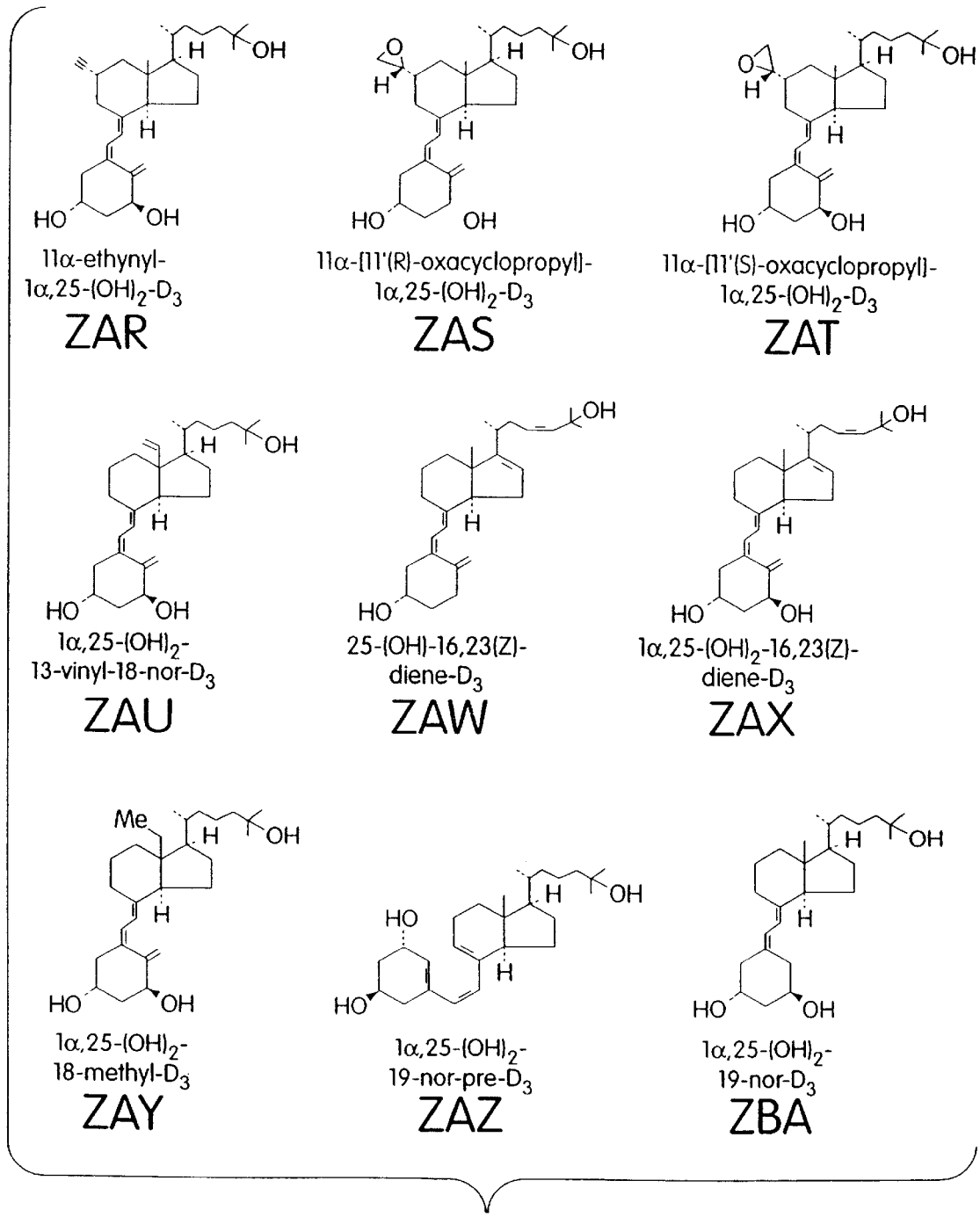
Figures 1, 1A, 2, 3, 4, 5, 6, 7, 8, 9, 10, 11, 12, 13, 14, 15:
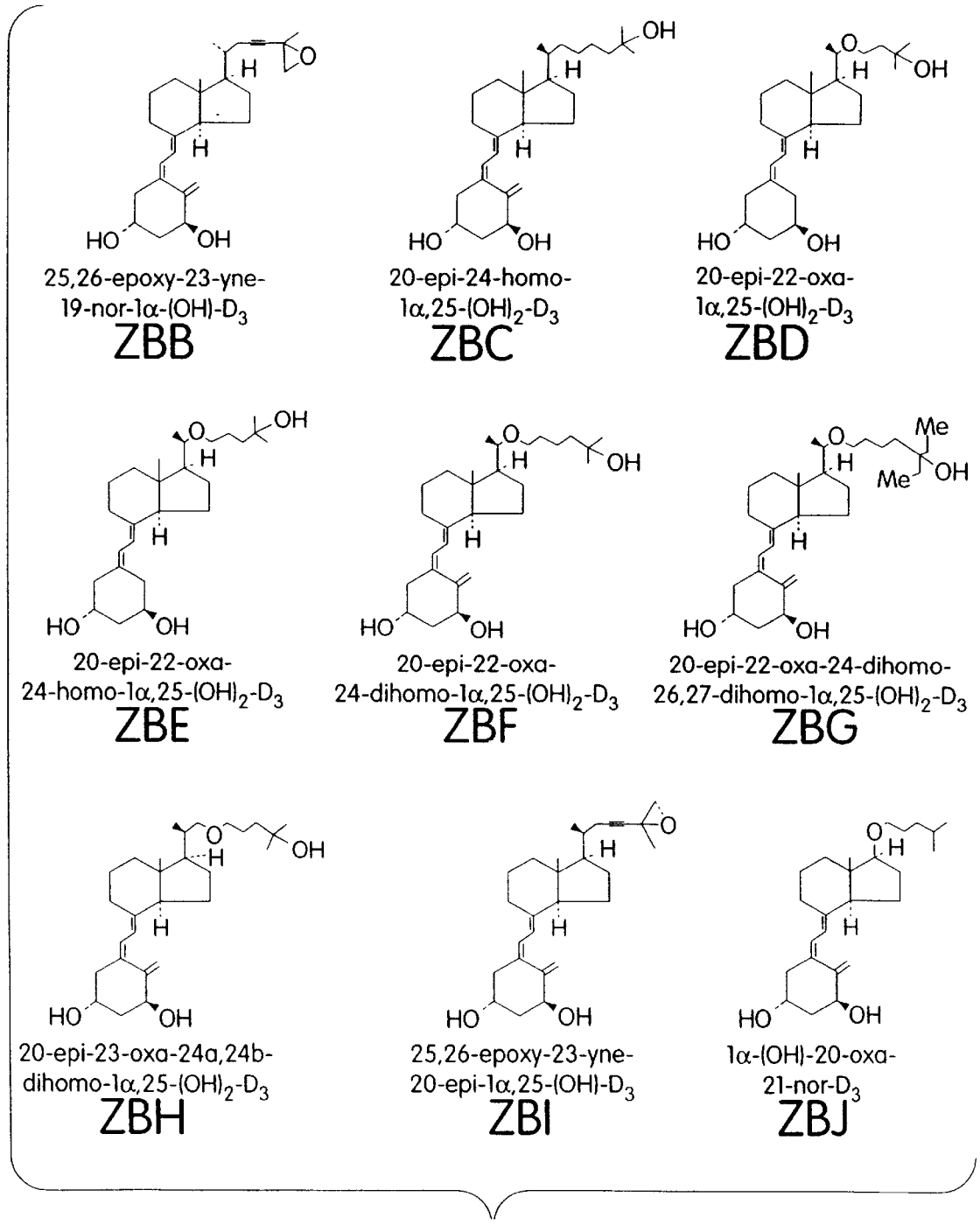
Figures 1, 1A, 2, 3, 4, 5, 6, 7, 8, 9, 10, 11, 12, 13, 14, 15, 16:
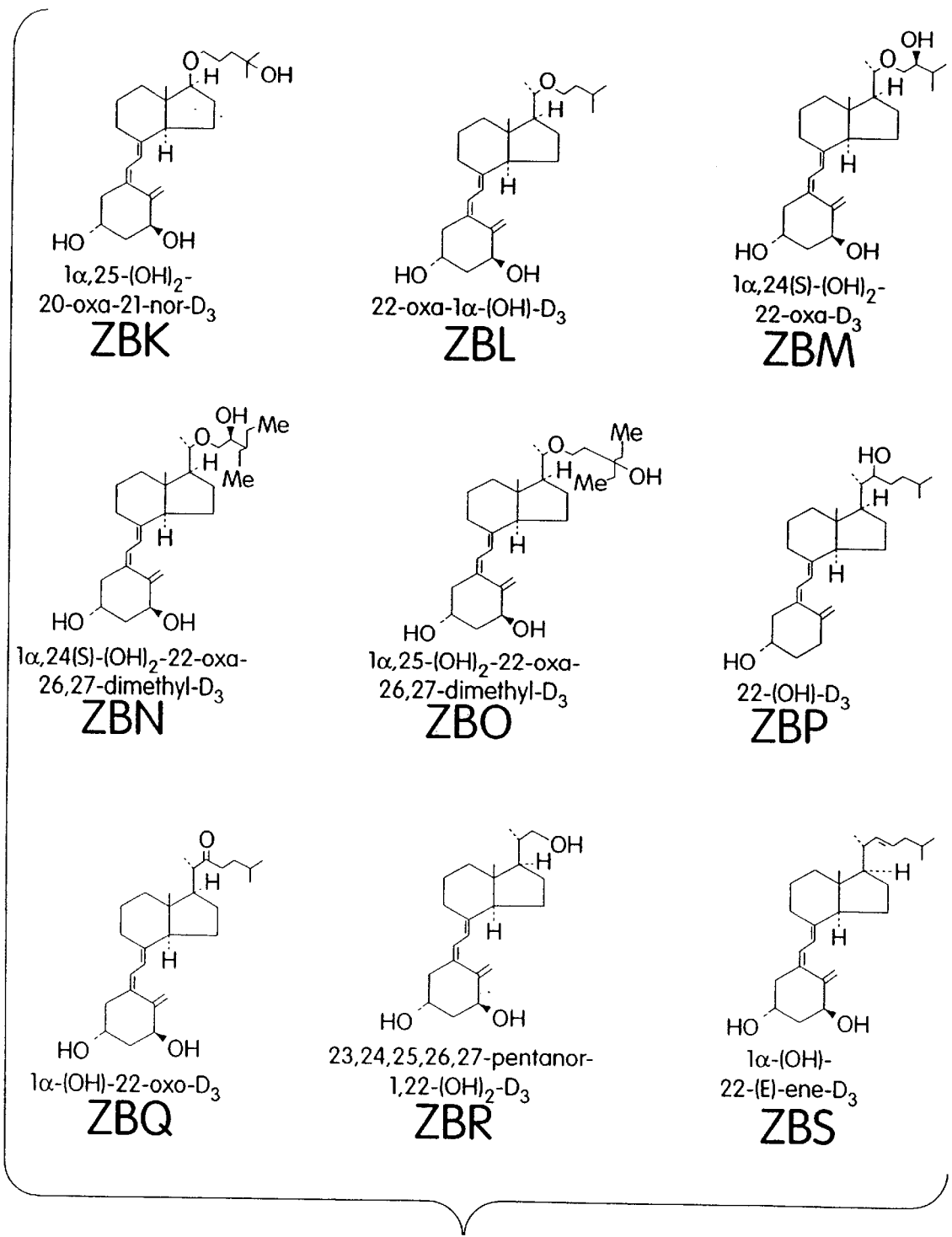
Figures 1, 1A, 2, 3, 4, 5, 6, 7, 8, 9, 10, 11, 12, 13, 14, 15, 16, 17:
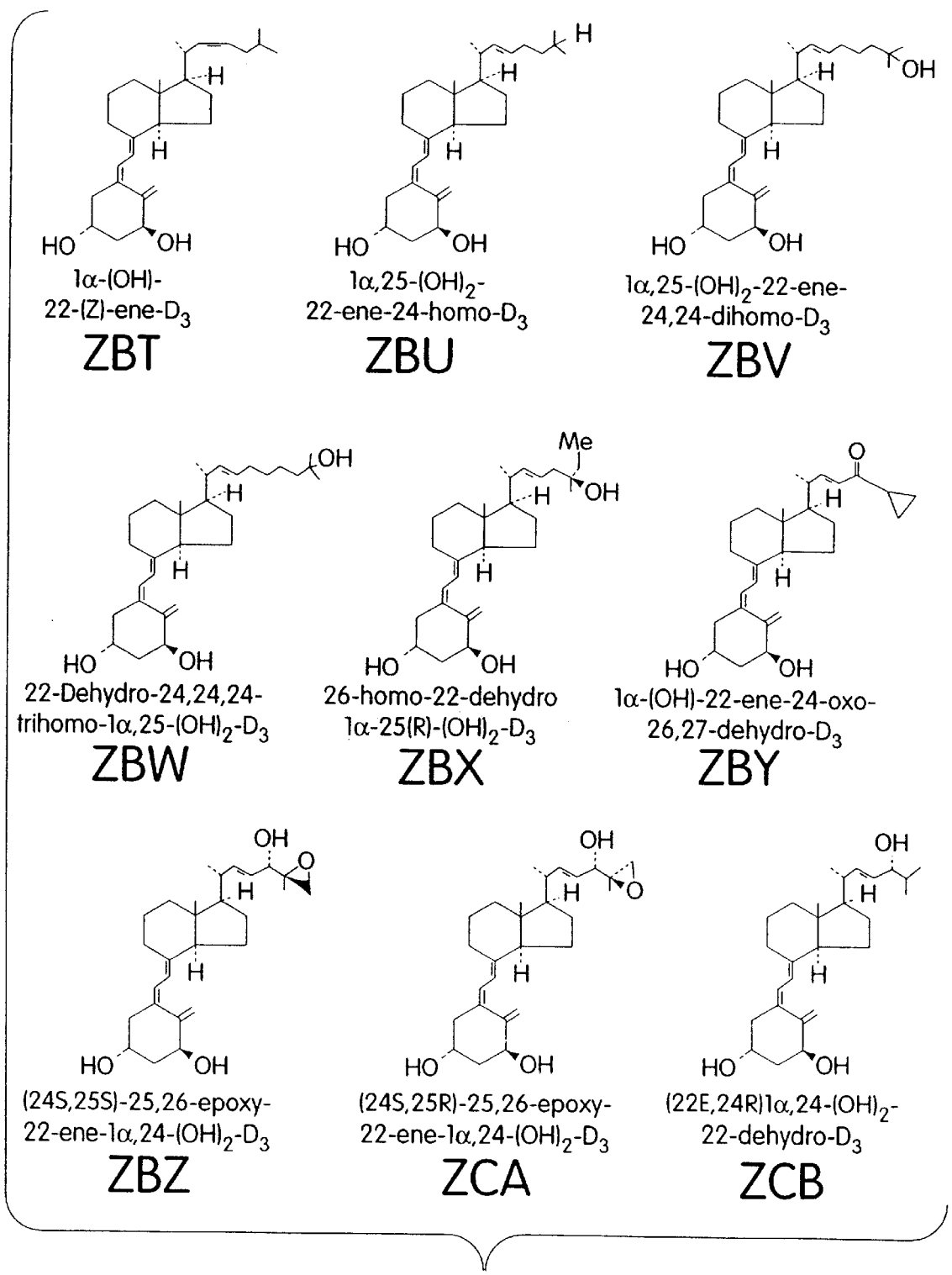
Figures 1, 1A, 2, 3, 4, 5, 6, 7, 8, 9, 10, 11, 12, 13, 14, 15, 16, 17, 18:
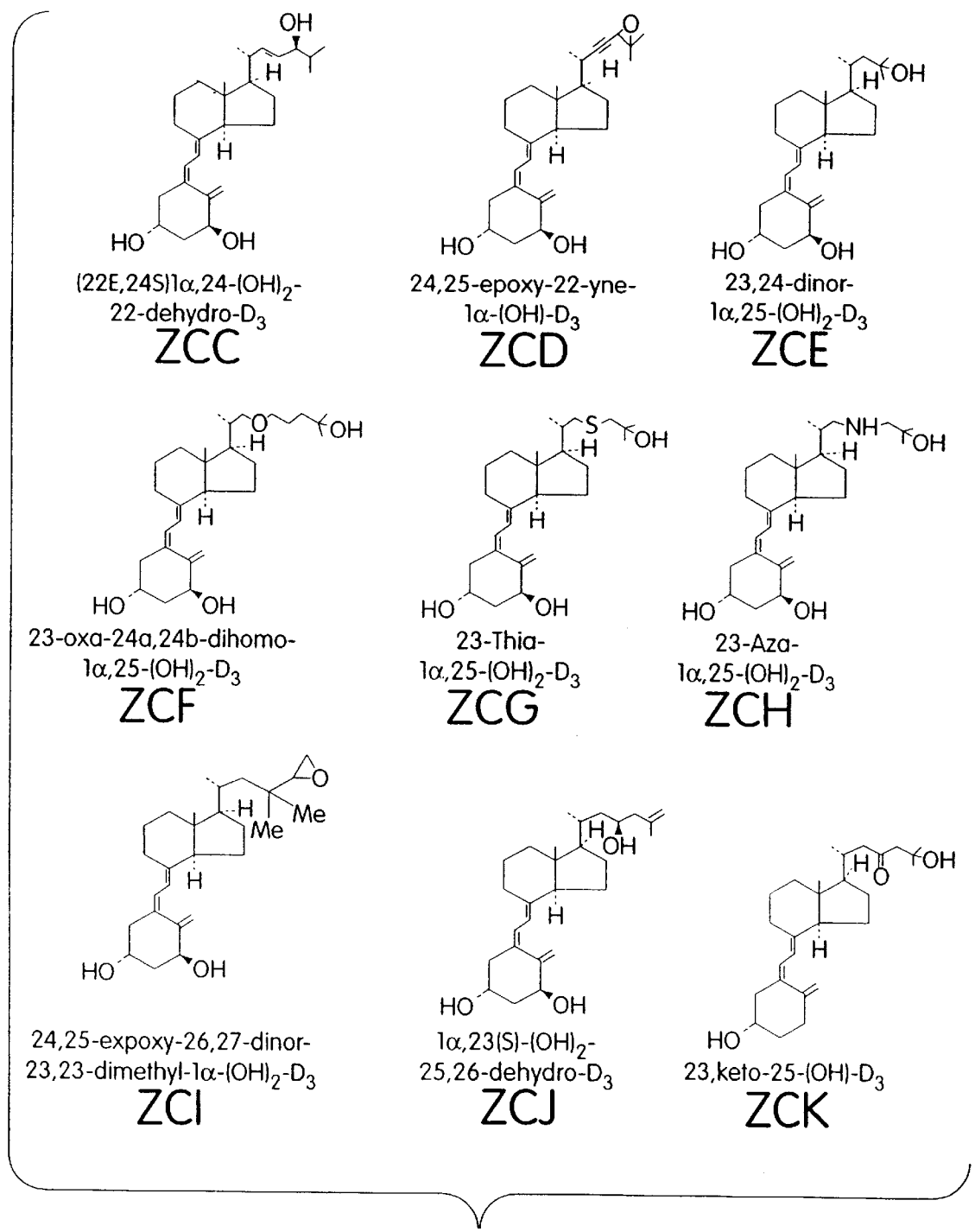
Figures 1, 1A, 2, 3, 4, 5, 6, 7, 8, 9, 10, 11, 12, 13, 14, 15, 16, 17, 18, 19:
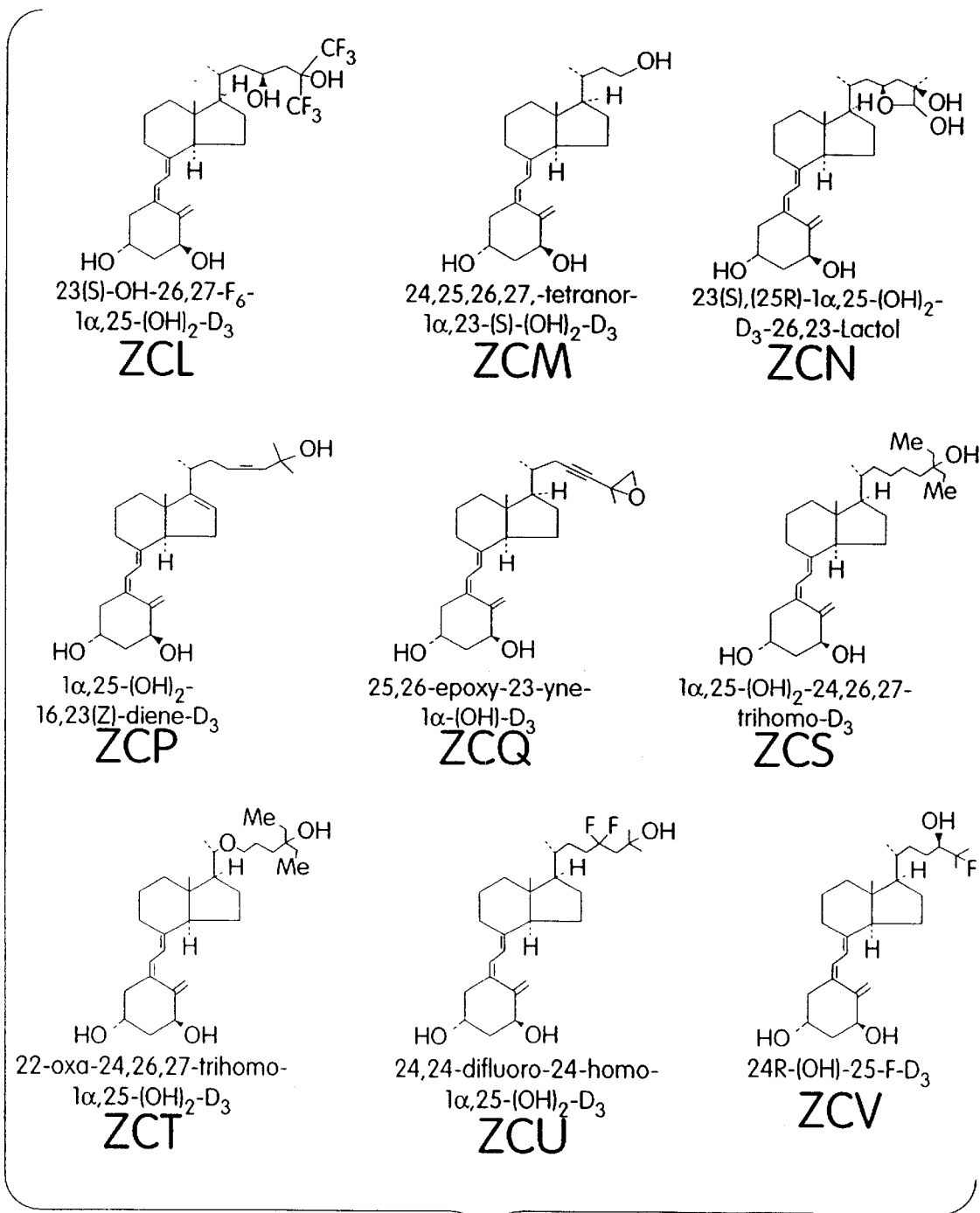
Figures 1, 1A, 2, 3, 4, 5, 6, 7, 8, 9, 10, 11, 12, 13, 14, 15, 16, 17, 18, 19, 20:
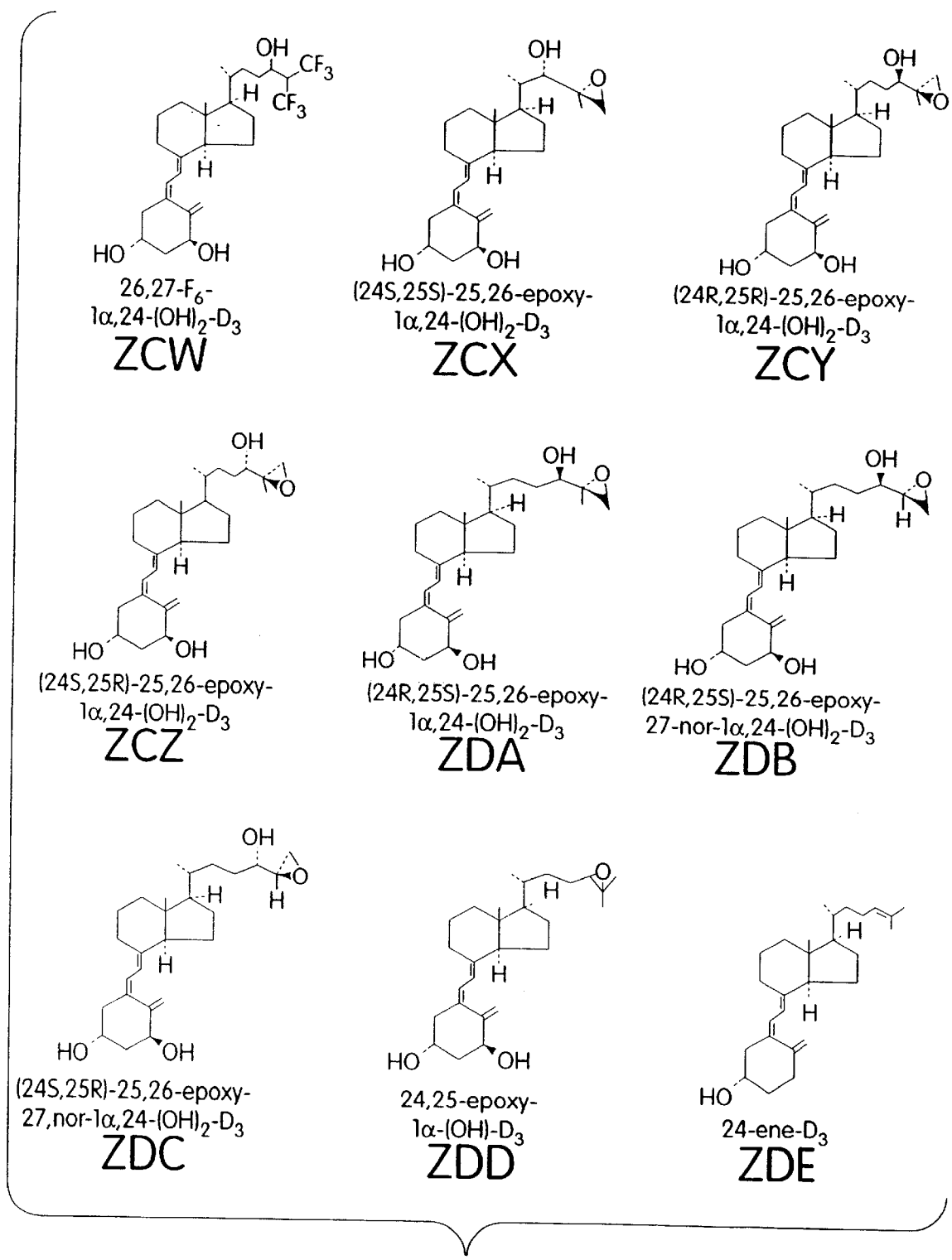
Figures 1, 1A, 2, 3, 4, 5, 6, 7, 8, 9, 10, 11, 12, 13, 14, 15, 16, 17, 18, 19, 20, 21:
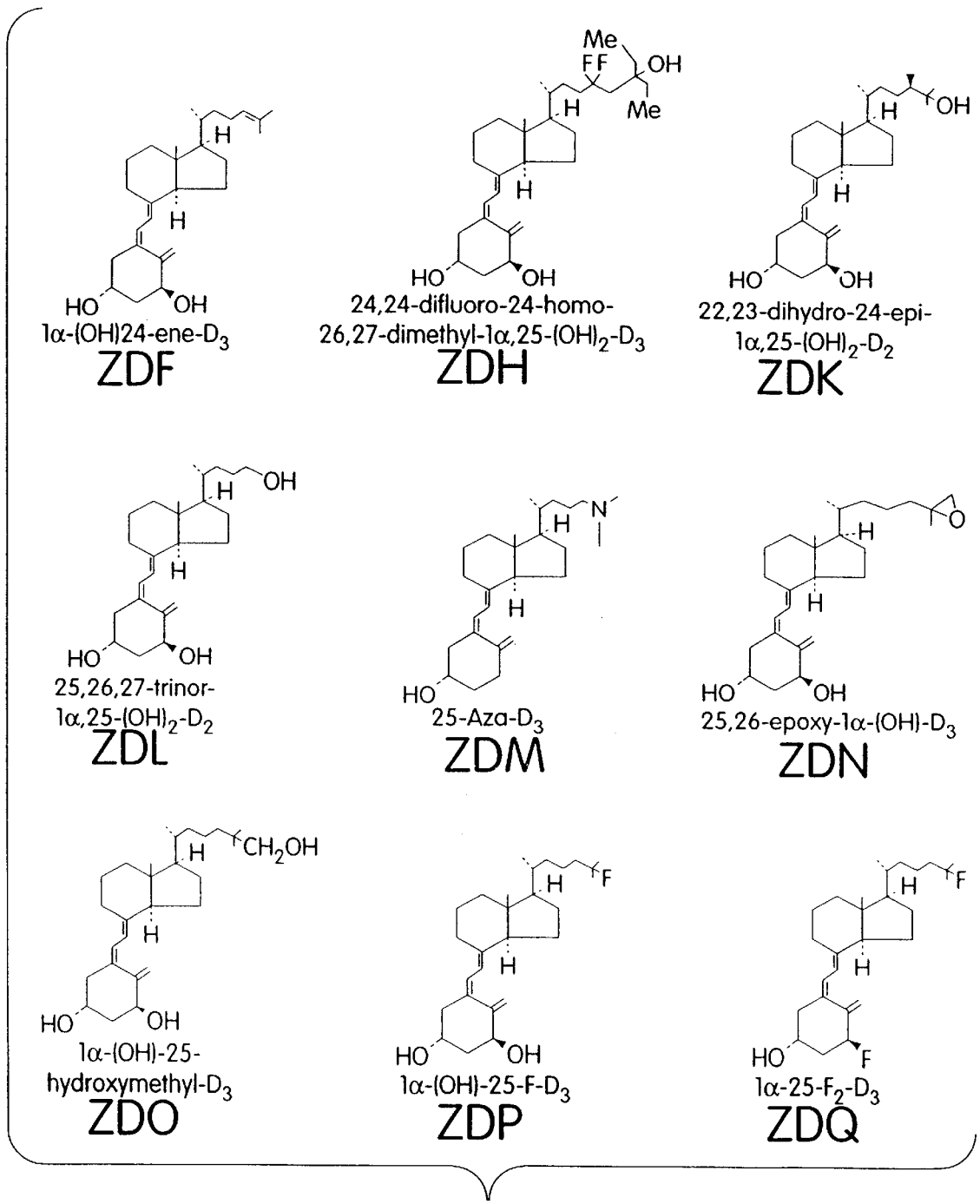
Figures 1, 1A, 2, 3, 4, 5, 6, 7, 8, 9, 10, 11, 12, 13, 14, 15, 16, 17, 18, 19, 20, 21, 22:
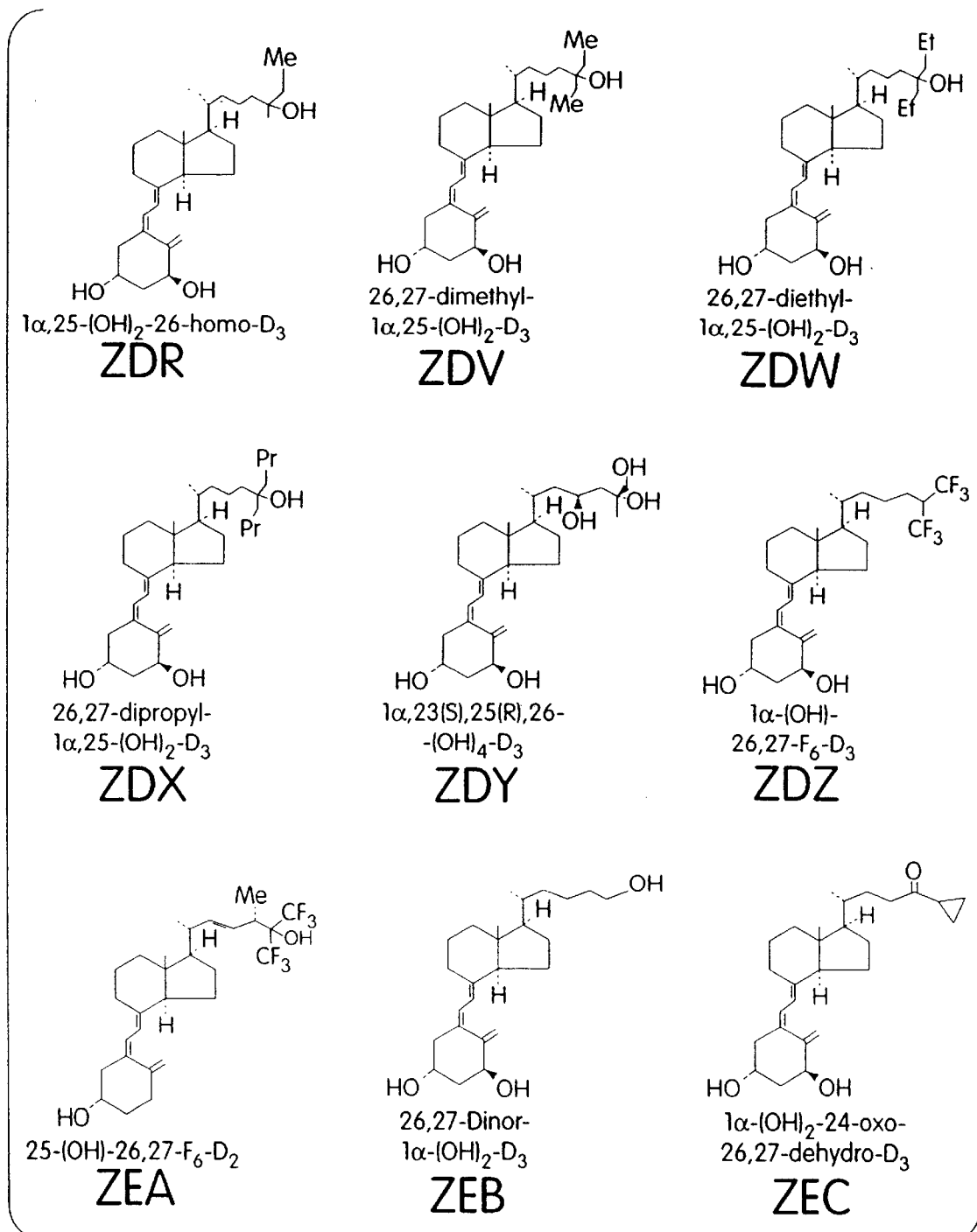
Figures 1, 1A, 2, 3, 4, 5, 6, 7, 8, 9, 10, 11, 12, 13, 14, 15, 16, 17, 18, 19, 20, 21, 22, 23:
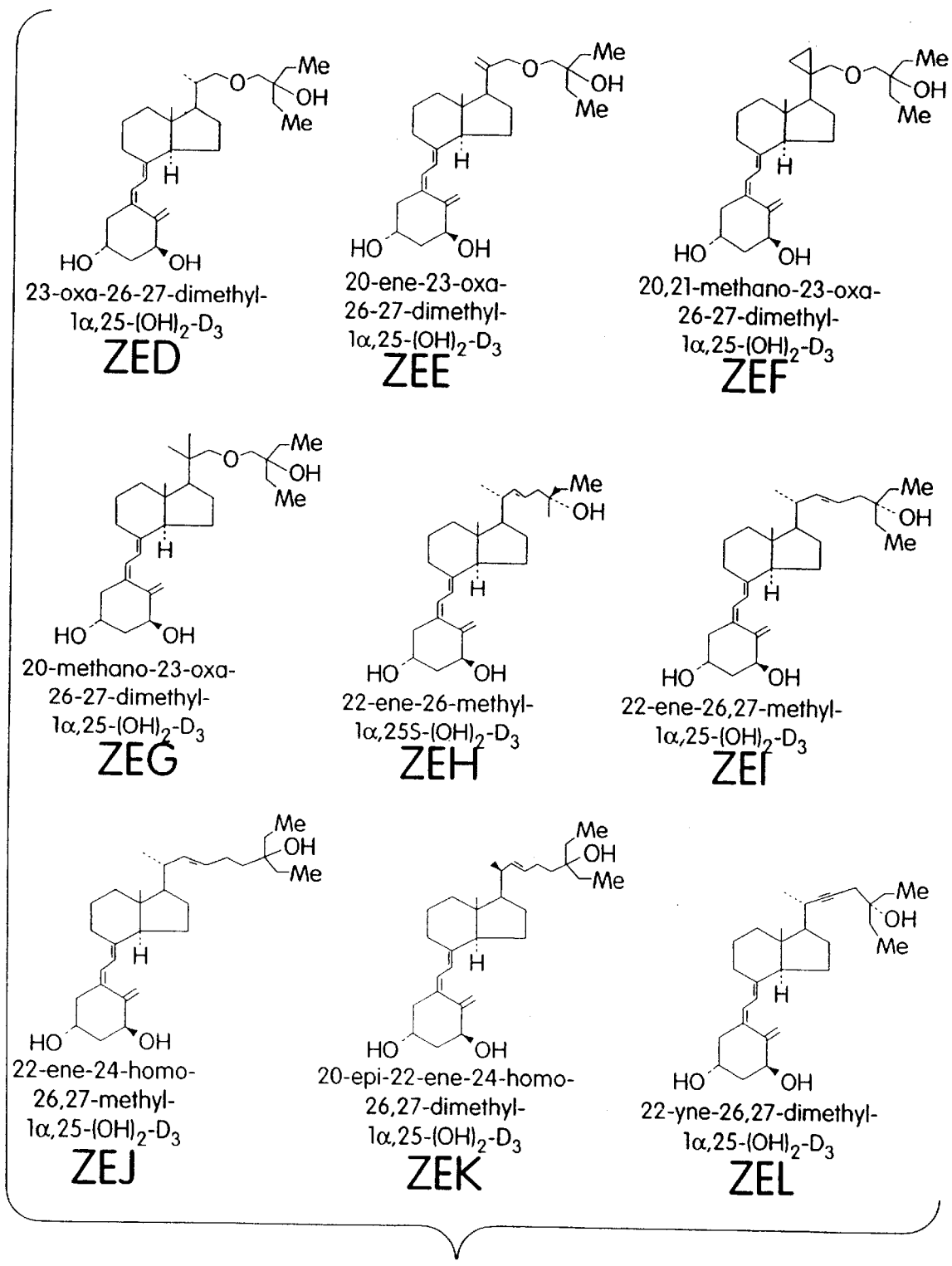
Figures 1, 1A, 2, 3, 4, 5, 6, 7, 8, 9, 10, 11, 12, 13, 14, 15, 16, 17, 18, 19, 20, 21, 22, 23, 24:
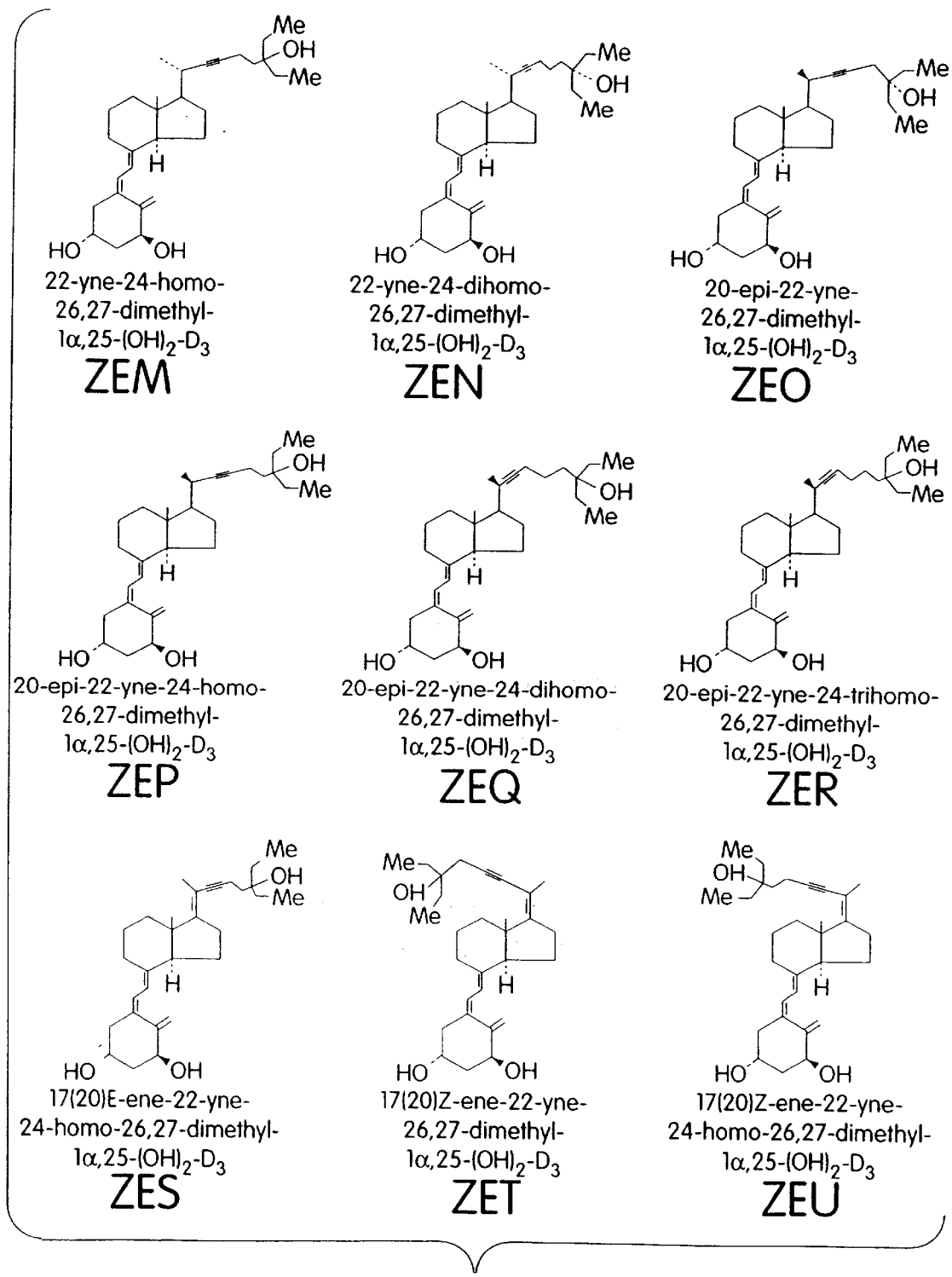
Figures 1, 1A, 2, 3, 4, 5, 6, 7, 8, 9, 10, 11, 12, 13, 14, 15, 16, 17, 18, 19, 20, 21, 22, 23, 24, 25:
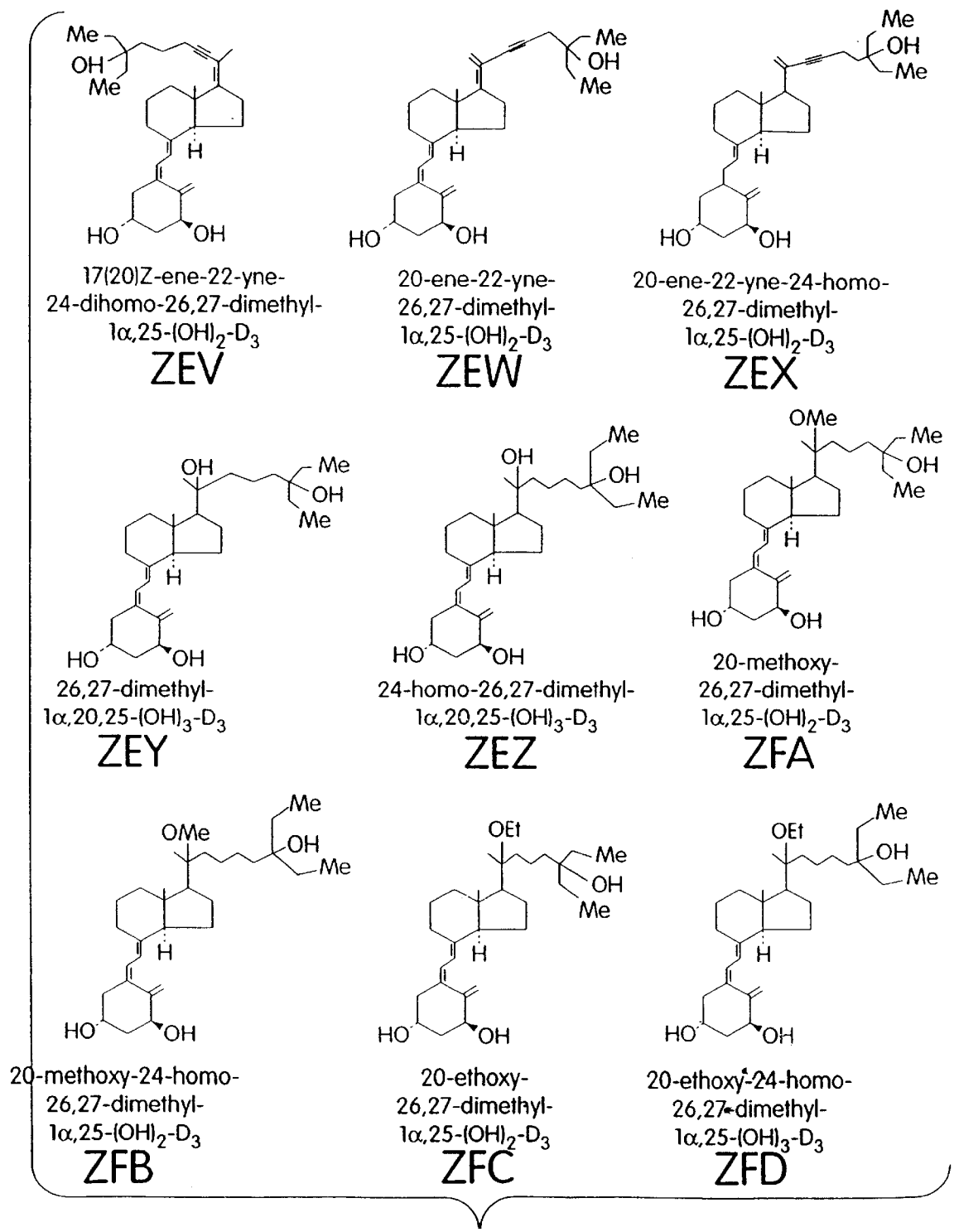
Figures 1, 1A, 2, 3, 4, 5, 6, 7, 8, 9, 10, 11, 12, 13, 14, 15, 16, 17, 18, 19, 20, 21, 22, 23, 24, 25, 26:
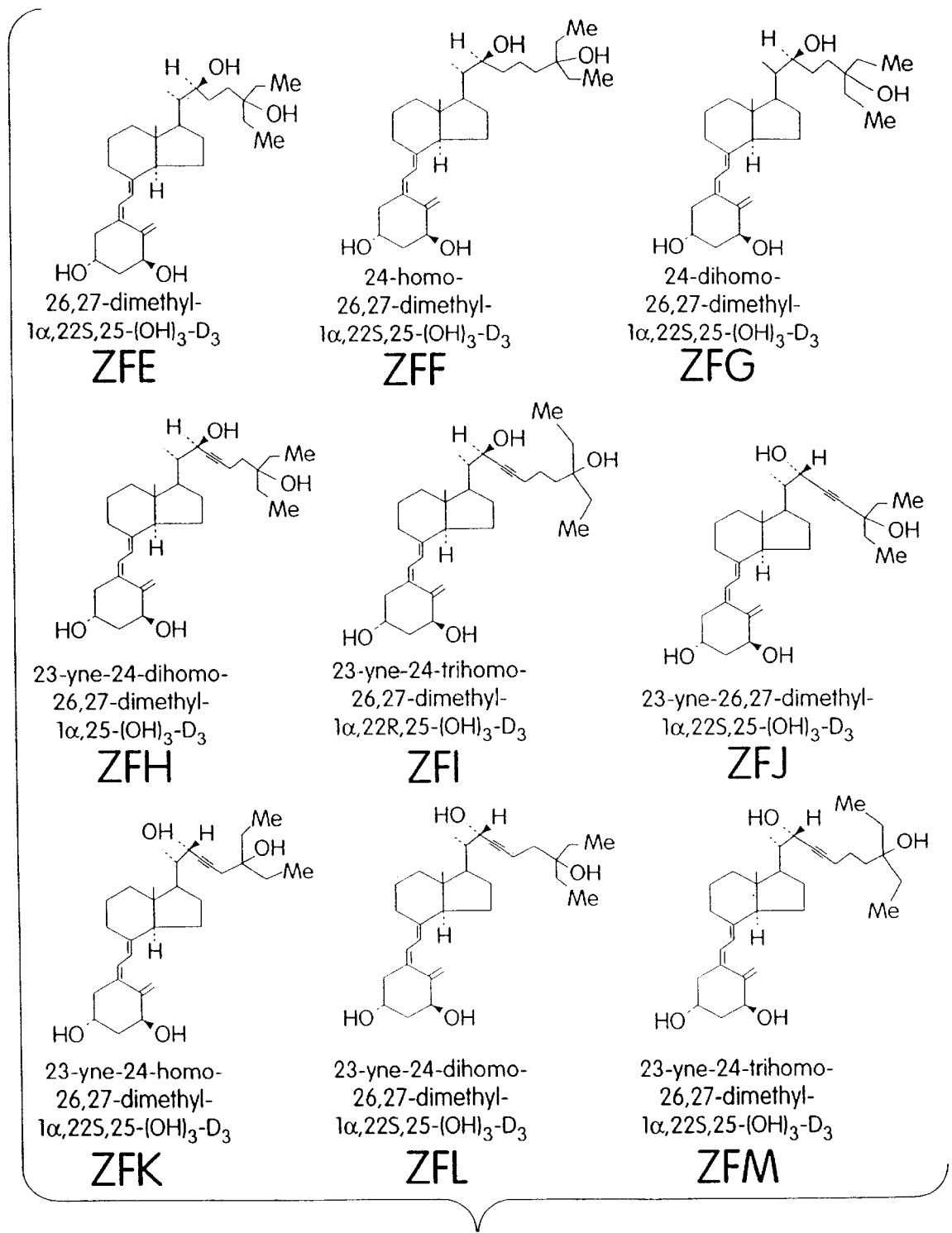
Figures 1, 1A, 2, 3, 4, 5, 6, 7, 8, 9, 10, 11, 12, 13, 14, 15, 16, 17, 18, 19, 20, 21, 22, 23, 24, 25, 26, 27:
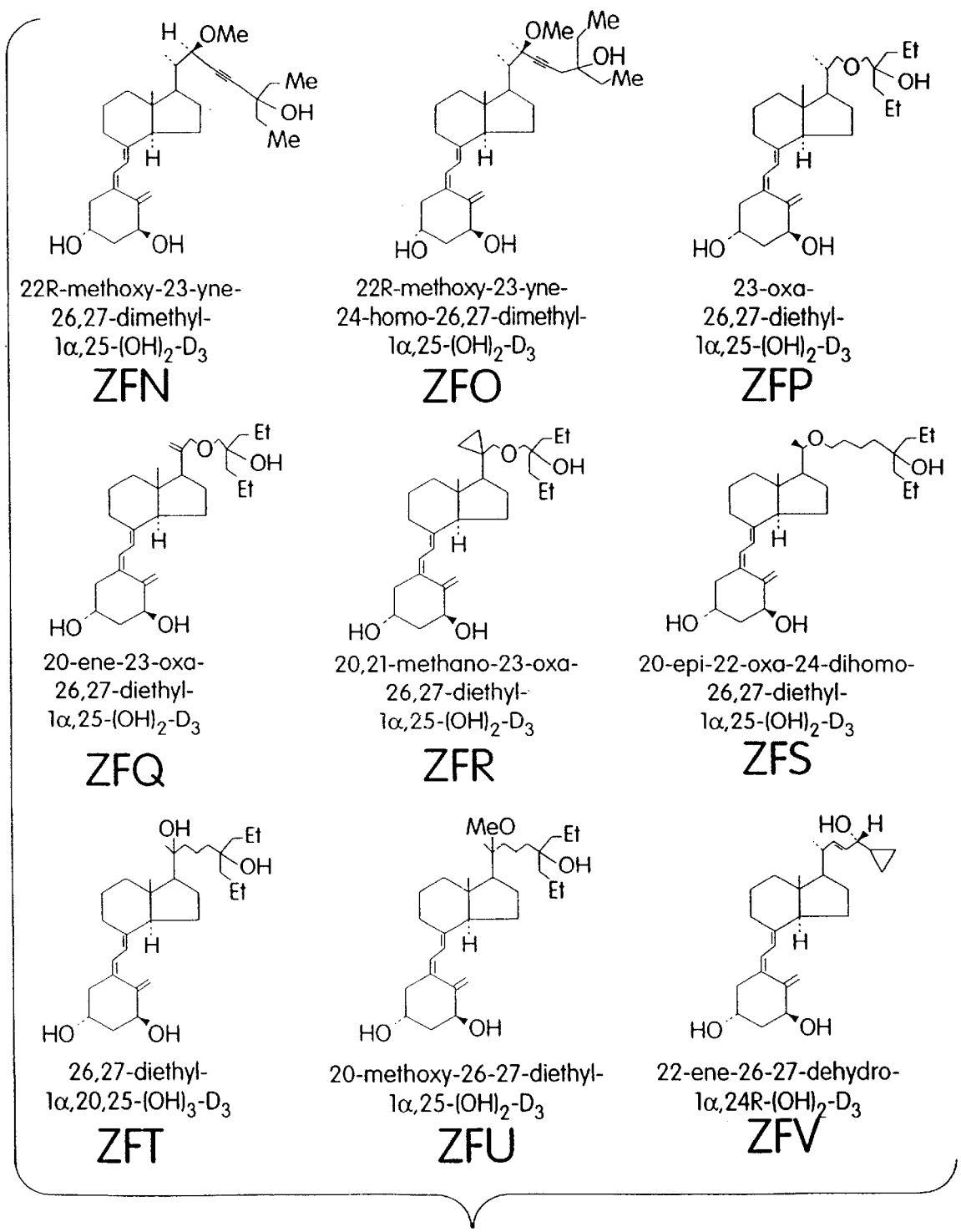
Figures 1, 1A, 2, 3, 4, 5, 6, 7, 8, 9, 10, 11, 12, 13, 14, 15, 16, 17, 18, 19, 20, 21, 22, 23, 24, 25, 26, 27, 28:
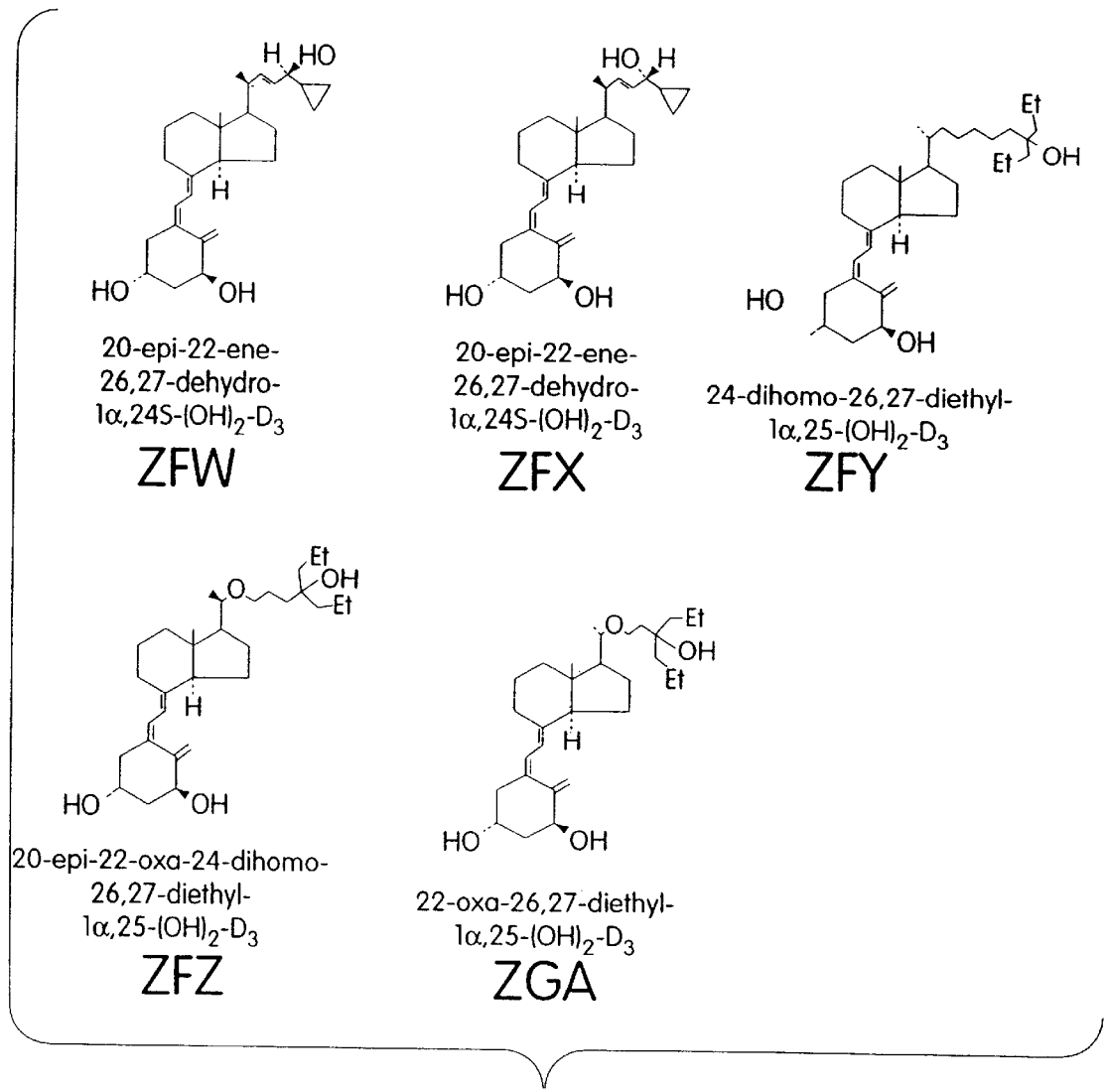
Figure 2:
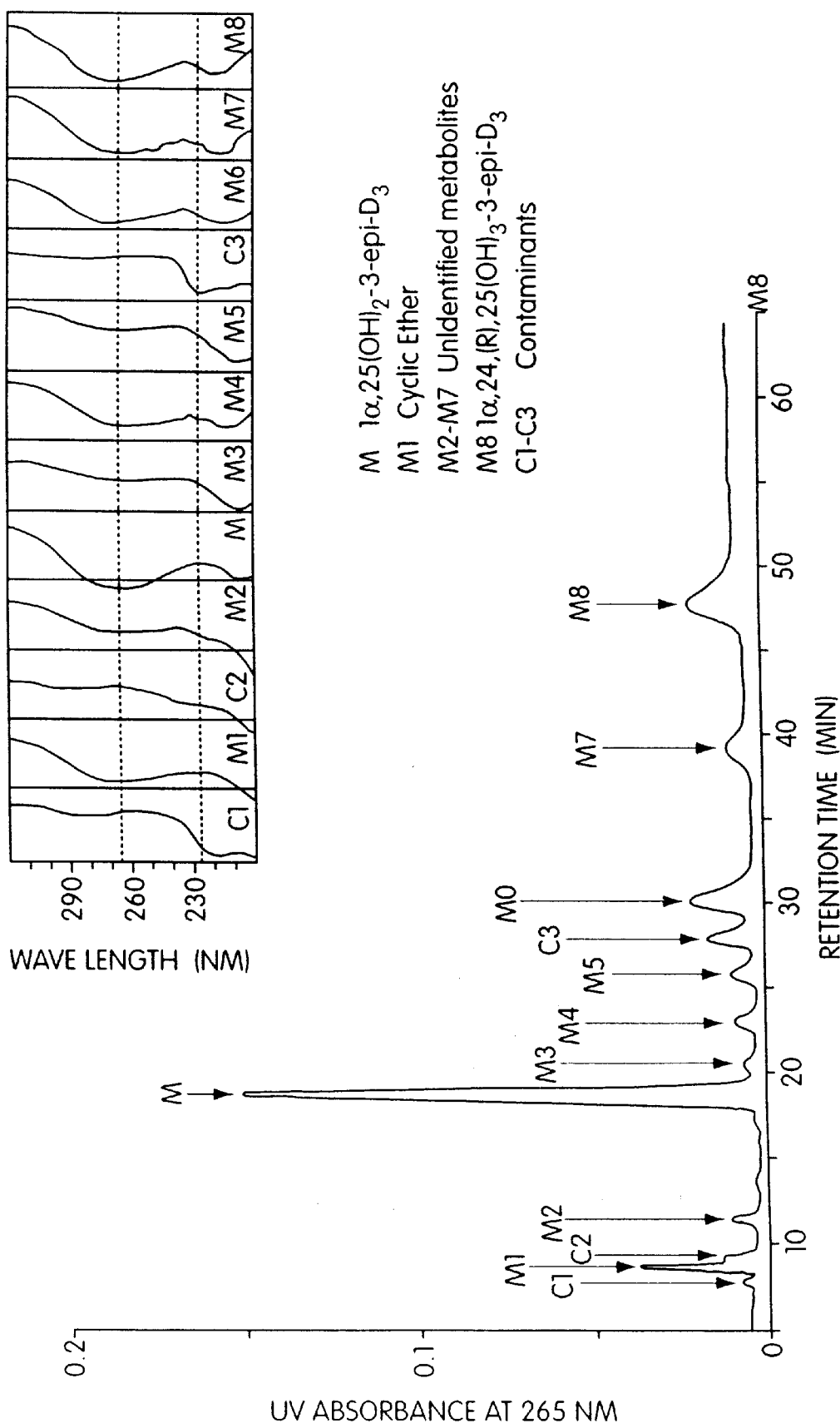
Figure 3:
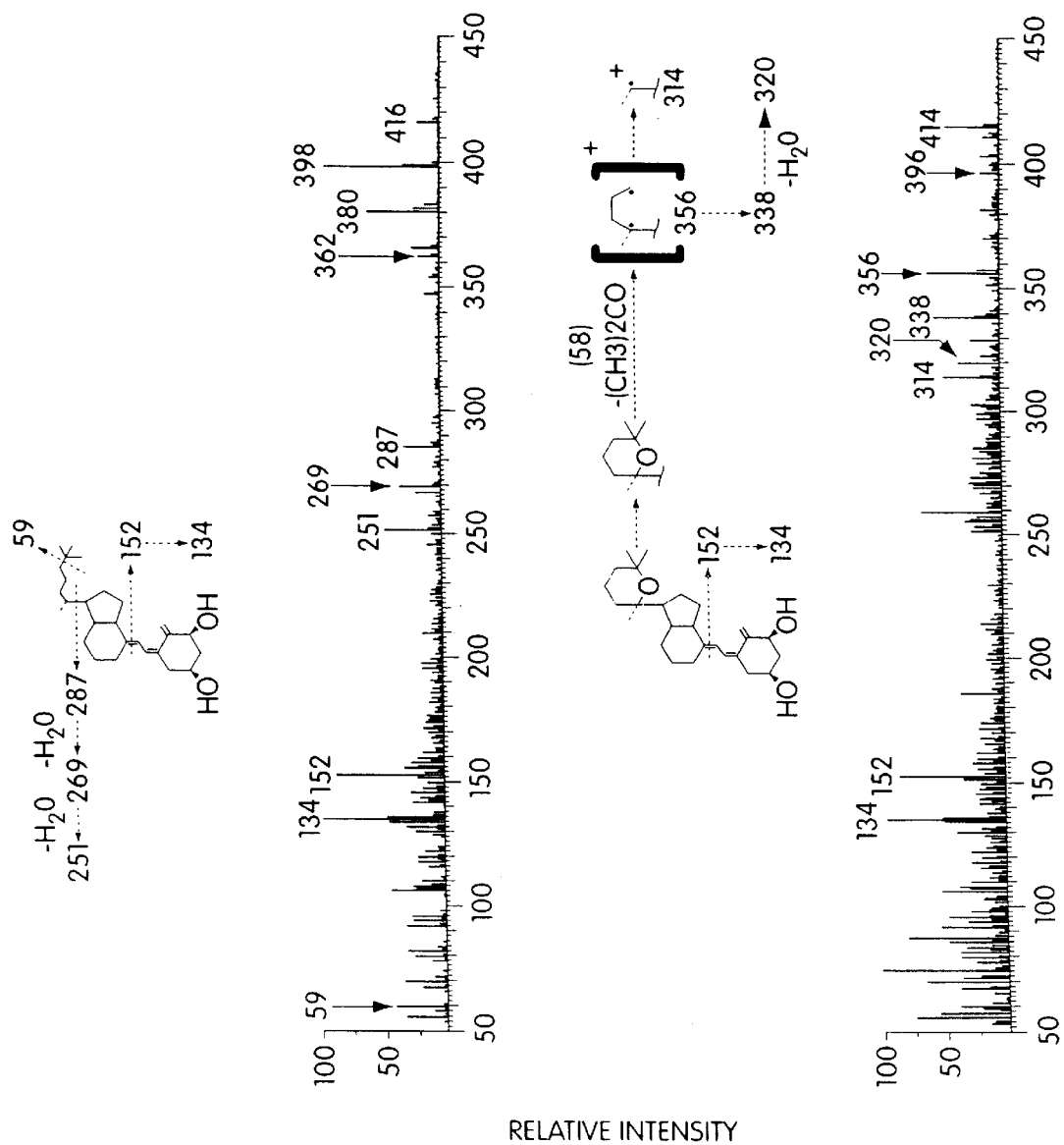
Figure 4:
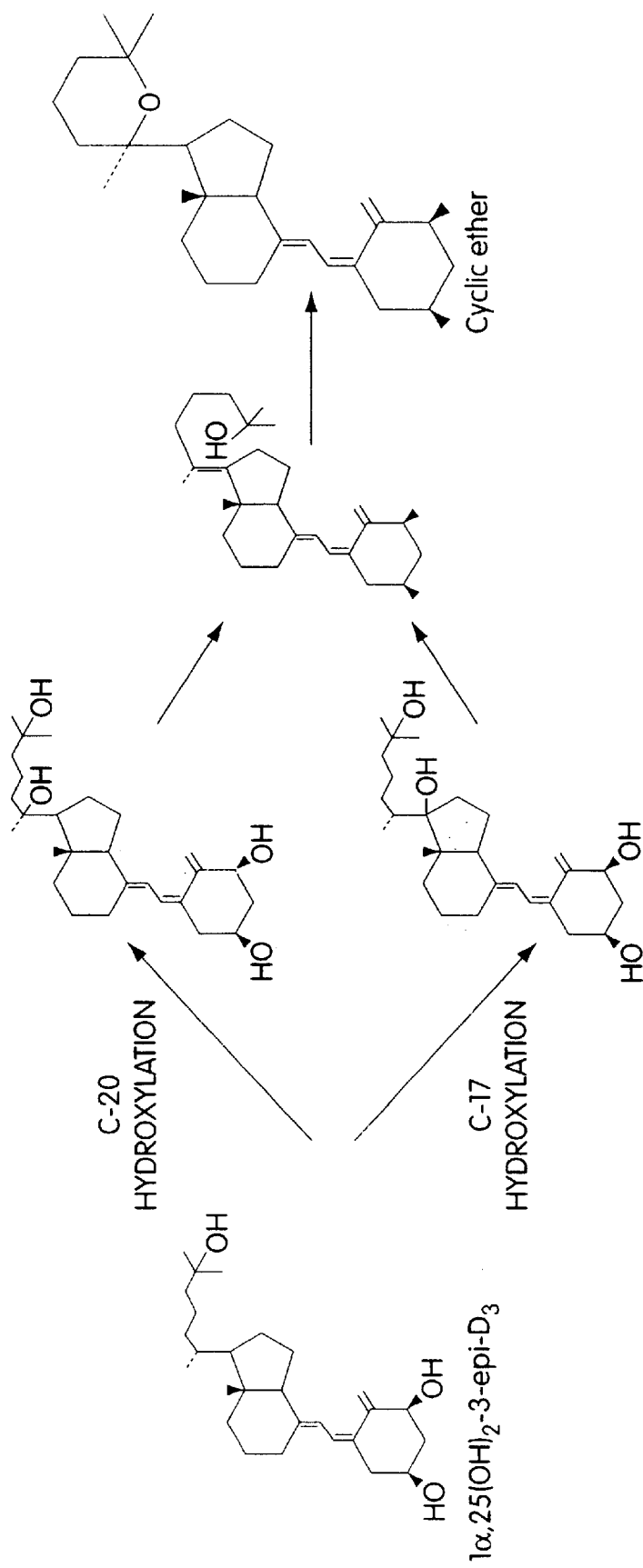

Enhanced Stability In Vivo of 1α(OH) 3-epi Vitamin $D_3$ Compared to Its Isomeric Counterpart The stability of 1α(OH) 3-epi vitamin $D_3$ in vivo was characterized by monitoring the changes in the concentration of 1α(OH) 3-epi vitamin $D_3$ and its isomeric counterpart at various time intervals. In particular, FIG. 7 shows the HPLC profile and UV spectra of the metabolites produced in rat osteosarcoma cell lines (UMR-106) which were incubated with 1α(OH)$D_3$ for 24, 48, or 84 hours. Peak M and S represent the relative concentrations of 1α(OH) 3-epi vitamin $D_3$ and its isomeric counterpart, respectively, at the time intervals tested. The persistent duration of peak M relative to peak S after 48 and 84 hour-incubations indicates that 3-epi metabolite of 1α(OH)$D_3$ are more stable in vivo than its isomeric counterpart Equivalents Those skilled in the art will recognize, or be able to ascertain using no more than routine experimentation, many equivalents of the specific embodiments of the invention described herein. Such equivalents are intended to be encompassed by the following claims.

What is claimed is:

1. A packaged compound, comprising a vitamin D3 compound having the formula I as follows:

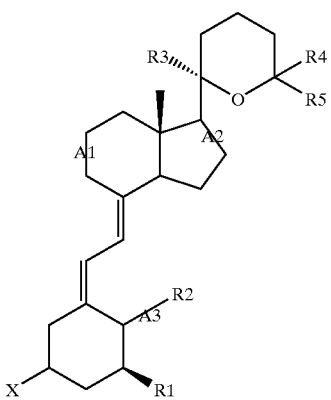

wherein $A_1$, $A_2$ and $A_3$ are a single or a double bond; X, $R_1$, $R_2$, $R_3$, $R_4$ and $R_5$ are selected from the group consisting of a hydrogen, a halogen, a haloalkyl, a hydroxy, a hydroxy-protecting group, an alkyl, an alkenyl, an alkynyl, an alkoxy, an aryl group and a heterocyclic group, and packaged with instructions for use of the compound for treating a disorder characterized by an aberrant activity of a vitamin $D_3$-responsive cell.

2. A packaged compound, comprising a vitamin D3 compound having the formula II as follows:

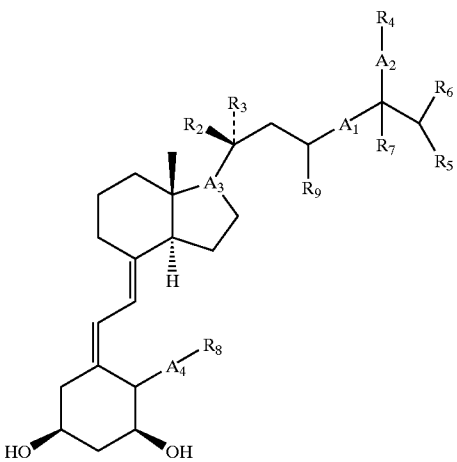

wherein $A_1$ is a single, a double, or a triple bond; $A_2$, $A_3$ and A4 are each independently selected from the group consisting of a single or a double bond; $R_2$, $R_3$, $R_4$, $R_7$, $R_8$ and $R_9$ are independently selected from the group consisting of a hydrogen, a deuterium, a deuteroalkyl, a hydroxy, an alkyl, an alkoxide, an O-acyl, a halogen, a haloalkyl, a hydroxyalkyl, an amine or a thiol group, and wherein the pairs of $R_2$ and $R_3$, and $R_4$ and $R_7$ taken together are an oxygen atom; and $R_5$ and $R_6$ are independently selected from the group consisting of a hydrogen, a deuterium, a halogen, an alkyl, a hydroxyalkyl, a haloalkyl, and a deuteroalkyl, and packaged with instructions for use of the compound for treating a disorder characterized by an aberrant activity of a vitamin $D_3$-responsive cell.

3. The packaged compound of claim 2, wherein the vitamin D3 compound is 1α(OH) vitamin D3, 1α, 24 dihydroxy 3-epi vitamin $D_3$, 1α hydroxy 24-ethyl 3-epi vitamin $D_3$, 1α hydroxy 24-methyl 3-epi vitamin $D_3$, or 1α, 24-dihydroxy 24-methyl 3-epi vitamin $D_3$.

4. The packaged compound of claims 1 or 2, wherein the disorder comprises an aberrant activity of a hyperproliferative skin cell.

5. The packaged compound of claims 1 or 2, wherein the disorder comprises an aberrant activity of an endocrine cell.

6. The packaged compound of claim 5, wherein the endocrine cell is a parathyroid cell and the aberrant activity is processing and/or secretion of parathyroid hormone.

7. The packaged compound of claim 6, wherein the disorder is secondary hyperparathyroidism.

8. The packaged compound of claim 7, wherein the disorder comprises an aberrant activity of a bone cell.

9. The packaged compound of claim 8, wherein the disorder is selected from the group consisting of osteoporosis, osteodystrophy, senile osteoporosis, osteomalacia, rickets, osteitis fibrosa cystica, renal osteodystrophy, secondary hyperparathyroidism, cirrhosis, and chronic renal disease.

* * * * *